US009005643B2

(12) United States Patent
Melander et al.

(10) Patent No.: US 9,005,643 B2
(45) Date of Patent: Apr. 14, 2015

(54) INHIBITION OF BACTERIAL BIOFILMS WITH IMIDAZOLE-PHENYL DERIVATIVES

(75) Inventors: Christian Melander, Raleigh, NC (US); Justin J. Richards, Durham, NC (US); Cynthia Bunders, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 1225 days.

(21) Appl. No.: 12/417,981

(22) Filed: Apr. 3, 2009

(65) Prior Publication Data

US 2009/0270475 A1 Oct. 29, 2009

Related U.S. Application Data

(60) Provisional application No. 61/042,473, filed on Apr. 4, 2008.

(51) Int. Cl.
*A01N 43/50* (2006.01)
*A01P 1/00* (2006.01)
*A61K 31/4168* (2006.01)
*A61K 31/397* (2006.01)
*C07D 233/88* (2006.01)
*C07D 405/12* (2006.01)
*C07D 409/12* (2006.01)
*C07D 403/10* (2006.01)

(52) U.S. Cl.
CPC .......... *C07D 233/88* (2013.01); *A61K 31/4168* (2013.01); *A01N 43/50* (2013.01); *C07D 403/10* (2013.01); *C07D 405/12* (2013.01); *C07D 409/12* (2013.01)

(58) Field of Classification Search
CPC . A01N 43/50; C07D 233/88; A61K 31/4168; A61K 31/397
See application file for complete search history.

(56) References Cited

U.S. PATENT DOCUMENTS

| | | | |
|---|---|---|---|
| 3,575,929 A | 4/1971 | Jones | |
| 4,514,382 A | 4/1985 | Gaffar et al. | |
| 4,665,192 A | 5/1987 | Cerami | |
| 4,758,583 A | 7/1988 | Cerami et al. | |
| 4,983,604 A | 1/1991 | Ulrich et al. | |
| 5,128,360 A | 7/1992 | Cerami et al. | |
| 5,238,963 A | 8/1993 | Cerami et al. | |
| 5,358,960 A | 10/1994 | Ulrich et al. | |
| 5,476,849 A | 12/1995 | Ulrich et al. | |
| 5,534,540 A | 7/1996 | Ulrich et al. | |
| 5,656,261 A | 8/1997 | Cerami et al. | |
| 5,670,055 A | 9/1997 | Yu et al. | |
| 5,814,668 A | 9/1998 | Whittemore et al. | |
| 5,834,411 A | 11/1998 | Bolkan et al. | |
| 6,121,300 A | 9/2000 | Wagle et al. | |
| 6,143,774 A | 11/2000 | Heckmann et al. | |
| 6,338,904 B1 * | 1/2002 | Patnaik et al. | 428/423.1 |
| 6,790,859 B2 | 9/2004 | Wagle et al. | |
| 7,087,661 B1 | 8/2006 | Alberte et al. | |
| 7,132,567 B2 | 11/2006 | Alberte et al. | |
| 7,160,879 B2 | 1/2007 | DeSimone et al. | |
| 7,514,458 B2 | 4/2009 | Cogan et al. | |
| 2003/0171421 A1 | 9/2003 | Davies et al. | |
| 2003/0229000 A1 | 12/2003 | Merritt et al. | |
| 2004/0024037 A1 | 2/2004 | Ryu et al. | |
| 2004/0249441 A1 | 12/2004 | Miller et al. | |
| 2005/0161859 A1 | 7/2005 | Miller et al. | |
| 2006/0018945 A1 | 1/2006 | Britigan et al. | |
| 2006/0228384 A1 | 10/2006 | Eldridge | |
| 2006/0276468 A1 | 12/2006 | Blow | |
| 2007/0231291 A1 | 10/2007 | Huang et al. | |
| 2008/0181923 A1 | 7/2008 | Melander et al. | |

FOREIGN PATENT DOCUMENTS

WO    WO 2005/012263 A1    2/2005

OTHER PUBLICATIONS

Stella, Valentino J., "Prodrugs as therapeutics" Expert Opinion of Therapeutic Patents, 2004 14(3), 277-280.*
Wolff et al. Burger's Medicinal Chemistry, 5th Ed., vol. 1, pp. 975-977, 1994.*
Testa, Bernard, "Prodrug Research: futile or fertile?" Biochemical Pharmacology, 2004, 68 2097-2106.*
Ettmayer, Peter, "Lessons Learned from Marketed and Investigational Prodrugs", Medicinal Chemistry, 2004, 47(10), 2394-2404.*
Lata et al. "Analysis and prediction of antibacterial peptides", BMC Bioinformatics, 2007, 8:263-272.*
Cavalleri et al. "Synthesis and Biological Activity of some 2-Aminoimidazoles" Arzneim.-Forsch./Drug Res. 27(10), 1977, 1889-95.*
Worthington et al. ("Small molecule suppression of carbapenem resistance in NDM-1 producing Klebsiella pneumoniae" ACS Med. Chem. Lett. 2012, 3, 357-361).*
International Search Report and Written Opinion for PCT/US08/01045, dated May 9, 2008.
Foley L and Büchi G. Biomimetic synthesis of dibromophakellin. J. Am. Chem. Soc. 1982; 104: 1776-1777.
Yamada A et al. Development of chemical substances regulating biofilm formation. Bull. Chem. Soc. Jpn. 1997; 70: 3061-3069.
Mourabit AA and Potier P. Sponge's molecular diversity through the ambivalent reactivity of 2-aminoimidazole: a universal chemical pathway to the oroidin-based pyrrole-imidazole alkaloids and their palau'amine congeners. Eur. J. Org. Chem. 2001: 237-243.
Hoffmann H and Lindel T. Synthesis of the pyrrole-imidazolealkaloids. Synthesis. 2003; 12: 1753-1783.
Kelly SR et al. Effects of Caribbean sponge extracts on bacterial attachment. Aquatic Microbial Ecology. Mar. 13, 2003; 31: 175-182.

(Continued)

*Primary Examiner* — Kortney L Klinkel
(74) *Attorney, Agent, or Firm* — Myers Bigel Sibley & Sajovec, P.A.

(57) ABSTRACT

Disclosure is provided for imidazole-phenyl derivative compounds that prevent, remove and/or inhibit the formation of biofilms, compositions comprising these compounds, devices comprising these compounds, and methods of using the same.

3 Claims, No Drawings

(56) References Cited

OTHER PUBLICATIONS

Kelly SR et al. Effects of Caribbean sponge secondary metabolites on bacterial colonization. Aquatic Microbial Ecology. Sep. 6, 2005; 40: 191-203.

Musk Jr. D.J. And Hergenrother P.J. Chemical countermeasures for the control of bacterial biofilms: effective compounds and promising targets. Current Medicinal Chemistry 2006; 13: 2163-2177.

Huigens RW 3rd et al. Inhibition of pseudomonas aeruginosa biofilm formation with bromoageliferin analogues. J. Am. Chem. Soc. 2007; 129: 6966-6967.

Ballard TE et al. Synthesis and antibiofilm activity of a second—generation reverse-amide oroidin library: a structure-activity relationship study. Chemistry. 2008; 14(34): 1074-561.

Huigens RW 3rd et al. Control of bacterial biofilms with marine alkaloid derivatives. Molecular BioSystems. 2008; 4: 614-621.

Richards JJ et al. Inhibition and dispersion of Pseudomonas aeruginosa biofilms with reverse amide 2-aminoimidazole oroidin analogues. Organic & Biomolecular Chemistry. Apr. 21, 2008; 6(8): 1301-1512.

Richards JJ et al. Effects of N-pyrrole substitution on the anti-biofilm activities of oroidin derivatives against *Acinetobacter baumannii*. Bioorganic & Medicinal Chemistry Letters. 2008; 18: 4325-4327.

Richards JJ and Melander C. Synthesis of a 2-aminoimidazole library for antibiofilm screening utilizing the Sonogashira reaction. J. Org. Chem. 2008; 73(13): 5191-5193.

Richards JJ et al. Inhibition and dispersion of proteobacterial biofilms. Chem. Comm. 2008; 1698-1700.

Richards JJ et al. Synthesis and screening of an oroidin library against *Pseudomonas aeruginosa* biofilms. ChemBioChem. 2008; 9: 1267-1279.

Rogers SA and Melander C. Construction and screening of a 2-aminoimidazole library identifies a small molecule capable of inhibiting and dispersing bacterial biofilms across order, class, and phylum. Angew. Chem. Int. Ed. 2008; 47: 5229-5231.

Ballard TE et al. Antibiofilm activity of a diverse oroidin library generated through reductive acylation. J. Org. Chem. 2009; 74(4): 1755-1758.

Huigens RW 3rd et al. Inhibition of *Acinetobacter baumannii*, *Staphylococcus aureus* and *Pseudomonas aeruginosa* biofilm formation with a class of TAGE-triazole conjugates. Org. Biomol. Chem. 2009; 7: 794-802.

Rogers SA et al. Tandem dispersion and killing of bacteria from a biofilm. Organic & Biomolecular Chemistry. 2009; 7: 603-606.

Shore D. College Profile: Dr. John Cavanagh shows that in scientific collaboration—as in a community of molecules—the product is more powerful than the sum of its parts. Perspectives Online. The Magazine of the College of Agriculture and Life Sciences at NC State. North Carolina State University. Summer 2007: 4 pp.

Fishing for seafood safety. Scope. North Carolina State University College of Physical and Mathematical Sciences. Fall 2007: 11.

Galvin F. Marine inspiration for biofilm break up. Chemical Biology. RCS Publishing. Mar. 5, 2008: 2 pp.

Melander C et al. Evaluation of dihydrooroidin as an antifouling additive in marine paint. International Biodeterioration & Biodegradation. 2009; 53: 529-532.

Stokstad E. Sponging away antibiotic resistance. Findings. The Science Magazine News Blog. Feb. 14, 2009: 1 p.

Lydersen K. Scientists learning to target bacteria where they live. washingtonpost.com. The Washington Post. Mar. 9, 2009; A05: 3 pp.

Taking the Resistance out of drug-resistant infections. PhysOrg.com. Apr. 10, 2009: 2 pp.

Avery S. Slime-fighting molecule may rearm antibiotics. newsobserver.com. The News and Observer. Raleigh, NC. Apr. 22, 2009: 2 pp.

International Search Report and Written Opinion, PCT/US09/02101, mailed Jul. 13, 2009.

Ermolat'ev DS and Van Der Eycken EV. A divergent synthesis of substituted 2-aminoimidazoles from 2-aminopyrimidines. Journal of Organic Chemistry. 2008; 73(17): 6691-6697.

Soh CH et al. An efficient and expeditious synthesis of di- and monosubstituted 2-aminoimidazoles. Journal of Combinatorial Chemistry. 2008; 10(1): 118-122.

Ermolat'ev DS et al, Concise and diversity-oriented route toward polysubstituted 2-aminoimidazole alkaloids and their analogues. Angew. Chem. 2010; 122: 9655-9658.

Huigens III RW et al. The chemical synthesis and antibiotic activity of a diverse library of 2-aminobenzimidazole small molecules again MRSA and multidrug-resistant *A. baumannii*. Journal of Medicinal Chemistry. 2011; 54(2):472-484.

Steenackers HPL et al. Structure—activity relationship of 4(5)-aryl-2-amino-1H-imidazoles, N1-substituted 2-aminoimidazoles and imidazo[1,2-a]pyrimidinium salts as inhibitors of biofilm formation by *Salmonella typhimurium* and *Pseudomonas aeruginosa*. Journal of Medicinal Chemistry. 2011; 54(2): 472-484.

Steenackers HPL et al. Structure—activity relationship of 2-hydroxy-2-aryl-1,2,3-dihydro-imidazo[1,2-a]pyrimidinium salts and 2N-substituted 4(5)-aryl-2-amino-1H-imidazoles as inhibitors of biofilm formation by *Salmonella typhirmurium* and *pseudomas aeruginosa*. Bioorganic & Medicinal Chemistry. Jun. 1, 2011; 19(11): 3462-3473 (Abstract only).

Aurora Fine Chemicals Ltd. Search results 4-(4-butylphenyl)-1H-imidazol-2-amine. Retrieved Aug. 19, 2011, 3 pp.

Otava Chemicals. Building Blocks search our compounds by structure on-line. Retrieved Aug. 22, 2011, 2 pp.

International Search Report and Written Opinion, PCT/US09/02446, mailed Aug. 31, 2009.

Casalinuovo IA et al. Fluconazole resistance in *Candida albicans*: a review of mechanisms. European Review for Medical and Pharmacological Sciences. 2004; 8(2): 69-77.

Rogers SA et al. A 2-aminobenzimidazole that inhibits and disperses gram-positive biofilms through a zinc-dependent mechanism. J. Am. Chem. Soc. 2009; 131(29): 9868-9869.

Richards JJ et al. Amide isosteres of oroidin: assessment of antibiofilm activity and *C. elegans* toxicity. Journal of Medicinal Chemistry. 2009; 52(15): 4582-4585.

Richards JJ and Melander C. Controlling bacterial biofilms. ChemBioChem. Epub ahead of print: Aug. 13, 2009; 9 pp.

Reed, Catherine Suzanne. The Design and Synthesis of 2-Aminoimidazole Biofilm Modulators. A thesis submitted to the Graduate Faculty of North Carolina State University in partial fulfillment of the requirements for the Degree of Master of Science. Aug. 4, 2010. 255 pages, Chapter 3, pp. 148-186.

Monnier, V. M., and Cerami, A., "Nonenzymatic browning in vivo: possible process for aging of long-lived proteins", Science 211:491-493 (1981).

Eble et al., "Nonenzymatic glucosylation and glucose-dependent cross-linking of protein", J. Biol. Chem. 258:9406-9412 (1983).

Chang, J. C. F., Ulrich, P. C., Bucala, and Cerami, A., "Detection of an advanced glycosylation product bound to protein in situ", J, Biol. Chem. 260:7970-7974 (1985).

San George, R. C. and Hoberman, H. D., "Reaction of acetaldehyde with hemoglobin", J. Biol, Chem. 261:6811-6821 (1986).

Oimomi, M., Igaki, N., Sakai, M., Ohara, T., Baba, S., and Kato, H., "The effects of aminoguanidine on 3-deoxyglucosone in the Maillard reaction", Agric. Biol. Chem., 53:1727-1728 (1989).

Sell, D. R. and Monnier, V. M., "Structure elucidation of a senescence cross-link from human extracellular matrix", J. Biol. Chem. 264:21597-21602 (1989).

Hayase, F., Nagaraj, R. H., Miyata, S., Njoroge, F.G., and Monnier, V. M., "Aging of proteins: immunological detection of a glucose-derived pyrrole formed during Maillard reaction in vivo", J. Biol. Chem. 263:3758-3764 (1989).

Lo, T. W. C., Westwood, M. E., McLellan, A. C., Selwood, T., and Thornalley, R. J., "Binding and modification of proteins by methylglyoxal under physiological conditions", J. Biol. Chem. 269:32299-32305 (1994).

Vasan, S., Zhang, X., Zhang, X., Kapurniotu, A., Bernhagen, J., Teichberg, S., Basgen, J., Wagle, D., Shih, D., Terlecky, I., Bucala, Cerami, A., Egan, J., and Ulrich, P., "An agent cleaving glucose-derived protein crosslinks in vitro and in vivo", Nature 382:275-278 (1996).

(56) References Cited

OTHER PUBLICATIONS

Nagaraj, R. H., Shipanova, I. N., and Faust, F. M., "Protein cross-linking by the Maillard reaction", J. Biol. Chem. 271:19338-19345 (1996).

Ahmed, M. U., Frye, E,B., Degenhardt, T. P., Thorpe, S. R., and Baynes, J. W., "$N^E$-(Carboxyethyl)lysine, a product of the chemical modification of proteins by methylglyoxal, increases with age in human lens proteins", Biochem. J. 324:565-570 (1997).

Wolffenbuttel, B. H. R., Boulanger, C. M., Crijns, F. R. L., Huijberts, M. S. P., Poitevin, P., Swennen, G. N. M., Vasan, S., Egan, J. J., Ulrich, P., Cerami, A. And Levy, B. I., "Breakers of advanced glycation end products restore large artery properties in experimental diabetes", Proc. Natl. Acad. Sci., USA 95:4630-4634 (1998).

Al-Abed, Y., Mitsuhashi, T., Li, H., Lawson, J. A., Fitzgerald, G. A., Founds, H., Donnelly, T., Cerami, A., Ulrich, P., and Bucala, R., "Inhibition of advanced glycation endproduct formation by acetaldehyde: Role in the cardioprotective effect of ethanol", Proc. Natl. Acad. Sci., USA, 96:2385-2390 (1999).

Paul, R. G., Avery, N. C., Slatter, D. A., Sims, T. J., and Bailey, A. J., "Isolation and characterization of advanced glycation end products derived from the in vitro reaction of ribose and collagen", Biochem., J. 330:1241-1248 (1998).

Ulrich, P. and Cerami, A., "Protein glycation, diabetes, and aging", Endocrine Reviews, 56:1-22 (2001).

Alteon Inc. "Alteon's ALT-711 reduces diabetes-associated cardiac abnormalities", PRNewswire (2003). Retrieved Apr. 30, 2012, 3 pages.

Pyl, T., Lahmer, H., and Beyer, "Over 2-imidazoles and their Phenyihydrazono benzidinartige rearrangement" Chem. Ber., p. 3217-3223 (1961), Abstract only considered.

Hetzheim, A., Peters, O., and Beyer, H., "Uber die Ringumwandlung von 2-amino-3-phenacy1-1,3,4-oxadiazoliumhalogeniden mit Aminen zu 1,2-diamino-imidazol-derivaten", Chem. Ber. 100:3418-3426 (1967), Abstract only considered.

Burtles, R. and Pyman, F. L., "CCLXXII.-2-Amino-4:5-dimethylglyoxaline", J. Chem Soc. [London] 127, 2012 (1925).

Beyer, H., Hetzheim, A., Honack, H., Ling, D. and Ply, T. "Synthesen neuer Imizazol-Derivate", Chem. Ber. 101, 3151-3162 (1968), Abstract only considered.

\* cited by examiner

INHIBITION OF BACTERIAL BIOFILMS WITH IMIDAZOLE-PHENYL DERIVATIVES

RELATED APPLICATIONS

This application claims the benefit under 35 U.S.C. §119(e) of U.S. Application No. 61/042,473, filed Apr. 4, 2008, the disclosure of which is incorporated herein by reference in its entirety. This application is related to U.S. application Ser. No. 12/020,112, filed Jan. 25, 2008, and published Jul. 31, 2008, as publication no. 2008/0181923, the disclosure of which is incorporated herein by reference in its entirety.

FIELD OF THE INVENTION

This invention relates to compounds, compositions and methods useful for controlling biofilms and microorganisms.

BACKGROUND OF THE INVENTION

Biofilms are complex communities of microorganisms that are commonly found on a variety of substrates or surfaces that are moist or submerged (Musk et al., *Curr. Med. Chem.*, 2006, 13, 2163; Donlan et al., *Clin. Microbiol. Rev.*, 2002, 15, 167). Though primarily populated by bacteria, biofilms can also contain many different individual types of microorganisms, e.g., bacteria, archaea, protozoa and algae. The formation of biofilms can be thought of as a developmental process in which a few free-swimming (planktonic) bacteria adhere to a solid surface and, in response to appropriate signals, initiate the formation of a complex sessile microcolony existing as a community of bacteria and other organisms. Bacteria within biofilms are usually embedded within a matrix, which can consist of protein, polysaccharide, nucleic acids, or combinations of these macromolecules. The matrix is a critical feature of the biofilm that protects the inhabiting organisms from antiseptics, microbicides, and host cells. It has been estimated that bacteria within biofilms are upwards of 1,000-fold more resistant to conventional antibiotics (Rasmussen et al., *Int. J. Med. Microbiol.*, 2006, 296, 149).

Biofilms play a significant role in infectious disease. It is estimated that biofilms account for between 50-80% of microbial infections in the body, and that the cost of these infections exceeds $1 billion annually. For example, persistent infections of indwelling medical devices remain a serious problem for patients, because eradication of these infections is virtually impossible. A few diseases in which biofilms have been implicated include endocarditis, otitis media, chronic prostatitis, periodontal disease, chronic urinary tract infections, and cystic fibrosis. The persistence of biofilm populations is linked to their inherent insensitivity to antiseptics, antibiotics, and other antimicrobial compounds or host cells.

Deleterious effects of biofilms are also found in non-medical settings. For example, biofilms are a major problem in the shipping industry. Biofilms form on and promote the corrosion of ship hulls and also increase the roughness of the hulls, increasing the drag on the ships and thereby increasing fuel costs. The biofilms can also promote the attachment of larger living structures, such as barnacles, to the hull. Fuel can account for half of the cost of marine shipping, and the loss in fuel efficiency due to biofilm formation is substantial. One method of controlling biofilms is to simply scrape the films off of the hulls. However, this method is costly and time-consuming, and can promote the spread of troublesome non-native species in shipping waters. Another method involves the use of antifouling coatings containing tin. However, tin-based coatings are now disfavored due to toxicity concerns.

Given the breadth of detrimental effects caused by bacterial biofilms, there has been an effort to develop small molecules that will inhibit their formation (Musk et al., *Curr. Med. Chem.*, 2006, 13, 2163). The underlying principle is that if bacteria can be maintained in the planktonic state, they will either not attach to a target surface and/or they can be killed by a lower dose of microbicide.

Despite the extent of biofilm driven problems, examples of structural scaffolds that inhibit biofilm formation are rare (Musk et al., *Curr. Med. Chem.*, 2006, 13, 2163). The few known examples include the homoserine lactones (Geske et al., *J. Am. Chem. Soc.*, 2005, 127, 12762), which are naturally-occurring bacterial signaling molecules that bacteria use in quorum sensing (Dong et al., *J. Microbiol.*, 2005, 43, 101; Nealson et al., *J. Bacteriol.*, 1970, 104, 313), brominated furanones isolated from the macroalga *Delisea pulchra* (Hentzer et al., *Microbiology-Sgm*, 2002, 148, 87), and ursene triterpenes from the plant *Diospyros dendo* (Hu et al., *J. Nat. Prod.*, 2006, 69, 118).

Bacteria have an unparalleled ability to overcome foreign chemical insult. For example, resistance to vancomycin, "the antibiotic of last resort," has become more prevalent, and strains of vancomycin-resistant *Staphylococcus aureus* have become a serious health risk. It has been predicted that it is simply a matter of time before different bacterial strains develop vancomycin resistance, and the safety net that vancomycin has provided for decades in antibiotic therapy will no longer be available.

Because of their natural resistance to antibiotics, phagocytic cells, and other biocides, biofilms are difficult, if not impossible, to eradicate. Therefore, the identification of compounds that control biofilm formation is of critical need.

SUMMARY OF THE INVENTION

Provided herein are compounds of Formula (I):

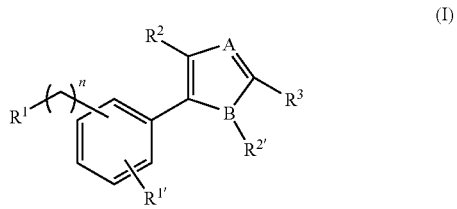

wherein:

$R^1$, $R^{1'}$, $R^2$, $R^{2'}$ and $R^3$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A and B are each independently selected from N, S and O; and n=0 to 20, saturated or unsaturated;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

In some embodiments of Formula (I), $R^1$ is a group:

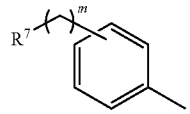

wherein:

$R^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (I), $R^1$ is a group:

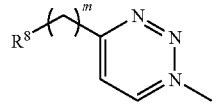

wherein:

$R^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (I), $R^3$ is an amino and A and B are each N, depicted as Formula (I)(a):

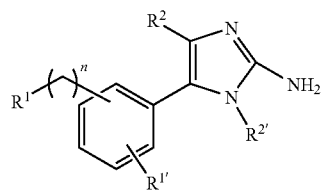

(I)(a)

wherein:

$R^1$, $R^{1'}$, $R^2$ and $R^{2'}$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and n=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

In some embodiments of Formula (I)(a), $R^1$ is a group:

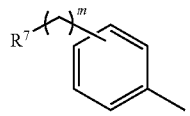

wherein:

$R^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (I)(a), $R^1$ is a group:

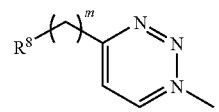

wherein:

$R^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

Also provided are compounds of Formula (II):

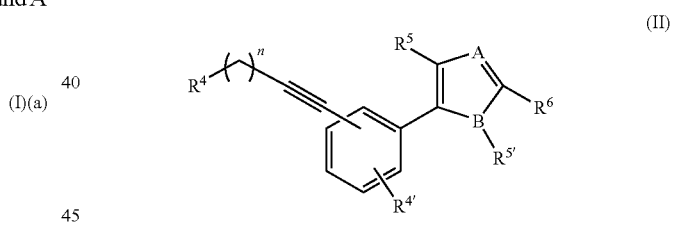

(II)

wherein:

$R^4$, $R^{4'}$, $R^5$, $R^{5'}$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A and B are each independently selected from N, S and O; and n=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

In some embodiments of Formula (II), $R^4$ is a group:

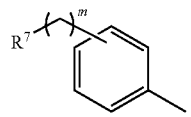

wherein:

$R^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (II), $R^4$ is a group:

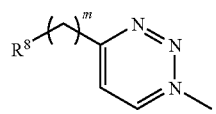

wherein:

$R^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (II), $R^6$ is an amino and A and B are each N, depicted as Formula (II)(a):

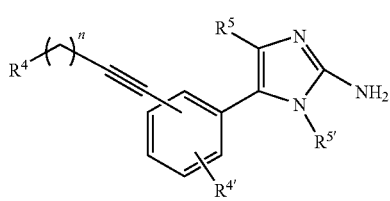

(II)(a)

wherein:

$R^4$, $R^{4'}$, $R^5$ and $R^{5'}$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

In some embodiments of Formula (II)(a), $R^4$ is a group:

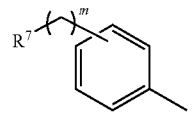

wherein:

$R^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (II)(a), $R^4$ is a group:

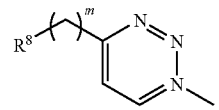

wherein:

$R^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

Further provided are compounds of Formula (III):

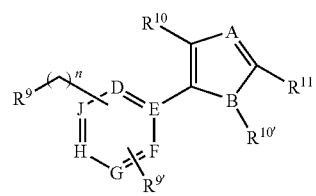

(III)

wherein:

$R^9$, $R^{9'}$, $R^{10}$, $R^{10'}$ and $R^{11}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A and B are each independently selected from N, S and O;

D, E, F, G, H and J are each independently selected from C, N, S and O, wherein at least one of D, E, F, G, H and J is C; and n=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (III), R⁹ is a group:

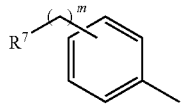

wherein:
R⁷ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and
m=0 to 20, saturated or unsaturated;
or a pharmaceutically acceptable salt or prodrug thereof.

In some embodiments of Formula (III), R⁹ is a group:

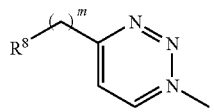

wherein:
R⁸ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and
m=0 to 20, saturated or unsaturated;
or a pharmaceutically acceptable salt or prodrug thereof.

Also provided are compounds of Formula (IV):

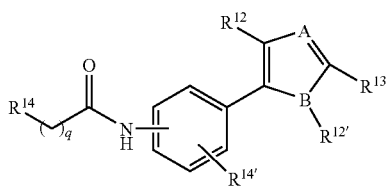

(IV)

wherein:
R¹², R¹²', R¹³, R¹⁴ and R¹⁴' are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;
A and B are each independently selected from N, S and O; and
q=0 to 20, saturated or unsaturated;
or a pharmaceutically acceptable salt or prodrug thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

In some embodiments of Formula (IV), R¹³ is an amino and A and B are each N, depicted as Formula (IV)(a):

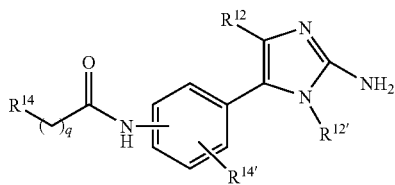

(IV)(a)

wherein:
R¹², R¹²', R¹⁴ and R¹⁴' are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and
q=0 to 20, saturated or unsaturated;
or a pharmaceutically acceptable salt or prodrug thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

Embodiments of Formula (IV)(a) include:

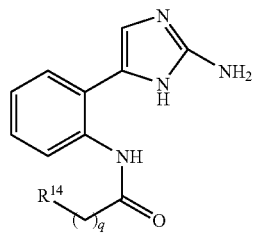

(IV)(a)(1)

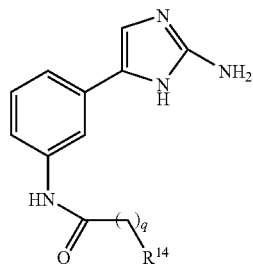

(IV)(a)(2)

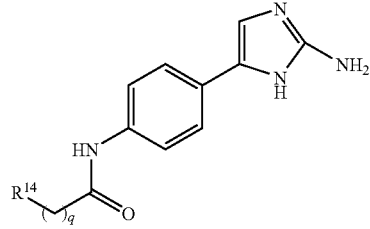

(IV)(a)(3)

wherein:
R¹⁴ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and q=0 to 20, saturated or unsaturated;
or a pharmaceutically acceptable salt or prodrug thereof.

In some embodiments of Formula (IV)(a), $R^{14}$ is a group:

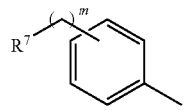

wherein:
$R^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and
m=0 to 20, saturated or unsaturated;
or a pharmaceutically acceptable salt or prodrug thereof.

In some embodiments of Formula (IV)(a), $R^{14}$ is a group:

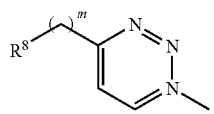

wherein:
$R^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and
m=0 to 20, saturated or unsaturated;
or a pharmaceutically acceptable salt or prodrug thereof.

Further provided are compounds of Formula (V):

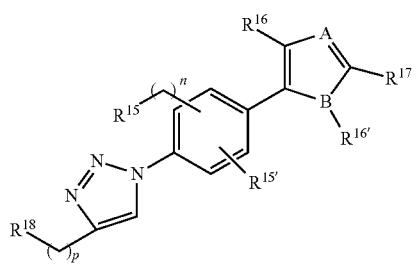

(IV)

wherein:
$R^{15}$, $R^{15'}$, $R^{16}$, $R^{16'}$, $R^{17}$ and $R^{18}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
A and B are each independently selected from N, S and O;
n=0 to 20, saturated or unsaturated; and
p=0 to 20, saturated or unsaturated;
or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

In some embodiments of Formula (V), $R^{18}$ is a group:

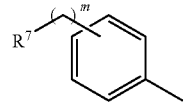

wherein:
$R^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and
m=0 to 20, saturated or unsaturated;
or a pharmaceutically acceptable salt or prodrug thereof.

In some embodiments of Formula (V), $R^{18}$ is a group:

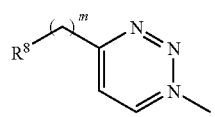

wherein:
$R^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and
m=0 to 20, saturated or unsaturated;
or a pharmaceutically acceptable salt or prodrug thereof.

In some embodiments of Formula (V), $R^{17}$ is an amino and A and B are each N, depicted as Formula (V)(a):

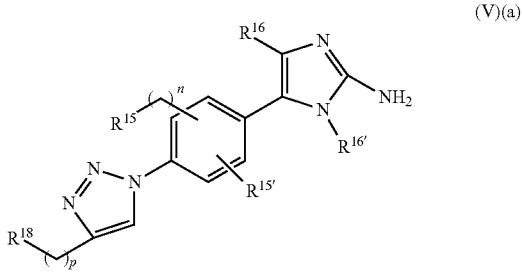

(V)(a)

wherein:
$R^{15}$, $R^{15'}$, $R^{16}$, $R^{16'}$ and $R^{18}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
n=0 to 20, saturated or unsaturated; and
p=0 to 20, saturated or unsaturated;
or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

In some embodiments of Formula (V)(a), $R^{18}$ is a group:

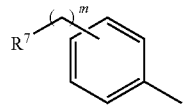

wherein:
$R^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and
m=0 to 20, saturated or unsaturated;
or a pharmaceutically acceptable salt or prodrug thereof.

In some embodiments of Formula (V)(a), $R^{18}$ is a group:

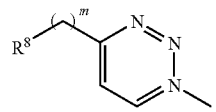

wherein:
$R^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and
m=0 to 20, saturated or unsaturated;
or a pharmaceutically acceptable salt or prodrug thereof.

In some embodiments of Formula (V)(a), n=0 and $R^{15}$ and $R^{15'}$ are each H, depicted as Formula (V)(a)(1):

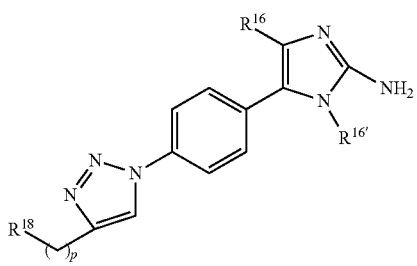

(V)(a)(1)

wherein:
$R^{16}$, $R^{16'}$ and $R^{18}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and
p=0 to 20, saturated or unsaturated;
or a pharmaceutically acceptable salt or prodrug thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

In some embodiments of Formula (V)(a)(1), $R^{18}$ is a group:

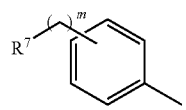

wherein:
$R^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and
m=0 to 20, saturated or unsaturated;
or a pharmaceutically acceptable salt or prodrug thereof.

In some embodiments of Formula (V)(a)(1), $R^{18}$ is a group:

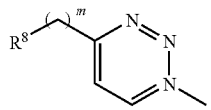

wherein:
$R^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and
m=0 to 20, saturated or unsaturated;
or a pharmaceutically acceptable salt or prodrug thereof.

Biofilm preventing, removing or inhibiting compositions are provided, which include a carrier and an effective amount of a compound disclosed herein. In some embodiments, the composition is a dentifrice composition that promotes dental hygiene by preventing, reducing, inhibiting or removing a biofilm. In some embodiments, the dentifrice composition comprises a toothpaste, mouthwash, chewing gum, dental floss, or dental cream.

Compositions are also provided that include a compound disclosed herein in a pharmaceutically acceptable carrier.

Compositions are further provided that include a compound disclosed herein covalently coupled to a substrate. In some embodiments, the substrate includes a polymeric material. In some embodiments, the substrate includes a solid support. In some embodiments, the substrate includes a drainpipe, glaze ceramic, porcelain, glass, metal, wood, chrome, plastic, vinyl, and Formica® brand laminate (The Diller Corporation, Cincinnati, Ohio). In some embodiments, the substrate includes shower curtains or liners, upholstery, laundry, and carpeting. In some embodiments, the substrate includes a ship hull or a portion thereof. In some embodiments, the substrate includes a food contact surface.

Biofilm preventing, removing or inhibiting coating compositions are provided, including: (a) a film-forming resin; (b) a solvent that disperses said resin; (c) an effective amount of the compounds or compositions disclosed herein, wherein said effective amount prevents or inhibits the growth of a biofilm thereon; and (d) optionally, at least one pigment. In some embodiments, the compound is covalently coupled to the resin. In some embodiments, the resin includes a polymeric material.

Substrates coated with coating composition disclosed herein are also provided. In some embodiments, the substrate includes a polymeric material. In some embodiments, the substrate includes a solid support. In some embodiments, the substrate includes a drainpipe, glaze ceramic, porcelain, glass, metal, wood, chrome, plastic, vinyl, and Formica® brand laminate. In some embodiments, the substrate includes shower curtains or liners, upholstery, laundry, and carpeting. In some embodiments, the substrate includes a ship hull or a portion thereof. In some embodiments, the substrate includes a food contact surface.

Methods of controlling biofilm formation on a substrate are provided, including the step of contacting the substrate with a compound and/or composition disclosed herein in an amount effective to inhibit biofilm formation. In some embodiments, controlling biofilm formation includes clearing a preformed biofilm from said substrate by administering an effective amount of the compound and/or composition disclosed herein to said substrate, wherein said effective amount will reduce the amount of said biofilm on said substrate. In some embodiments, the substrate may include a drainpipe, glaze ceramic, porcelain, glass, metal, wood, chrome, plastic, vinyl, and Formica® brand laminate. In some embodiments, the substrate may include a food product (e.g., seafood). In some embodiments, the biofilm includes Gram-negative bacteria.

Methods for treating and/or preventing a bacterial infection (e.g., chronic bacterial infection) in a subject in need thereof are provided, including administering to said subject a compound and/or composition disclosed herein in an amount effective to inhibit, reduce, or remove a biofilm component of said bacterial infection. The bacterial infection may include urinary tract infection, gastritis, respiratory infection, cystitis, pyelonephritis, osteomyelitis, bacteremia, skin infection, rosacea, acne, chronic wound infection, infectious kidney stones, bacterial endocarditis, and sinus infection.

Also provided are medical devices, including (a) a medical device substrate; and (b) an effective amount of a compound disclosed herein, either coating the substrate, or incorporated into the substrate, wherein said effective amount prevents or inhibits the growth of a biofilm thereon. In some embodiments, the medical device substrate may include stents, fasteners, ports, catheters, scaffolds and grafts. In some embodiments, the compound is covalently coupled to said substrate.

Compounds and/or compositions for use in a method to control a biofilm are further provided. Also provided is the use of compounds and/or compositions disclosed herein for the preparation of a medicament for the treatment and/or prevention of a bacterial infection (e.g., chronic bacterial infection).

DETAILED DESCRIPTION OF THE PREFERRED EMBODIMENTS

The present invention is further described below. All U.S. patent references referred to in this patent application are hereby incorporated by reference in their entirety as if set forth fully herein.

A. Definitions

"Imidazole" refers to the commonly known structure:

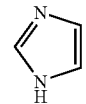

"H" refers to a hydrogen atom. "C" refers to a carbon atom. "N" refers to a nitrogen atom. "O" refers to an oxygen atom. "Halo" refers to F, Cl, Br or I. The term "hydroxy," as used herein, refers to an —OH moiety. "Br" refers to a bromine atom. "Cl" refers to a chlorine atom. "I" refers to an iodine atom. "F" refers to a fluorine atom.

An "acyl group" is intended to mean a —C(O)—R radical, where R is a suitable substituent (for example, an acetyl group, a propionyl group, a butyroyl group, a benzoyl group, or an alkylbenzoyl group).

"Alkyl," as used herein, refers to a straight or branched chain hydrocarbon containing from 1 or 2 to 10 or 20 or more carbon atoms (e.g., C2, C3, C4, C5, C6, C7, C8, C9, C10, C11, C12, C13, C14, C15, etc.). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. In some embodiments, alkyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

The term "optionally substituted" indicates that the specified group is either unsubstituted, or substituted by one or more suitable substituents. A "substituent" is an atom or atoms substituted in place of a hydrogen atom on the parent chain or cycle of an organic molecule, for example, H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Alkenyl," as used herein, refers to a straight or branched chain hydrocarbon containing from 1 or 2 to 10 or 20 or more carbons, and containing at least one carbon-carbon double bond, formed structurally, for example, by the replacement of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. In some embodiments, alkenyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Alkynyl," as used herein, refers to a straight or branched chain hydrocarbon group containing from 1 or 2 to 10 or 20 or more carbon atoms, and containing at least one carbon-carbon triple bond. Representative examples of alkynyl include, but are not limited, to acetylenyl, 1-propynyl, 2-propynyl, 3-butynyl, 2-pentynyl, 1-butynyl and the like. In some embodiments, alkynyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

The term "cycloalkyl," as used herein, refers to a saturated cyclic hydrocarbon group containing from 3 to 8 carbons or more. Representative examples of cycloalkyl include, cyclopropyl, cyclobutyl, cyclopentyl, cyclohexyl, cycloheptyl, and cyclooctyl. In some embodiments, cycloalkyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Heterocyclo," as used herein, refers to a monocyclic or a bicyclic ring system. Monocyclic heterocycle ring systems are exemplified by any 5 or 6 member ring containing 1, 2, 3, or 4 heteroatoms independently selected from the group consisting of: O, N, and S. The 5 member ring has from 0 to 2 double bonds, and the 6 member ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, sulfoxide, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like.

"Aryl" as used herein refers to a fused ring system having one or more aromatic rings. Representative examples of aryl include, azulenyl, indanyl, indenyl, naphthyl, phenyl, tetrahydronaphthyl, and the like. The aryl groups of this invention can be substituted with 1, 2, 3, 4, or 5 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR'R" (wherein, R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl).

"Heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from the group consisting of: O, N, and S. The heteroaryl group, including each heteroatom, can be unsubstituted or substituted with from 1 to 4 suitable substituents, as chemically feasible. For example, the heteroatom S may be substituted with one or two oxo groups, which may be shown as =O.

"Alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like. In some embodiments, alkoxy groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

An "amine" or "amino" group is intended to mean the group —NH$_2$. "Optionally substituted" amines refers to —NH$_2$ groups wherein none, one or two of the hydrogens is replaced by a suitable substituent as described herein, such as alkyl, alkenyl, alkynyl, cycloalkyl, heterocyclo, aryl, heteroaryl, alkoxy, carbonyl, carboxy, etc. In some embodiments, one or two of the hydrogens are optionally substituted with independently selected, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide. Disubstituted amines may have substituents that are bridging, i.e., form a heterocyclic ring structure that includes the amine nitrogen.

An "amide" as used herein refers to an organic functional group having a carbonyl group (C=O) linked to a nitrogen atom (N), or a compound that contains this group, generally depicted as:

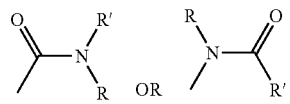

wherein, R and R' can independently be any covalently-linked atom or atoms, for example, H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A "thiol" or "mercapto" refers to an —SH group or to its tautomer =S.

A "sulfone" as used herein refers to a sulfonyl functional group, generally depicted as:

wherein, R can be any covalently-linked atom or atoms, for example, H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A "sulfoxide" as used herein refers to a sulfinyl functional group, generally depicted as:

wherein, R can be any covalently-linked atom or atoms, for example, H, halohydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Triazole" refers to the commonly known structures:

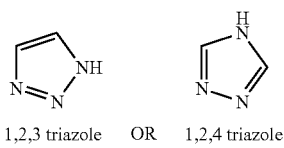

1,2,3 triazole    OR    1,2,4 triazole

The term "oxo," as used herein, refers to a =O moiety. The term "oxy," as used herein, refers to a —O— moiety.

"Nitro" refers to the organic compound functional group —$NO_2$.

"Carbonyl" is a functional group having a carbon atom double-bonded to an oxygen atom (—C=O). "Carboxy" as used herein refers to a —COOH functional group, also written as —(C=O)—OH.

"Amino acid sidechain" as used herein refers to any of the 20 commonly known groups associated with naturally-occurring amino acids, or any natural or synthetic homologue thereof. An "amino acid" includes the sidechain group and the amino group, alpha-carbon atom, and carboxy groups, as commonly described in the art. Examples of amino acids include glycine, and glycine that is substituted with a suitable substituent as described herein, such as alkyl, alkenyl, alkynyl, cycloalkyl, heterocyclo, aryl, heteroaryl, alkoxy, carbonyl, carboxy, etc., or a pharmaceutically acceptable salt or prodrug thereof. For example, "Histidine" is one of the 20 most commonly known amino acids found naturally in proteins. It contains an imidazole side chain substituent. Other examples of naturally-occurring amino acids include lysine, arginine, aspartic acid, glutamic acid, asparagine, glutamine, serine, threonine, tyrosine, alanine, valine, leucine, isoleucine, phenylalanine, methionine, cryptophan, and cysteine. Also included in the definitions of "amino acid sidechain" and "amino acid" is proline, which is commonly included in the definition of an amino acid, but is technically an imino acid. As used in this application, both the naturally-occurring L-, and the non-natural D-amino acid enantiomers are included. A "peptide" is a linear chain of amino acids covalently linked together, typically through an amide linkage, and contains from 1 or 2 to 10 or 20 or more amino acids, and is also optionally substituted and/or branched.

"Boc" or "BOC" is t-butoxycarbonyl, a commonly-known amino protecting group.

A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1, 4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, β-hydroxybutyrates, glycollates, tartrates, methanesulfonates, propanesulfonates, naphthalene-1-sulfonates, naphthalene-2-sulfonates, and mandelates.

A "prodrug" is intended to mean a compound that is converted under physiological conditions or by solvolysis or metabolically to a specified compound that is pharmaceutically active. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein in their entirety.

B. Active Compounds

Active compounds are provided herein that are useful to prevent, remove and/or inhibit the formation of biofilms. In some embodiments, active compounds are derivatives of imidazole. Active compounds as described herein can be prepared as detailed below or in accordance with known procedures or variations thereof that will be apparent to those skilled in the art.

As will be appreciated by those of skill in the art, the active compounds of the various formulas disclosed herein may contain chiral centers, e.g. asymmetric carbon atoms. Thus, the present invention is concerned with the synthesis of both: (i) racemic mixtures of the active compounds, and (ii) enantiomeric forms of the active compounds. The resolution of racemates into enantiomeric forms can be done in accordance with known procedures in the art. For example, the racemate may be converted with an optically active reagent into a diastereomeric pair, and the diastereomeric pair subsequently separated into the enantiomeric forms.

Geometric isomers of double bonds and the like may also be present in the compounds disclosed herein, and all such stable isomers are included within the present invention unless otherwise specified. Also included in active compounds of the invention are tautomers (e.g., tautomers of imidazole) and rotamers.

Active compounds invention include compounds of Formula (I):

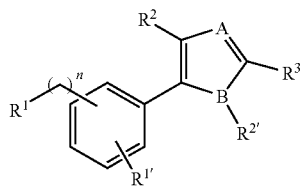
(I)

wherein:

R¹, R¹', R², R²' and R³ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A and B are each independently selected from N, S and O; and n=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

In some embodiments of Formula (I), $R^1$ is a group:

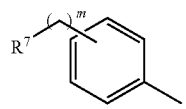

wherein:

$R^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (I), $R^1$ is a group:

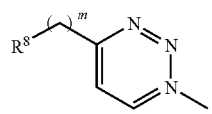

wherein:

$R^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (I), $R^3$ is an amino and A and B are each N, depicted as Formula (I)(a):

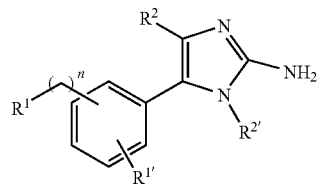
(I)(a)

wherein:

R¹, R¹', R² and R²' are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and n=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

In some embodiments of Formula (I)(a), $R^1$ is a group:

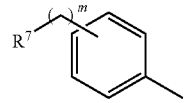

wherein:

$R^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (I)(a), $R^1$ is a group:

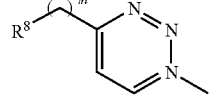

wherein:

$R^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

Active compounds include compounds of Formula (II):

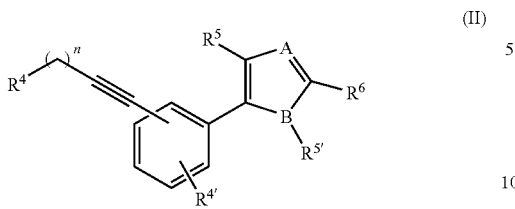

wherein:
$R^4$, $R^{4'}$, $R^5$, $R^{5'}$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A and B are each independently selected from N, S and O; and n=0 to 20, saturated or unsaturated;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

In some embodiments of Formula (II), $R^4$ is a group:

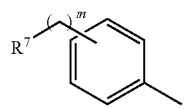

wherein:
$R^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (II), $R^4$ is a group:

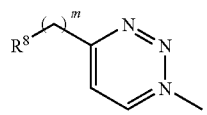

wherein:
$R^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (II), $R^6$ is an amino and A and B are each N, depicted as Formula (II)(a):

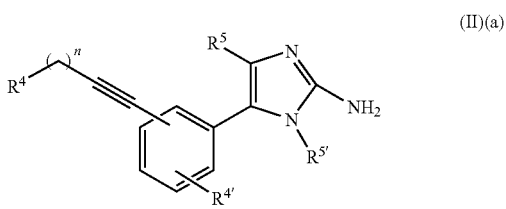

wherein:
$R^4$, $R^{4'}$, $R^5$ and $R^{5'}$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

In some embodiments of Formula (II)(a), $R^4$ is a group:

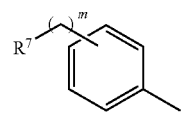

wherein:
$R^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (II)(a), $R^4$ is a group:

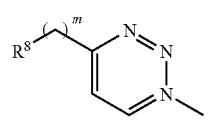

wherein:
$R^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

Active compounds also include compounds of Formula (III):

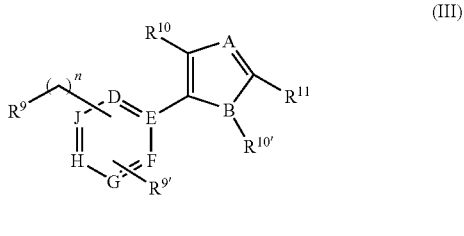

(III)

wherein:

$R^9$, $R^{9'}$, $R^{10}$, $R^{10'}$ and $R^{11}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A and B are each independently selected from N, S and O;

D, E, F, G, H and J are each independently selected from C, N, S and O, wherein at least one of D, E, F, G, H and J is C; and n=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (III), $R^9$ is a group:

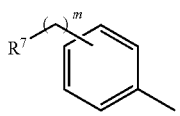

wherein:

$R^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (III), $R^9$ is a group:

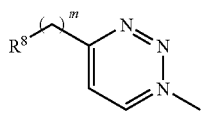

wherein:

$R^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

Active compounds include those of Formula (IV):

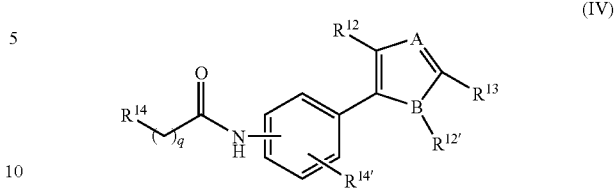

(IV)

wherein:

$R^{12}$, $R^{12'}$, $R^{13}$, $R^{14}$ and $R^{14'}$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

A and B are each independently selected from N, S and O; and q=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

In some embodiments of Formula (IV), $R^{13}$ is an amino and A and B are each N, depicted as Formula (IV)(a):

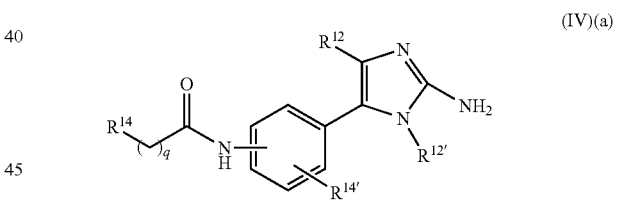

(IV)(a)

wherein:

$R^{12}$, $R^{12'}$, $R^{14}$ and $R^{14'}$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and q=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

Embodiments of Formula (IV)(a) include:

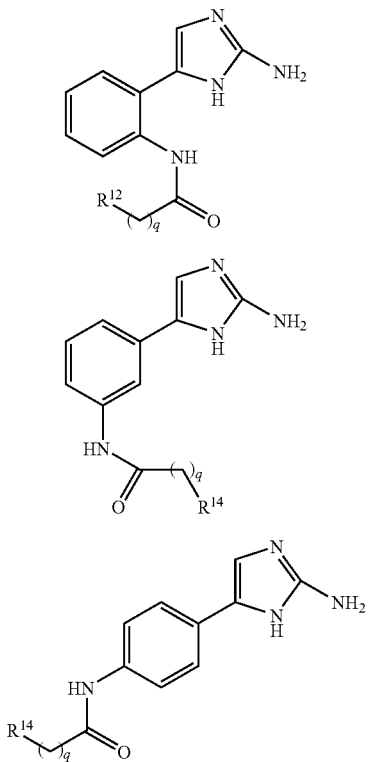

wherein:
R$^{14}$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and
q=0 to 20, saturated or unsaturated;
or a pharmaceutically acceptable salt or prodrug thereof.
In some embodiments of Formula (IV)(a), R$^{14}$ is a group:

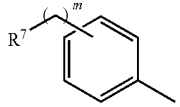

wherein:
R$^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and
m=0 to 20, saturated or unsaturated;
or a pharmaceutically acceptable salt or prodrug thereof.
In some embodiments of Formula (IV)(a), R$^{14}$ is a group:

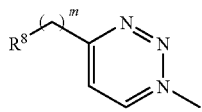

wherein:
R$^8$ is selected from the group consisting of: H, hydroxy, acyl, alkyl, alkenyl, alkynyl, cycloalkyl, heteroaryl, alkoxy, amino, amide, sulfone, sulfoxide, oxo, oxy, nitro, carbonyl, carboxy, amino acid sidechain, amino acid and peptide; and
m=0 to 20, saturated or unsaturated;
or a pharmaceutically acceptable salt or prodrug thereof.

Active compounds invention include compounds of Formula (V):

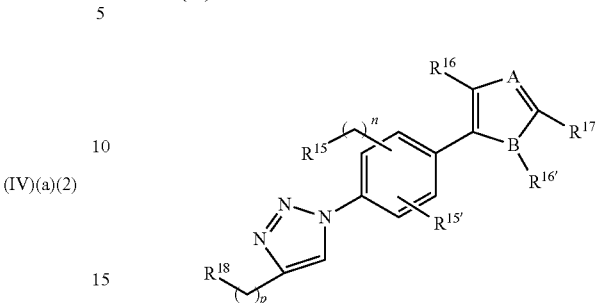

wherein:
R$^{15}$R$^{15'}$, R$^{16}$, R$^{16'}$, R$^{17}$ and R$^{18}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
A and B are each independently selected from N, S and O;
n=0 to 20, saturated or unsaturated; and
p=0 to 20, saturated or unsaturated;
or a pharmaceutically acceptable salt or prodrug thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.
In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.
In some embodiments of Formula (V), R$^{18}$ is a group:

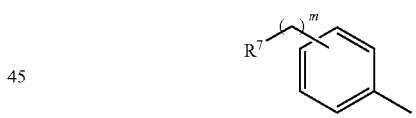

wherein:
R$^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and
m=0 to 20, saturated or unsaturated;
or a pharmaceutically acceptable salt or prodrug thereof.
In some embodiments of Formula (V), R$^{18}$ is a group:

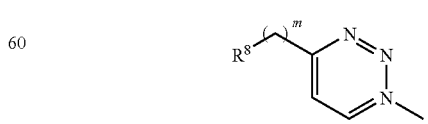

wherein:
R$^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (V), $R^{17}$ is an amino and A and B are each N, depicted as Formula (V)(a):

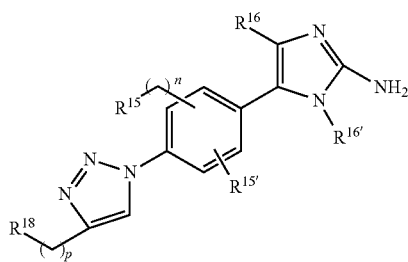

wherein:

$R^{15}$, $R^{15'}$, $R^{16}$, $R^{16'}$ and $R^{18}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20, saturated or unsaturated; and p=0 to 20, saturated or unsaturated;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

In some embodiments of Formula (V)(a), $R^{18}$ is a group:

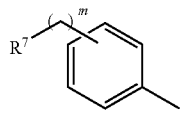

wherein:

$R^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (V)(a), $R^{18}$ is a group:

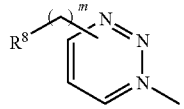

wherein:

$R^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (V)(a), n=0 and $R^{15}$ and $R^{15'}$ are each H, depicted as Formula (V)(a)(1):

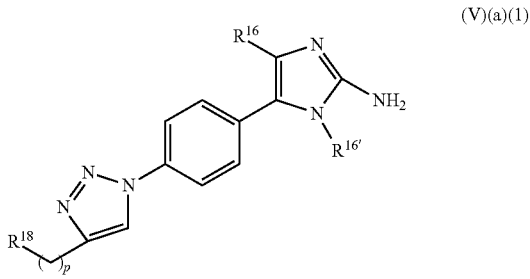

wherein:

$R^{16}$, $R^{16'}$ and $R^{18}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and p=0 to 20, saturated or unsaturated;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, one, two or three of the carbon atoms in the phenyl moiety is replaced by a suitable heteroatom, e.g., with a nitrogen (e.g., pyridine, pyrimidine, pyrazine, etc., heterocycles), oxygen, sulfur, etc.

In some embodiments of Formula (V)(a)(1), $R^{18}$ is a group:

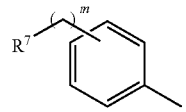

wherein:

$R^7$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

In some embodiments of Formula (V)(a)(1), $R^{18}$ is a group:

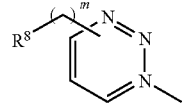

wherein:

$R^8$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and m=0 to 20, saturated or unsaturated;

or a pharmaceutically acceptable salt or prodrug thereof.

C. Compositions

In some embodiments, biofilm preventing, removing or inhibiting compositions are provided, comprising a carrier and an effective amount of active compound. "Biofilm" or "biofilms" refer to communities of microorganisms that are attached to a substrate. The microorganisms often excrete a protective and adhesive matrix of polymeric compounds. They often have structural heterogeneity, genetic diversity, and complex community interactions. "Biofilm preventing", "biofilm removing", "biofilm inhibiting", "biofilm reducing", "biofilm resistant", "biofilm controlling" or "antifouling" refer to prevention of biofilm formation, inhibition of the establishment or growth of a biofilm, or decrease in the amount of organisms that attach and/or grow upon a substrate, up to and including the complete removal of the biofilm. As used herein, a "substrate" can include any living or nonliving structure. For example, biofilms often grow on synthetic materials submerged in an aqueous solution or exposed to humid air, but they also can form as floating mats on a liquid surface, in which case the microorganisms are adhering to each other or to the adhesive matrix characteristic of a biofilm. An "effective amount" of a biofilm preventing, removing or inhibiting composition is that amount which is necessary to carry out the composition's function of preventing, removing or inhibiting a biofilm.

In some embodiments, the carrier is a pharmaceutically acceptable carrier. A "pharmaceutically acceptable carrier" as used herein refers to a carrier that, when combined with an active compound of the present invention, facilitates the application or administration of that active compound for its intended purpose to prevent or inhibit biofilm formation, or remove an existing biofilm. The active compounds may be formulated for administration in a pharmaceutically acceptable carrier in accordance with known techniques. See, e.g., Remington, *The Science And Practice of Pharmacy* (9$^{th}$ Ed. 1995). The pharmaceutically acceptable carrier must, of course, also be acceptable in the sense of being compatible with any other ingredients in the composition. The carrier may be a solid or a liquid, or both, and is preferably formulated with the compound as a unit-dose composition, for example, a tablet, which may contain from 0.01 or 0.5% to 95% or 99% by weight of the active compound. One or more active compounds may be included in the compositions of the invention, which may be prepared by any of the well-known techniques of pharmacy comprising admixing the components, optionally including one or more accessory ingredients.

In general, compositions may be prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

The compositions of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound that is being used. Preferred routes of parenteral administration include intrathecal injection and intraventricular injection into a ventricle of the brain.

Compositions suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such compositions may be prepared by any suitable method of pharmacy, which includes the step of bringing into association the active compound and a suitable carrier (which may contain one or more accessory ingredients as noted above).

Compositions suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Compositions of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes that render the composition isotonic with the blood of the intended recipient. Aqueous and non-aqueous sterile suspensions may include suspending agents and thickening agents. The compositions may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

For example, in one aspect of the present invention, there is provided an injectable, stable, sterile composition comprising a compound of Formula (I), Formula (II), Formula (III), Formula (IV), Formula (V), or a salt or prodrug thereof, in a unit dosage form in a sealed container. The compound or salt is provided in the form of a lyophilizate that is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent that is physiologically acceptable may be employed in sufficient quantity to emulsify the compound or salt in an aqueous carrier. One such useful emulsifying agent is phosphatidyl choline.

Compositions suitable for rectal administration are preferably presented as unit dose suppositories. These may be prepared by mixing the active compound with one or more conventional solid carriers, for example, cocoa butter, and then shaping the resulting mixture.

Compositions suitable for topical application to the skin preferably take the form of an ointment, cream, lotion, paste, gel, spray, aerosol, or oil. Carriers that may be used include petroleum jelly, lanoline, polyethylene glycols, alcohols, transdermal enhancers, and combinations of two or more thereof.

Compositions suitable for transdermal administration may be presented as discrete patches adapted to remain in intimate contact with the epidermis of the recipient for a prolonged period of time. Compositions suitable for transdermal administration may also be delivered by iontophoresis (see, for example, *Pharmaceutical Research* 3 (6):318 (1986)) and typically take the form of an optionally buffered aqueous solution of the active compound.

Also provided in some embodiments are compositions comprising an active compound and a biocide. A "biocide" as used herein refers to a substance with the ability to kill or to inhibit the growth of microorganisms (e.g., bacteria, fungal cells, protozoa, etc.), which substance is not an active compound give above in Section B. Common biocides include oxidizing and non-oxidizing chemicals. Examples of oxidizing biocides include chlorine, chlorine dioxide, and ozone. Examples of non-oxidizing biocides include quaternary ammonium compounds, formaldehyde, and anionic and non-anionic surface agents. Chlorine is the most common biocide used in sanitizing water systems.

An "antibiotic" as used herein is a type of "biocide." Common antibiotics include aminoglycosides, carbacephems (e.g., loracarbef), carbapenems, cephalosporins, glycopeptides (e.g., teicoplanin and vancomycin), macrolides, monobactams (e.g., aztreonam) penicillins, polypeptides (e.g., bacitracin, colistin, polymyxin B), quinolones, sulfonamides, tetracyclines, etc. Antibiotics treat infections by either killing or preventing the growth of microorganisms. Many act to inhibit cell wall synthesis or other vital protein synthesis of the microorganisms.

Aminoglycosides are commonly used to treat infections caused by Gram-negative bacteria such as *Escherichia coli* and *Klebsiella*, particularly *Pseudomonas aeroginosa*. Examples of aminoglycosides include, but are not limited to, amikacin, gentamicin, kanamycin, neomycin, netilmicin, streptomycin, tobramycin, and paromomycin.

Carbapenems are broad-specrum antibiotics, and include, but are not limited to, ertapenem, doripenem, imipenem/cilstatin, and meropenem.

Cephalosporins include, but are not limited to, cefadroxil, cefazolin, cefalotin (cefalothin), cefalexin, cefaclor, cefamandole, cefoxitin, cefprozil, loracarbef, cefuroxime, cefixime, cefdinir, cefditoren, cefoperazone, cefotaxime, cefpodoxime, ceftazidime, ceftibuten, ceftizoxime, ceftriaxone, cefepime, cefpirome, and ceftobiprole.

Macrolides include, but are not limited to, azithromycin, clarithromycin, dirithromycin, erythromycin, roxithromycin, troleandomycin, telithromycin and spectinomycin.

Penicillins include, but are not limited to, amoxicillin, ampicillin, azlocillin, bacampicillin, carbenicillin, cloxacillin, dicloxacillin, flucloxacillin, mezlocillin, meticillin, nafcillin, oxacillin, penicillin, piperacillin and ticarcillin.

Quinolones include, but are not limited to, ciprofloxacin, enoxacin, gatifloxacin, gemifloxacin, levofloxacin, lomefloxacin, moxifloxacin, norfloxacin, ofloxacin and trovafloxacin.

Sulfonamides include, but are not limited to, mafenide, prontosil, sulfacetamide, sulfamethizole, sulfanilamide, sulfasalazine, sulfisoxazole, trimethoprim, and co-trimoxazole (trimethoprim-sulfamethoxazole).

Tetracyclines include, but are not limited to, demeclocycline, doxycycline, minocycline, oxytetracycline and tetracycline.

Other antibiotics include arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin (rifampicin), tinidazole, etc.

In some embodiments, a dentifrice composition is provided comprising the active compounds. A "dentifrice" is a substance that is used to clean the teeth. It may be in the form of, e.g., a paste or powder. Commonly known dentifrices include toothpaste, mouthwash, chewing gum, dental floss, and dental cream. Other examples of dentifrices include toothpowder, mouth detergent, troches, dental or gingival massage cream, dental strips, dental gels, and gargle tablets. Examples of dentifrice compositions comprising toothpaste and mouthwash are found in U.S. Pat. No. 6,861,048 (Yu et al.); U.S. Pat. No. 6,231,836 (Takhtalian et al.); and U.S. Pat. No. 6,331,291 (Glace et al.); each incorporated by reference herein in their entirety.

A coating composition is also provided. A "coating" as used herein is generally known. Any of a variety of organic and aqueous coating compositions, with or without pigments, may be modified to contain biofilm inhibiting compositions as described herein, including but not limited to those described in U.S. Pat. Nos. 7,109,262, 6,964,989, 6,835,459, 6,677,035, 6,528,580, 6,235,812, etc., each incorporated by reference herein in their entirety.

In general, the coatings comprise a film-forming resin, an aqueous or organic solvent that disperses the resin; and, optionally, at least one pigment. Other ingredients such as colorants, secondary pigments, stabilizers and the like can be included if desired. However, for use in the present invention the compositions further comprise one or more biofilm inhibiting compounds as described herein, which may be carried by or dispersed in the solvent and/or resin, so that the biofilm inhibiting compounds are dispersed or distributed on the substrate an article coated. A resin may carry the biofilm inhibiting compounds through covalent attachment through means well known in the art. The resin may comprise, for example, a polymeric material. A polymeric material is a material that is comprised of large molecules made from associated smaller repeating structural units, often covalently linked. Common examples of polymeric materials are unsaturated polyester resins, and epoxy resins.

Any suitable article can be coated, in whole or in part, with a composition of the invention. Suitable articles include, but are not limited to, automobiles and airplanes (including substrates such as wing and propeller surfaces for aerodynamic testing), vessel hulls (including interior and exterior surfaces thereof), pressure vessels (including interior and exterior surfaces thereof) medical implants, windmills, etc. Coating of the article with the composition can be carried out by any suitable means, such as by brushing, spraying, electrostatic deposition, dip coating, doctor blading, etc.

D. Methods of Use

Methods of controlling biofilm formation on a substrate are disclosed, comprising the step of administering an active compound to a substrate in an amount effective to inhibit biofilm formation. A "substrate" as used herein is a base on which an organism, such as those commonly found in biofilms, may live. The term "substrate," as used herein, refers to any substrate, whether in an industrial or a medical setting, that provides or can provide an interface between an object and a fluid, permitting at least intermittent contact between the object and the fluid. A substrate, as understood herein, further provides a plane whose mechanical structure, without further treatment, is compatible with the adherence of microorganisms. Substrates compatible with biofilm formation may be natural or synthetic, and may be smooth or irregular. Fluids contacting the substrates can be stagnant or flowing, and can flow intermittently or continuously, with laminar or turbulent or mixed flows. A substrate upon which a biofilm forms can be dry at times with sporadic fluid contact, or can have any degree of fluid exposure including total immersion. Fluid contact with the substrate can take place via aerosols or other means for air-borne fluid transmission.

Biofilm formation with health implications can involve those substrates in all health-related environments, including substrates found in medical environments and those substrates in industrial or residential environments that are involved in those functions essential to human well being, for example, nutrition, sanitation and the prevention of disease. Substrates found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like. Other examples will be readily apparent to practitioners in these arts. Substrates found in the medical environment also include the inner and outer aspects of pieces of medical equipment, medical gear worn or carried by personnel in the health care setting. Such substrates can include counter tops and fixtures in areas used for medical procedures or for preparing medical apparatus, tubes and canisters used in respiratory treatments, including the administration of oxygen, of solubilized drugs in nebulizers and of anesthetic agents. Also included are those substrates intended as biological barriers to infectious organisms in medical settings, such as gloves, aprons and faceshields. Commonly used materials for biological barriers may be latex-based or non-latex based. Vinyl is commonly used as a material for non-latex surgical gloves. Other such substrates can include handles and cables for medical or dental equipment not intended to be sterile. Additionally, such substrates can include those non-sterile external substrates of tubes and other apparatus found in areas where blood or body fluids or other hazardous biomaterials are commonly encountered.

Substrates in contact with liquids are particularly prone to biofilm formation. As an example, those reservoirs and tubes used for delivering humidified oxygen to patients can bear biofilms inhabited by infectious agents. Dental unit waterlines similarly can bear biofilms on their substrates, providing a reservoir for continuing contamination of the system of flowing an aerosolized water used in dentistry. Sprays, aerosols and nebulizers are highly effective in disseminating biofilm fragments to a potential host or to another environmental site. It is especially important to health to prevent biofilm formation on those substrates from where biofilm fragments can be carried away by sprays, aerosols or nebulizers contacting the substrate.

Other substrates related to health include the inner and outer aspects of those articles involved in water purification, water storage and water delivery, and articles involved in food processing. Substrates related to health can also include the inner and outer aspects of those household articles involved in providing for nutrition, sanitation or disease prevention. Examples can include food processing equipment for home use, materials for infant care, tampons and toilet bowls. "Substrate" as used herein also refers to a living substrate, such as the inner ear of a patent.

Substrates can be smooth or porous, soft or hard. Substrates can include a drainpipe, glaze ceramic, porcelain, glass, metal, wood, chrome, plastic, vinyl, Formica® brand laminate, or any other material that may regularly come in contact with an aqueous solution in which biofilms may form and grow. The substrate can be a substrate commonly found on household items such as shower curtains or liners, upholstery, laundry, and carpeting.

A substrate on which biofilm preventing, removing or inhibiting is important is that of a ship hull. Biofilms, such as those of *Halomonas pacifica*, promote the corrosion of the hull of ships and also increase the roughness of the hull, increasing the drag on the ship and thereby increasing fuel costs. The biofilm can also promote the attachment of larger living structures such as barnacles on the ship hull. Fuel can account for half of the cost of marine shipping, and the loss in fuel efficiency due to biofilm formation is substantial.

Substrates on which biofilms can adhere include those of living organisms, as in the case of humans with chronic infections caused by biofilms, as discussed above. Biofilms can also form on the substrates of food contact surfaces, such as those used for processing seafood, and also on food products themselves. Examples of seafood products that may have biofilm contamination include oysters. Human infections caused by the ingestion of raw oysters has been linked to *Vibrio vulnificus* bacterium. *Vibrio* bacteria attach to algae and plankton in the water and transfer to the oysters and fish that feed on these organisms.

Other examples of substrates or devices on which biofilms can adhere can be found in U.S. Pat. Nos. 5,814,668 and 7,087,661; and U.S. Pat. Application Publication Nos. 2006/0228384 and 2006/0018945, each of which is incorporated herein by reference in its entirety.

In some embodiments, methods of enhancing the effects of a biocide are disclosed, comprising the step of administering an active compound in combination with a biocide, the active compound being administered in an amount effective to enhance the effects of the biocide.

"Administering" or "administration of" an active compound and/or biocide as used herein in inclusive of contacting, applying, etc. (e.g., contacting with an aqueous solution, contacting with a surface (e.g., a hospital surface such as a table, instrumentation, etc.)), in addition to providing to a subject (for example, to a human subject in need of treatment for a microbial infection).

"Enhancing" the effects of a biocide by administering an active compound in combination with the biocide refers to increasing the effectiveness of the biocide, such that the microorganism killing and/or growth inhibition is higher at a certain concentration of the biocide administered in combination with the active compound than without. In some embodiments, a bacteria or other microorganism is "sensitized" to the effects of a biocide, such that the bacteria or other microorganism that was resistant to the biocide prior to administering the active compound (e.g., little to none, or less than 20, 10, 5 or 1% are killed upon application) is rendered vulnerable to that biocide upon or after administering the active compound (e.g., greater than 20, 30, 40, 50, 60, 70, 80, 90, or 95% or more are killed).

As used herein, the administration of two or more compounds (inclusive of active compounds and biocides) "in combination" means that the two compounds are administered closely enough in time that the administration of or presence of one alters the biological effects of the other. The two compounds may be administered simultaneously (concurrently) or sequentially.

Simultaneous administration of the compounds may be carried out by mixing the compounds prior to administration, or by administering the compounds at the same point in time but at different anatomic sites or using different routes of administration, or administered at times sufficiently close that the results observed are indistinguishable from those achieved when the compounds are administered at the same point in time.

Sequential administration of the compounds may be carried out by administering, e.g., an active compound at some point in time prior to administration of a biocide, such that the prior administration of active compound enhances the effects of the biocide (e.g., percentage of microorganisms killed and/or slowing the growth of microorganisms). In some embodiments, an active compound is administered at some point in time prior to the initial administration of a biocide. Alternatively, the biocide may be administered at some point in time prior to the administration of an active compound, and optionally, administered again at some point in time after the administration of an active compound.

Also disclosed is a method of controlling biofilm formation wherein the biofilm comprises Gram-negative bacteria. "Gram-negative" bacteria are those that do not retain crystal violet dye after an alcohol wash in the Gram staining protocol. This is due to structural properties in the cell walls of the bacteria. Many genera and species of Gram-negative bacteria are pathogenic. Gram-negative bacteria include members of the phylum proteobacteria, which include genus members *Escherichia, Salmonella, Vibrio*, and *Helicobacter*. A "genus" is a category of biological classification ranking between the family and the species, comprising structurally or phylogenetically related species, or an isolated species exhibiting unusual differentiation. It is usually designated by a Latin or latinized capitalized singular noun. Examples of genera of biofilm-forming bacteria affected by active compounds of this invention include, but are not limited to, *Pseudomonas, Bordetella, Vibrio, Haemophilus, Halomonas*, and *Acinetobacter*. "Species" refer to a category of biological classification ranking below the genus, and comprise members that are structurally or phylogenetically related, or an isolated member exhibiting unusual differentiation. Species are commonly designated by a two-part name, which name includes the capitalized and italicized name of the genus in which the species belongs as the first word in the name, followed by the second word that more specifically identifies the member of the genus, which is not capitalized. Examples of species of bacteria capable of forming biofilms that are affected by active compounds of the present invention include *Pseudomonas aeuroginosa, Bordetella pertussis, Vibrio vulnificus, Haemophilus influenzae, Halomonas pacifica*, and *Acinetobacter baumannii*.

Other examples of Gram-negative bacteria affected by active compounds of the present invention include, but are not limited to, bacteria of the genera *Klebsiella, Proteus, Neisseria, Helicobacter, Brucella, Legionella, Campylobacter, Francisella, Pasteurella, Yersinia, Bartonella, Bacteroides, Streptobacillus, Spirillum, Moraxella* and *Shigella*.

Examples of Gram-positive bacteria affected by active compounds of the present invention include, but are not limited to, bacteria of the genera *Listeria Staphylococcus., Streptococcus, Bacillus, Corynebacterium, Peptostreptococcus*, and *Clostridium*. Furthermore, bacteria affected by active compounds of the present invention includes Gram-positive bacteria including, but not limited to, *Listeria monocytogenes, Staphylococcus aureus, Streptococcus pyogenes, Streptococcus pneumoniae, Bacillus cereus, Bacillus anthracis, Clostridium botulinum, Clostridium perfringens, Clostridium difficile, Clostridium tetani, Corynebacterium diphtheriae, Corynebacteruim ulcerans*, and *Peptostreptococcus anaerobius*. Additional bacteria affected by active compounds of the present invention also include bacterial genera including, but not limited to, *Actinomyces, Propionibacterium, Nocardia* and *Streptomyces*.

"Planktonic" bacteria are bacteria that are free-swimming in a fluid, as opposed to attached to a surface (such as in a biofilm).

Various nosocomial infections that are especially prevalent in intensive care units implicate *Acinetobacter* species such as *Acinetobacter baumannii* and *Acinetobacter Iwoffi*. *Acinetobacter baumanni* is a frequent cause of nosocomial pneumonia, and can also cause skin and wound infections and bacteremia. *Acinetobacter Iwoffi* causes meningitis. The *Acinetobacter* species are resistant to many classes of antibiotics. The CDC has reported that bloodstream infections implicating *Acinetobacter baumanni* were becoming more prevalent among service members injured during the military action in Iraq and Afghanistan.

*Staphylococcus aureus* is a common cause of nosocomial infections, often found in post-surgical wound infections. *Staphylococcus aureus* can also cause variety of other infections in humans (e.g., skin infections), as well as contribute to mastitis in dairy cows. Methicillin-resistant *Staphylococcus aureus* (MRSA), in particular, is especially difficult to treat due to multiple drug resistances, including penicillins and cephalosporins. MRSA has become problematic in hospital settings, particularly among the more susceptible patients with open wounds, invasice devices, weakened immune systems, etc.

A "fungal cell" as used herein may be any fungal cell belonging to the genera including, but not limited to, *Aspergillus, Candida, Cryptococcus, Coccidioides, Tinea, Sporothrix, Blastomyces, Histoplasma, Pneumocystis* and *Saccharomyces*. Additionally, fungus includes, but is not limited to, *Aspergillus fumigatus, Aspergillus flavus, Aspergillus niger, Aspergillus terreus, Aspergillus nidulans, Candida albicans, Coccidioides immitis, Cryptococcus neoformans, Tinea unguium, Tinea corporis, Tinea cruris, Sporothrix schenckii, Blastomyces dermatitidis, Histoplasma capsulatum, Histoplasma duboisii*, and *Saccharomyces cerevisiae*.

"Protazoa" are unicellular eukaryotic microorganisms, and include flagellates, amoeboids, sporozoans, ciliates, etc.

A method for treating a chronic bacterial infection in a subject in need thereof is disclosed, comprising administering active compound to said subject in an amount effective to inhibit, reduce, or remove a biofilm component of said chronic bacterial infection. "Treating" as used herein refers to any type of activity that imparts a benefit to a patient afflicted with a disease, including improvement in the condition of the patient (e.g., in one or more symptoms), delay in the progression of the disease, delay in onset of the disease, etc. The present invention is primarily concerned with the treatment of human subjects, but the invention may also be carried out on animal subjects, particularly mammalian subjects (e.g., mice, rats, dogs, cats, rabbits, and horses), avian subjects (e.g., parrots, geese, quail, pheasant), livestock (e.g., pigs, sheep, goats, cows, chickens, turkey, duck, ostrich, emu), reptile and amphibian subjects, for veterinary purposes or animal husbandry, and for drug screening and drug development purposes.

A "chronic bacterial infection" is a bacterial infection that is of a long duration or frequent recurrence. For example, a chronic middle ear infection, or otitis media, can occur when the Eustachian tube becomes blocked repeatedly due to allergies, multiple infections, ear trauma, or swelling of the adenoids. The definition of "long duration" will depend upon the particular infection. For example, in the case of a chronic middle ear infection, it may last for weeks to months. Other known chronic bacterial infections include urinary tract infection (most commonly caused by *Escherichia coli* and/or *Staphylococcus saprophyticus*), gastritis (most commonly caused by *Helicobacter pylori*), respiratory infection (such as those commonly afflicting patents with cystic fibrosis, most commonly caused by *Pseudomonas aeuroginosa*), cystitis (most commonly caused by *Escherichia coli*), pyelonephritis (most commonly caused by *Proteus* species, *Escherichia coli* and/or *Pseudomonas* species), osteomyelitis (most commonly caused by *Staphylococcus aureus*, but also by *Escherichia coli*), bacteremia, skin infection, rosacea, acne, chronic wound infection, infectious kidney stones (can be caused by *Proteus mirabilis*), bacterial endocarditis, and sinus infection. A common infection afflicting pigs is atrophic rhinitis (caused by *Bordatella* species, e.g. *Bordatella rhinitis*).

Also disclosed is a method of clearing a preformed biofilm from a substrate comprising the step of administering an effective amount of compound to said substrate, wherein said effective amount will reduce the amount of said biofilm on said substrate. "Preformed biofilm" is a biofilm that has begun to adhere to a substrate. The biofilm may or may not yet be fully formed.

E. Devices

Medical devices comprising a substrate and an effective amount of active compound are also disclosed. "Medical device" as used herein refers to an object that is inserted or implanted in a subject or applied to a surface of a subject. Common examples of medical devices include stents, fasteners, ports, catheters, scaffolds and grafts. A "medical device substrate" can be made of a variety of biocompatible materials, including, but not limited to, metals, ceramics, polymers, gels, and fluids not normally found within the human body. Examples of polymers useful in fabricating medical devices include such polymers as silicones, rubbers, latex, plastics, polyanhydrides, polyesters, polyorthoesters, polyamides, polyacrylonitrile, polyurethanes, polyethylene, polytetrafluoroethylene, polyethylenetetraphthalate, etc. Medical devices can also be fabricated using naturally-occurring materials or treated with naturally-occurring materials. Medical devices can include any combination of artificial materials, e.g., combinations selected because of the particular characteristics of the components. Medical devices can be intended for short-term or long-term residence where they are positioned. A hip implant is intended for several decades of use, for example. By contrast, a tissue expander may only be needed for a few months, and is removed thereafter.

Some examples of medical devices are found in U.S. Pat. No. 7,081,133 (Chinn et al.); U.S. Pat. No. 6,562,295 (Neuberger); and U.S. Pat. No. 6,387,363 (Gruskin); each incorporated by reference herein in their entirety.

F. Covalent Coupling of Active Compounds

Active compounds as described herein can be covalently coupled to substrates. Examples of substrates include solid supports and polymers. The polymers, typically organic polymers, may be in solid form, liquid form, dispersed or solubilized in a solvent (e.g., to form a coating composition as described above), etc. The solid support may include the substrate examples as described above to be coated with or treated with active compounds of the invention.

Covalent coupling can be carried out by any suitable technique. Active compounds of the present invention may be appended to a substrate via aldehyde condensation, amide or peptide bond, carbon-carbon bond, or any suitable technique commonly used in the art.

Various coupling reactions can be used to covalently link active compounds of the present invention to a substrate. Examples of coupling reactions that can be used include, but are not limited to, Hiyama, Suzuki, Sonogashira, Heck, Stille, Negishi, Kumada, Wurtz, Ullmann, Cadiot-Chodkiewicz, Buchwald-Hartwig, and Grignard reactions. For example, an active compound of Formula (I), Formula (II), Formula (III), Formula (IV) or Formula (V) that is substituted with a halo (e.g. bromo or chloro) can be coupled to a substrate via a Heck reaction.

This listing of examples of reactions that can be used to append active compounds of the present invention to a substrate is not intended to be exhaustive. Those skilled in the art will readily appreciate various other methods of carrying out these teachings. Further examples and explanations of these types of reactions can be found in U.S. Pat. No. 6,136,157 (Lindeberg et al.) and U.S. Pat. No. 7,115,653 (Baxter et al.), which are each hereby incorporated by reference in their entirety.

Some aspects of the present invention are described in more detail in the following non-limiting examples.

EXAMPLE 1

Synthesis of a 2-Aminoimidazole Library for Anti-Biofilm Screening Utilizing the Sonogashira Reaction. The synthesis of a 21 member library is described that employs a high-yielding Sonogashira reaction (Sonogashira et al., *Tet. Lett.* 1975, 4467-4470; Chinchilla et al., *Chem. Rev.* 2007, 107, 874-922; Schnurch et al., *European Journal of Organic Chemistry* 2006, 3283-3307) on three aryl iodide protected 2-aminoimidazole scaffolds to generate small molecules for screening as anti-biofilm agents.

Access to the desired aryl halide intermediates for the Sonogashira coupling was executed through the commercially available ortho, meta, and para substituted iodobenzoic acid derivatives 3-5 (Scheme 1).

39

Scheme 1. Construction of 2-AI scaffolds.

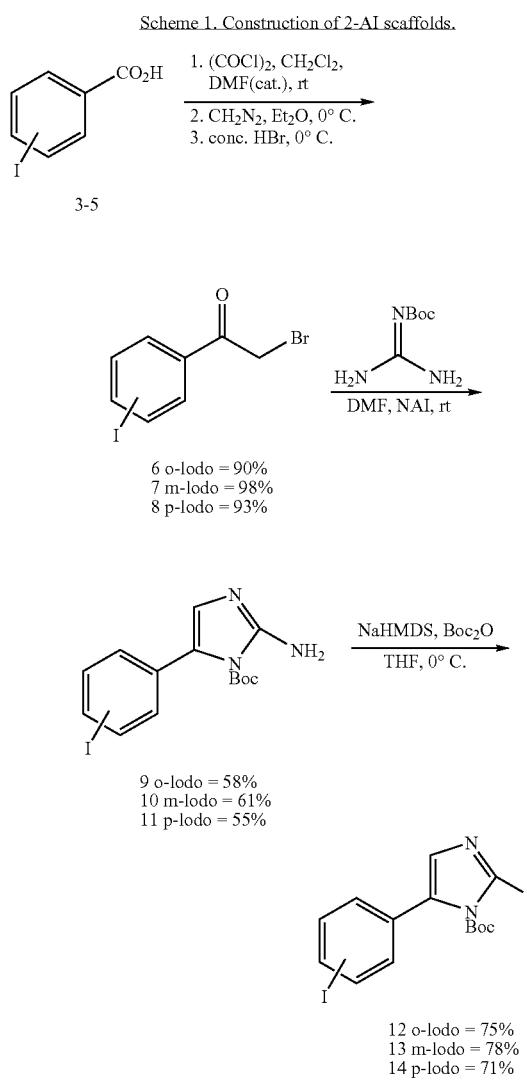

40 intermediate (Poeverlein et al., *Synthesis-Stuttgart* 2007, 3620-3626), and this provided the starting point for catalyst screening and reaction condition optimization (Scheme 2).

Scheme 2. Sonogashira Optimization

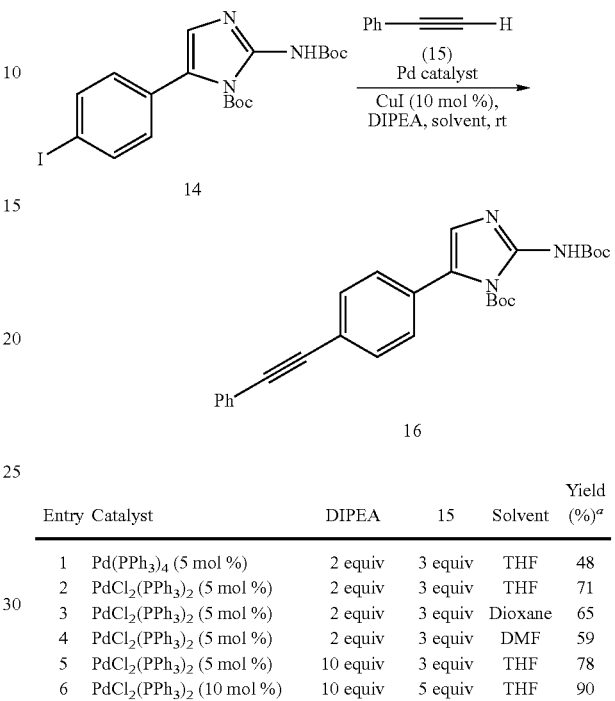

| Entry | Catalyst | DIPEA | 15 | Solvent | Yield (%)[a] |
|---|---|---|---|---|---|
| 1 | Pd(PPh$_3$)$_4$ (5 mol %) | 2 equiv | 3 equiv | THF | 48 |
| 2 | PdCl$_2$(PPh$_3$)$_2$ (5 mol %) | 2 equiv | 3 equiv | THF | 71 |
| 3 | PdCl$_2$(PPh$_3$)$_2$ (5 mol %) | 2 equiv | 3 equiv | Dioxane | 65 |
| 4 | PdCl$_2$(PPh$_3$)$_2$ (5 mol %) | 2 equiv | 3 equiv | DMF | 59 |
| 5 | PdCl$_2$(PPh$_3$)$_2$ (5 mol %) | 10 equiv | 3 equiv | THF | 78 |
| 6 | PdCl$_2$(PPh$_3$)$_2$ (10 mol %) | 10 equiv | 5 equiv | THF | 90 |

[a]Isolated yield.

Conditions were screened using the p-iodo scaffold 14 and phenyl acetylene 15 as the alkyne. PdCl$_2$(PPh$_3$)$_2$ was found to be a better catalyst at promoting the coupling than Pd(PPh$_3$)$_4$ in every condition analyzed. Increasing the catalyst load to 10 mol % was found to be optimal, leading to complete consumption of the aryl iodide starting material. This was essential because incomplete conversion led to difficulty in removing unreacted starting material which was laborious and led to reduced reaction yields. THF was the best solvent among the three scanned. Minor adjustments were also made in the amount of DIPEA used (10 equiv) and the alkyne coupling partner (5 equiv). With the conditions optimized on the trial system, the yield for the Sonogashira coupling was 90% and was deemed acceptable for the synthesis of the library.

Ten electronic and sterically diverse alkynes incorporating a number of synthetically relevant functionalities were then used to generate a small library of 2-AI analogues using the optimized coupling conditions (Scheme 3).

Each was first transformed into its acid chloride before being sequentially reacted with diazomethane and quenched with concentrated HBr. This afforded the requisite α-bromo ketones 6-8 in excellent yields. Installation of the 2-aminoimidazole subunit was achieved through condensation with Boc-guanidine (Zapf et al., *Org. Lett.* 2001, 3, 1133-1136) in the presence of NaI. Attempts at performing the Sonogashira reaction with intermediate 11 proved futile due to its relative insolubility in all organic solvents except DMF. Low yields and difficulty in purification of the desired product were observed, however, when DMF was used in the reaction. It therefore became necessary to protect the exocyclic amine functionality, and this was accomplished by reaction of derivatives 9-11 with LiHMDS in the presence of Boc anhydride (Ando et al., *Synlett* 2006, 2836-2840). Despite the need for the extra synthetic step, scaffolds 12-14 were quickly prepared on multi-gram scales in just three synthetic operations.

Attention then turned to a suitable catalyst system for the Sonogashira reaction. Lindel previously reported the use of PdCl$_2$(PPh$_3$)$_2$ as a catalyst for Heck and Sonogashira type reactions employing an imidazole-based iminophosphorane Scheme 3. Library Synthesis.

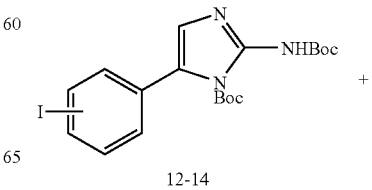

12-14

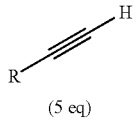

| Entry | Substrate | Alkyne | Yield (%) |
|---|---|---|---|
| 1 | 12 | Ph—≡—H (15) | 94 |
| 2 | 13 | (15) | 87 |
| 3 | 12 | 3,5-difluorophenyl acetylene (16) | 97 |
| 4 | 13 | (16) | 91 |
| 5 | 14 | (16) | 94 |
| 6 | 12 | 2-methoxyphenyl acetylene (17) | 81 |
| 7 | 13 | (17) | 90 |
| 8 | 14 | (17) | 80 |
| 9 | 12 | 4-methoxy-2-methylphenyl acetylene (18) | 92 |
| 10 | 14 | (18) | 85 |
| 11 | 12 | 3-chlorophenyl acetylene (19) | 85 |
| 12 | 13 | (19) | 86 |
| 13 | 13 | 4-pentylphenyl acetylene (20) | 91 |
| 14 | 14 | TMS—≡—H (21) | 85 |
| 15 | 13 | HOCH₂—≡—H (22) | 81[b] |
| 16 | 14 | (22) | 80[b] |
| 17 | 13 | (H₃C)₂NCH₂—≡—H (23) | 86 |
| 18 | 14 | (23) | 90 |
| 19 | 14 | ClCH₂CH₂—≡—H (24) | 82 |
| 20 | 14 | H₃C(CH₂)₅—≡—H (25) | 84 |

[a]Isolated yield.
[b]8.0 equivalents of alkyne used.

Yields for all reactions were good to excellent (80-97%). The highest yielding reactions were those involving the 2,5-difluorophenyl alkyne derivative 16 (Entries 3-5). TMS acetylene (Entry 14) and propargyl alcohol (Entries 15 and 16) were also shown to be suitable coupling partners under the extremely mild reaction conditions. Furthermore, consistently high yields were obtained when a single alkyne was coupled to all three regioisomers, indicating the robustness of the system.

In summary, the Sonogashira reaction was used to build a unique library of 21 complex 2-aminoimidazole based compounds that have the potential to provide access to numerous other more advanced analogues. The reaction proceeds in excellent yield regardless of the alkyne and aryl halide scaffold used. The biological screening of the analogues as modulators of biofilm growth and maintenance is currently underway and our findings will be reported in due course. Additionally, other conditions may be utilized to take advantage of palladium catalyzed cross-couplings to create further libraries of 2-AI based molecules for evaluation as anti-biofilm agents.

EXAMPLE 2

Synthesis of 2-Aminoimidazole Libraries for Anti-Biofilm Screening

Additional libraries are prepared as detailed in Scheme 4.

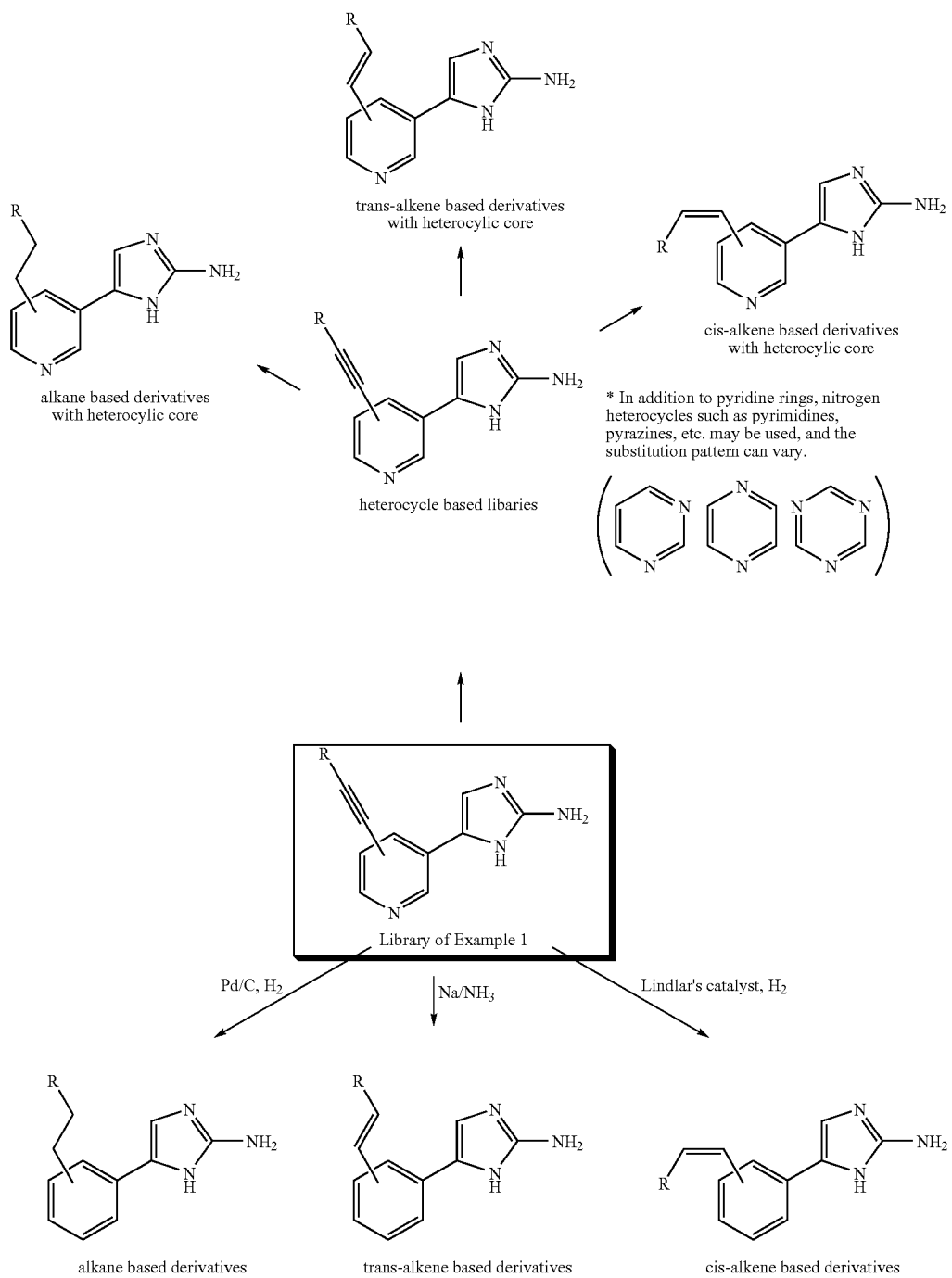

Scheme 4. Additional Library Synthesis.

EXAMPLE 3

Activity testing of compounds against *A. baumannii*. Biofilm inhibition assays were performed by taking an overnight culture of bacterial strain and subculturing it at an $OD_{600}$ of 0.10 into LB medium. The compound being tested was then added at a predetermined concentration and then aliquoted (100 μL) into the wells of a 96-well PVC microtiter plate (Wells not used for samples were filled with 100 μL of deionized water). Plates were then wrapped in GLAD Press n' Seal® and incubated under stationary conditions at 37° C. After 24 hours, the media was discarded from the wells and the plates were washed thoroughly with tap water. Plates were then stained with 100 μL of 0.1% solution of crystal violet (CV) and then incubated at an ambient temperature for 30 minutes. Sample plates were then washed with tap water again, and the remaining stain was solubilized with 200 μL of 95% ethanol. Biofilm inhibition was quantitated by measuring the $OD_{540}$ for each well by transferring 125 μL of the solubilized CV stain into a polystyrene microtiter dish for analysis.

TABLE 1
Inhibition results from assays with *A. Baumannii*.
| COMPOUND | ACTIVITY against *A. baumannii* |
|---|---|
| 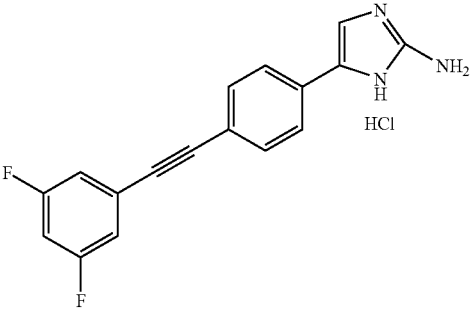 [SMILES: Nc1ncc(-c2ccc(C#Cc3cc(F)cc(F)c3)cc2)[nH]1 ; Cl] | $IC_{50} < 50\ \mu M$ |
| 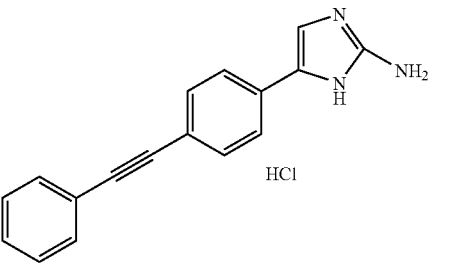 [SMILES: Nc1ncc(-c2ccc(C#Cc3ccccc3)cc2)[nH]1 ; Cl] | $IC_{50} = 6.54\ \mu M$ |
| 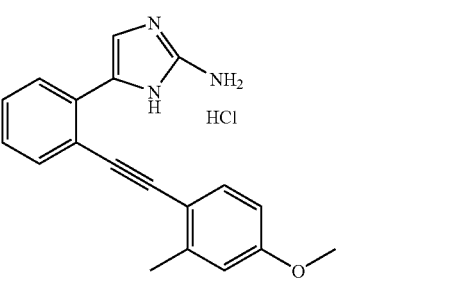 [SMILES: COc1ccc(C#Cc2ccccc2-c2cnc(N)[nH]2)c(C)c1 ; Cl] | $40\ \mu M < IC_{50} < 50\ \mu M$ |
| 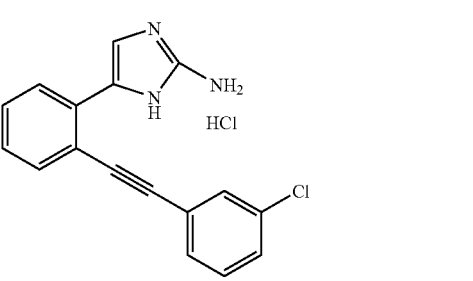 [SMILES: Nc1ncc(-c2ccccc2C#Cc2cccc(Cl)c2)[nH]1 ; Cl] | $IC_{50} < 50\ \mu M$ |
| 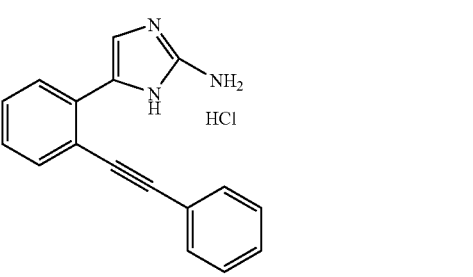 [SMILES: Nc1ncc(-c2ccccc2C#Cc2ccccc2)[nH]1 ; Cl] | $50\ \mu M < IC_{50} < 75\ \mu M$ |

TABLE 1-continued

Inhibition results from assays with *A. Baumannii*.

| COMPOUND | ACTIVITY against *A. baumannii* |
|---|---|
| | 34% inhibition at 100 μM |

EXAMPLE 4

Synthesis of 2-Aminoimidazole Libraries for Anti-Biofilm Screening

Additional libraries were prepared having an amide on the 2-aminoimidazole-phenyl structure.

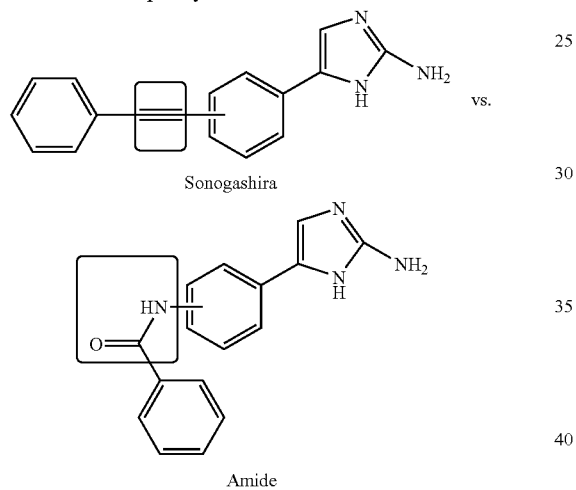

Synthetic methods used for the library creation are outlined below in Scheme 5.

Scheme 5. Synthesis of 2-aminoimidazole-phenyl-amide compounds.

Para-substituted Analogues

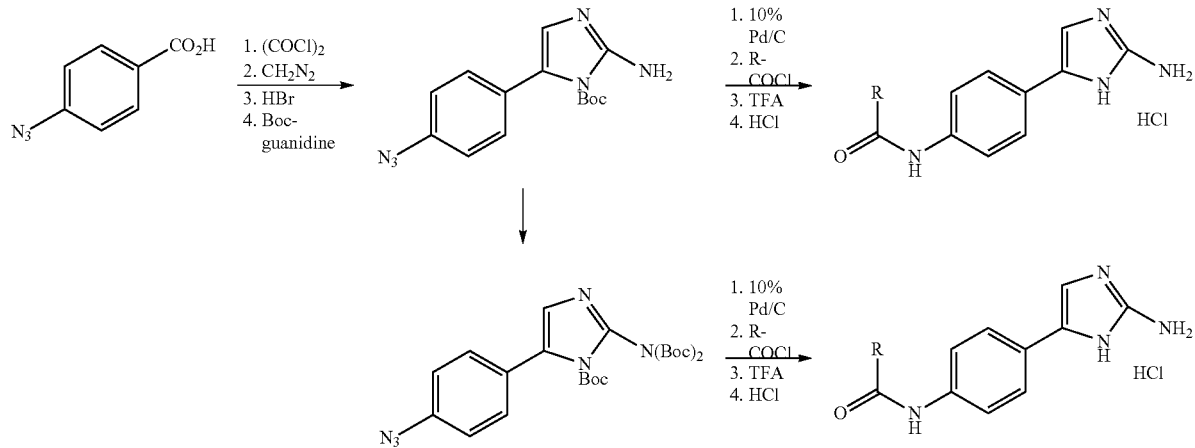

Meta-/ ortho-substituted Analogues
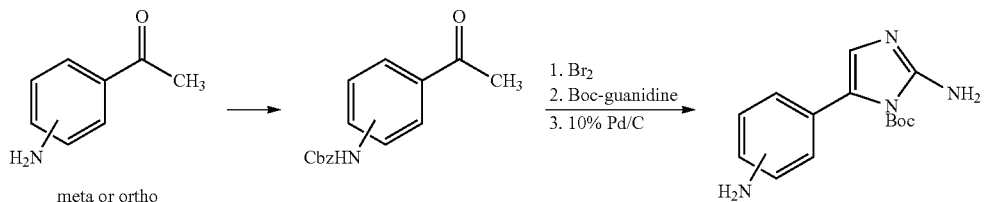
*J. Med. Chem.* 2006, 49, 7342
-continued
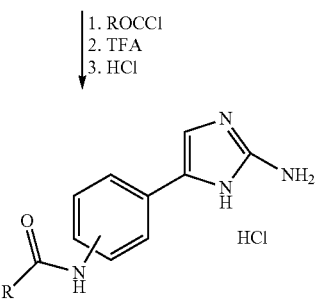
The following compounds have been synthesized.
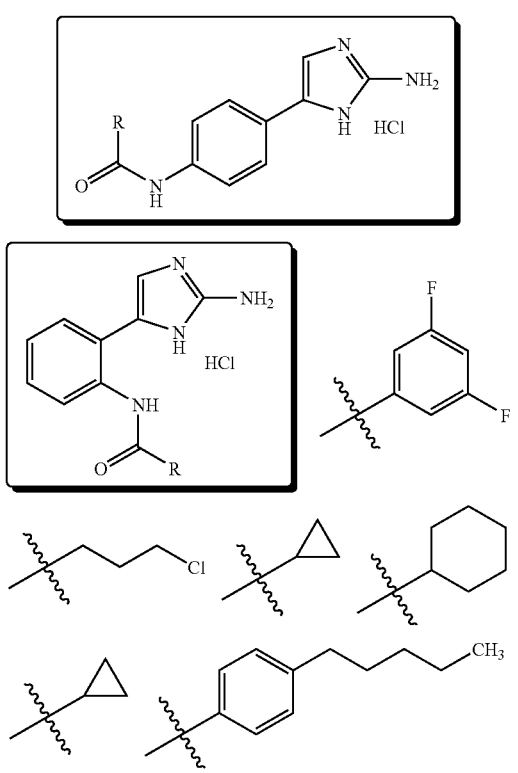
-continued
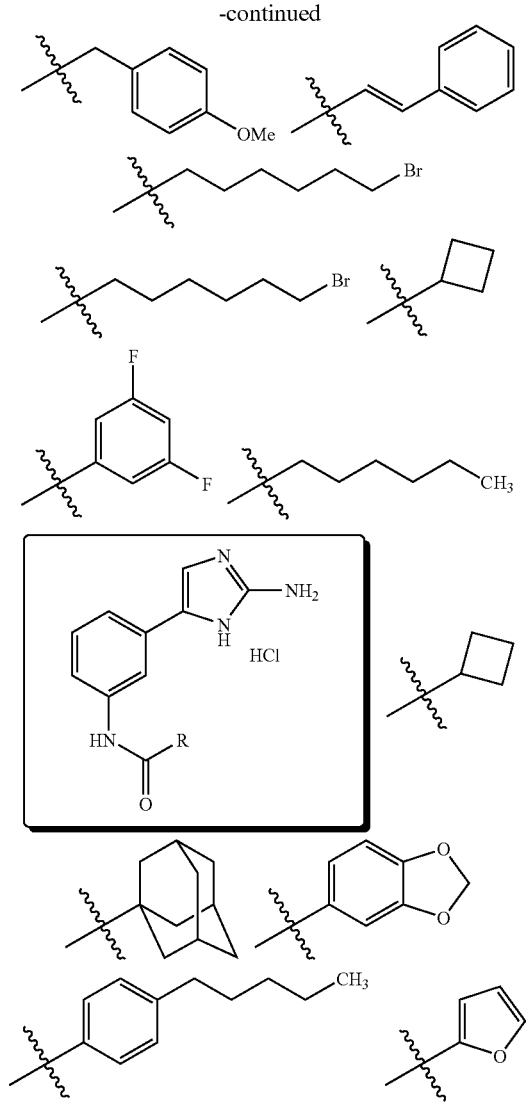

-continued

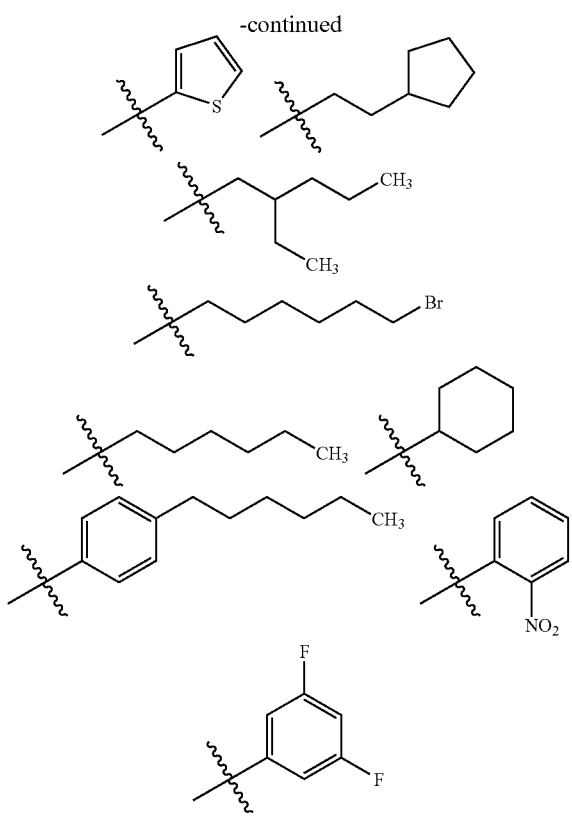

Detailed synthetic methods and characterizations are provided below for many of these compounds.

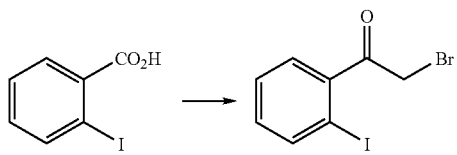 [SMILES: O=C(O)c1ccccc1I ; O=C(CBr)c1ccccc1I]

2-bromo-1-(2-iodophenyl)ethanone

2-Iodobenzoic acid (2.48 g, 10.0 mmol) was dissolved in anhydrous dichloromethane (30 mL) and cooled to 0° C. Oxalyl chloride (2.65 mL, 30.0 mmol) was added drop-wise followed by the addition of a catalytic amount of anhydrous DMF (0.01 mL). The reaction was allowed to warm to room temperature over the course of 1 h and after that time the solution was evaporated to dryness. The crude acid chloride was dissolved in anhydrous dichloromethane (10 mL) and added drop-wise to a 0° C. solution of $CH_2N_2$ (30.0 mmol generated from Diazald®/KOH) in diethyl ether (100 mL). This solution was stirred at 0° C. for 1 h upon which the reaction was quenched via the drop-wise addition of 48% solution of concentrated HBr (3.5 mL). The reaction mixture was diluted with dichloromethane (15 mL) and immediately washed with sat. $NaHCO_3$ (3×25 mL) and brine (2×25 mL) before being dried ($MgSO_4$), filtered and concentrated. The crude oil was purified via flash column chromatography (10-30% EtOAc/Hexanes) to obtain the desired compound 2-bromo-1-(2-iodophenyl)ethanone (2.93 g, 90%) as a yellow oil: $^1$H NMR (400 MHz, DMSO-$d_6$) δ 8.01 (d, 1H, J=7.6 Hz), 7.73 (d, 1H, J=8.0 Hz), 7.53 (t, 1H, J=7.2 Hz), 7.27 (t, 1H, J=7.2 Hz), 4.85 (s, 2H); $^{13}$C NMR (100 MHz, DMSO-$d_6$) δ 195.0, 140.7, 140.5, 132.8, 129.0, 128.2, 93.2, 36.1; HRMS (ESI) calcd for $C_8H_7BrIO$ (MH$^+$) 324.8719. found 324.8721.

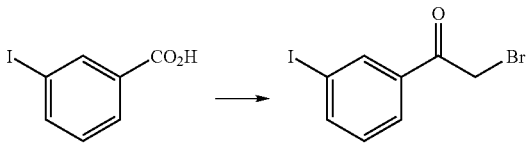 [SMILES: O=C(O)c1cccc(I)c1 ; O=C(CBr)c1cccc(I)c1]

2-bromo-1-(3-iodophenyl)ethanone

In a similar manner, 2.48 g (10.0 mmol) of 3-iodobenzoic acid afforded 3.16 g (98%) of 2-bromo-1-(3-iodophenyl)ethanone as a colorless oil: $^1$H NMR (400 MHz, DMSO-$d_6$) δ 8.29 (m, 1H), 8.02 (m, 2H), 7.35 (t, 1H, J=7.6 Hz), 4.95 (s, 2H); $^{13}$C NMR (100 MHz, DMSO-$d_6$) δ 190.7, 142.2, 136.9, 135.9, 131.0, 128.0, 95.3, 34.2; HRMS (ESI) calcd for $C_8H_7BrIO$ (MH$^+$) 324.8719. found 324.8722.

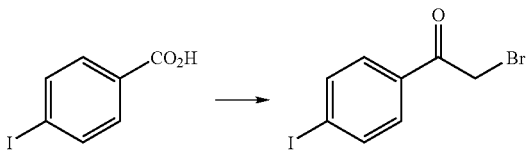 [SMILES: O=C(O)c1ccc(I)cc1 ; O=C(CBr)c1ccc(I)cc1]

2-bromo-1-(4-iodophenyl)ethanone

In a similar manner, 2.00 g (8.06 mmol) of 4-iodobenzoic acid afforded 2.43 g (93%) of 2-bromo-1-(4-iodophenyl)ethanone as a yellow oil: $^1$H NMR (300 MHz, DMSO-$d_6$) δ 7.94 (d, 2H, J=7.5 Hz), 7.72 (d, 2H, J=7.8 Hz), 4.91 (s, 2H); $^{13}$C NMR (75 MHz, CDCl$_3$) δ 191.3, 138.8, 138.7, 133.7, 131.5, 130.7, 102.8, 30.9; HRMS (ESI) calcd for $C_8H_7BrIO$ (MH$^+$) 324.8719. found 324.8718.

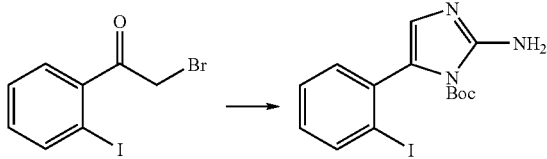 [SMILES: O=C(CBr)c1ccccc1I ; CC(C)(C)OC(=O)n1c(-c2ccccc2I)cnc1N]

2-amino-5-(2-iodophenyl)imidazole-1-carboxylic acid tert-butyl ester

To a solution of 2-bromo-1-(2-iodophenyl)ethanone (2.70 g, 8.31 mmol) in anhydrous DMF (27 mL) was added Boc-guanidine (4.00 g, 24.9 mmol) and sodium iodide (2.47 g, 16.6 mmol). The reaction was stirred at ambient temperature for 72 hours upon which the mixture was partitioned between EtOAc (150 mL) and water (75 mL). The organic layer was successively washed with water (3×50 mL) and brine (2×50 mL) before being dried (Na$_2$SO$_4$) and evaporated to dryness. The resulting crude oil was purified via flash column chromatography (10-30% EtOAc/CH$_2$Cl$_2$) to obtain the target 2-amino-5-(2-iodophenyl)imidazole-1-carboxylic acid tert-butyl ester (1.84 g, 58%) as a tan foam: mp=121° C. (dec.); $^1$H NMR (400 MHz, DMSO-$d_6$) δ 7.92 (m, 1H), 7.27 (dd, 1H, J=1.6, 8.0 Hz), 7.49 (s, 1H), 7.41 (m, 1H), 7.00 (m, 1H), 6.59 (br s, 2H), 1.57 (s, 9H); $^{13}$C NMR (100 MHz, DMSO-d$_6$) δ 149.6, 148.8, 140.3, 137.4, 130.1, 128.8, 128.1, 108.6, 95.7, 85.0, 27.5; HRMS (ESI) calcd for C$_{14}$H$_{17}$IN$_3$O$_2$ (MH$^+$) 386.0360. found 386.0359.

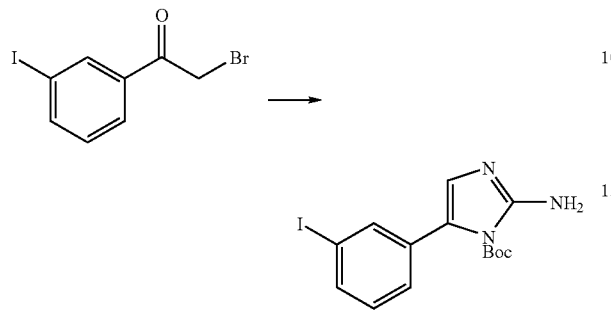

2-amino-5-(3-iodophenyl)imidazole-1-carboxylic acid tert-butyl ester

In a similar manner, 2.50 g (7.71 mmol) of 2-bromo-1-(3-iodophenyl)ethanone afforded 1.82 g (61%) of 2-amino-5-(3-iodophenyl)imidazole-1-carboxylic acid tert-butyl ester as an off-white solid: mp=146-147° C.; $^1$H NMR (400 MHz, DMSO-d$_6$) δ 8.11 (m, 1H), 7.74 (m, 1H), 7.55 (m, 1H), 7.47 (s, 1H), 7.14 (m, 1H), 6.62 (br s, 2H), 1.58 (s, 9H); $^{13}$C NMR (100 MHz, DMSO-d$_6$) δ 150.5, 148.9, 135.8, 135.3, 133.0, 130.6, 123.9, 107.3, 95.0, 93.9, 84.8, 27.6; HRMS (ESI) calcd for C$_{14}$H$_{17}$IN$_3$O$_2$ (MH$^+$) 386.0360. found 386.0361.

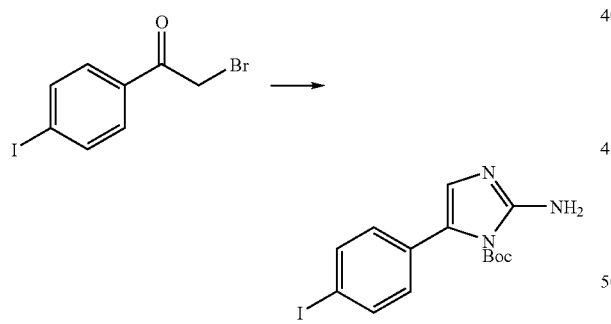

2-amino-5-(4-iodophenyl)imidazole-1-carboxylic acid tert-butyl ester

In a similar manner, 1.10 g (3.39 mmol) of 2-bromo-1-(4-iodophenyl)ethanone afforded 1.43 g (55%) of 2-amino-5-(4-iodophenyl)imidazole-1-carboxylic acid tert-butyl ester as an off-white solid: mp=140-141° C.; $^1$H NMR (300 MHz, DMSO-d$_6$) δ 7.68 (d, 2H, J=8.4 Hz), 7.53 (d, 2H, J=8.7 Hz), 7.42 (s, 1H), 6.61 (br s, 2H), 1.57 (s, 9H); $^{13}$C NMR (100 MHz, DMSO-d$_6$) δ 150.5, 148.9, 137.1, 136.0, 133.0, 126.8, 107.0, 106.9, 92.4, 84.8, 27.6; HRMS (ESI) calcd for C$_{14}$H$_{17}$IN$_3$O$_2$ (MH$^+$) 386.0360. found 386.0358.

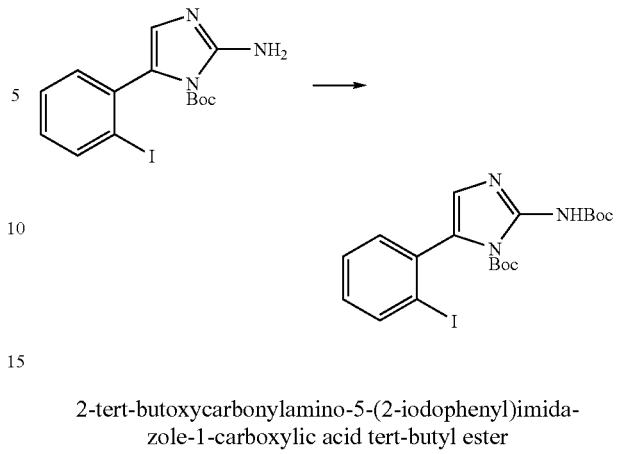

2-tert-butoxycarbonylamino-5-(2-iodophenyl)imidazole-1-carboxylic acid tert-butyl ester To a 0° C. solution of 2-amino-5-(2-iodophenyl)imidazole-1-carboxylic acid tert-butyl ester (1.01 g, 2.62 mmol) and di-tert-butyl dicarbonate (0.600 g, 2.75 mmol) in anhydrous THF (13 mL) was added drop-wise a 1M solution of NaHMDS in THF (5.24 mL, 5.24 mmol). Upon completion the reaction was allowed to stir at 0° C. for an additional 15 minutes before the ice bath was removed and the reaction was permitted to warm to ambient temperature. It was then diluted with EtOAc (20 mL) and quenched with sat. NH$_4$Cl (10 mL). The aqueous layer was removed and the organics were washed successively with sat. NaHCO$_3$ (2×20 mL) and brine (1×20 mL) before being dried (Na$_2$SO$_4$) and concentrated under reduced pressure. The crude oil was purified via flash column chromatography (10-40% EtOAc/Hexanes) to obtain the title compound 2-tert-butoxycarbonylamino-5-(2-iodophenyl)imidazole-1-carboxylic acid tert-butyl ester (0.937 g, 75%) as a white foam: mp=132-133° C.; $^1$H NMR (400 MHz, DMSO-d$_6$) δ 9.60 (s, 1H), 7.96 (m, 1H), 7.89 (s, 1H), 7.70 (d, 2H, J=8.0 Hz), 7.44 (m, 1H), 7.06 (m, 1H), 1.57 (s, 9H), 1.44 (s, 9H); $^{13}$C NMR (100 MHz, DMSO-d$_6$) δ 153.1, 146.7, 140.3, 138.8, 137.8, 136.8, 130.2, 129.3, 128.3, 115.0, 96.1, 85.5, 80.1, 28.0, 27.23; HRMS (ESI) calcd for C$_{19}$H$_{25}$IN$_3$O$_4$ (MH$^+$) 486.0884. found 486.0892.

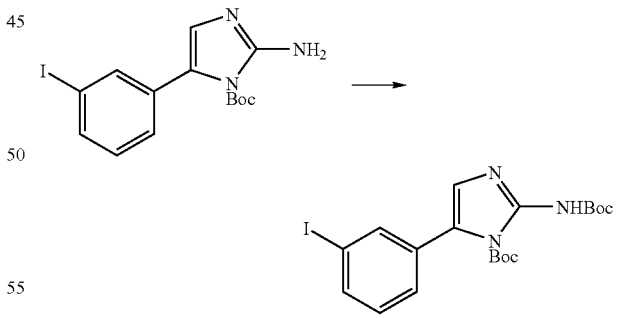

2-tert-butoxycarbonylamino-5-(3-iodophenyl)imidazole-1-carboxylic acid tert-butyl ester In a similar manner, 0.780 g (1.61 mmol) of 2-amino-5-(3-iodophenyl)imidazole-1-carboxylic acid tert-butyl ester afforded 0.768 g (78%) of 2-tert-butoxycarbonylamino-5-(3-iodophenyl) imidazole-1-carboxylic acid tert-butyl ester as an off-white solid: mp=96-97° C.; $^1$H NMR (400 MHz, DMSO-d$_6$) δ 9.57 (s, 1H), 8.18 (m, 1H), 8.00 (s, 1H), 7.84 (d, 2H, J=7.6 Hz), 7.26 (m, 1H), 7.18 (t, 1H, J=7.6 Hz), 1.57 (s, 9H), 1.44 (s, 9H); $^{13}$C NMR (100 MHz, DMSO-d$_6$) δ 152.8, 146.7, 139.8, 135.8, 135.4, 134.9, 132.9, 130.8, 123.9, 113.6, 95.2, 85.4, 80.1, 27.9, 27.3; HRMS (ESI) calcd for C$_{19}$H$_{24}$IN$_3$O$_4$Na (MNa$^+$) 508.0703. found 508.0703.

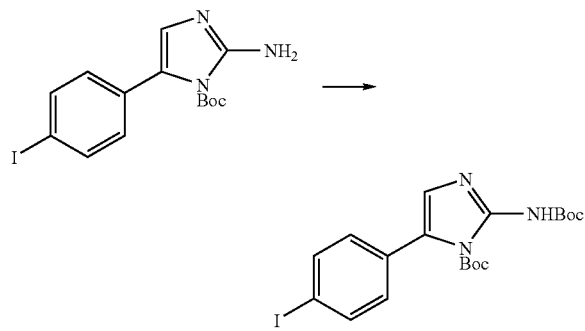

2-tert-butoxycarbonylamino-5-(4-iodophenyl)imidazole-1-carboxylic acid tert-butyl ester In a similar manner, 0.352 g (0.917 mmol) of 2-amino-5-(4-iodophenyl)imidazole-1-carboxylic acid tert-butyl ester afforded 0.403 g (71%) of 2-tert-butoxycarbonylamino-5-(4-iodophenyl) imidazole-1-carboxylic acid tert-butyl ester as an off-white solid: mp=157° C. (dec.); $^1$H NMR (300 MHz, DMSO-d$_6$) δ 9.56 (s, 1H), 7.95 (s, 1H), 7.72 (m, 2H), 7.60 (m, 2H), 1.56 (s, 9H), 1.43 (s, 9H); $^{13}$C NMR (75 MHz, DMSO-d$_6$) δ 152.9, 146.7, 139.7, 137.3, 136.1, 132.3, 126.8, 113.3, 93.1, 85.4, 80.1, 27.9, 27.3; HRMS (ESI) calcd for C$_{19}$H$_{24}$IN$_3$O$_4$Na (MNa$^+$) 508.0703. found 508.0704.

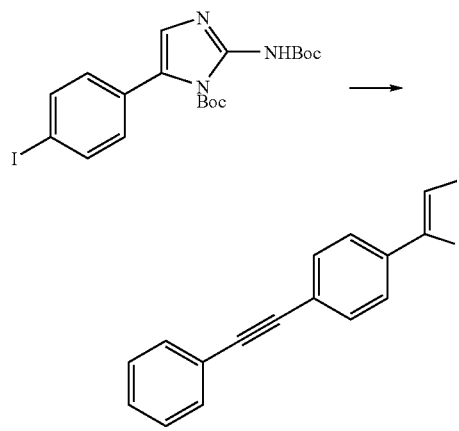

2-tert-butoxycarbonylamino-5-(4-phenylethynylphenyl)imidazole-1-carboxylic acid tert-butyl ester 2-tert-butoxycarbonylamino-5-(4-iodophenyl)imidazole-1-carboxylic acid tert-butyl ester (0.100 g, 0.206 mmol) was dissolved in anhydrous THF (8 mL) and to this solution was added DIPEA (0.359 mL, 2.06 mmol), CuI (0.004 g, 0.021 mmol), and PdCl$_2$(PPh$_3$)$_2$ (0.014 g, 0.021 mmol). The solution was then degassed at ambient temperature for 10 minutes. During this time a solution of the phenyl acetylene (0.105 g, 1.03 mmol) in anhydrous THF (3 mL) was also degassed. The solution of alkyne was added drop-wise to the solution of aryl iodide and the reaction was stirred at room temperature for 12 h. The reaction was filtered through a Celite® pad and the filter cake rinsed with EtOAc (10 mL). The filtrate was washed with sat. NH$_4$Cl (2×10 mL), brine (2×10 mL), and dried (Na$_2$SO$_4$). Filtration and evaporation afforded the crude product which was purified via flash column chromatography (10-50% EtOAc/Hexanes) to obtain 0.085 g (90%) of the target 2-tert-butoxycarbonylamino-5-(4-phenylethynylphenyl) imidazole-1-carboxylic acid tert-butyl ester as a yellow solid: mp=131-132° C.; $^1$H NMR (400 MHz, DMSO-d$_6$) δ 9.60 (s, 1H), 8.00 (s, 1H), 7.86 (d, 2H, J=7.6 Hz), 7.42-7.57 (m, 7H), 1.58 (s, 9H), 1.44 (s, 9H); $^{13}$C NMR (100 MHz, DMSO-d$_6$) δ 152.9, 146.8, 139.9, 136.3, 133.0, 131.7, 131.4, 128.8, 124.9, 122.4, 126.8, 120.9, 113.7, 89.9, 89.5, 85.4, 80.1, 27.9, 27.3; HRMS (ESI) calcd for C$_{27}$H$_{19}$N$_3$O$_4$Na (MNa$^+$) 482.2050. found 482.2051.

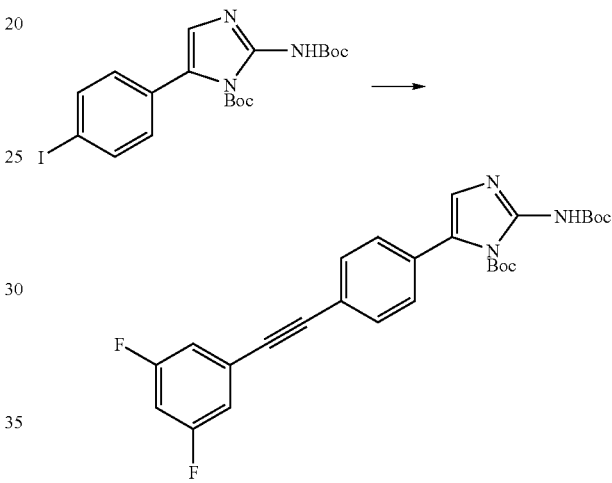

2-tert-butoxycarbonylamino-5-[4-(3,5-difluorophenylethynyl)phenyl]imidazole-1-carboxylic acid tert-butyl ester In a similar manner, 0.100 g (0.206 mmol) of 2-tert-butoxycarbonylamino-5-(4-iodophenyl)imidazole-1-carboxylic acid tert-butyl ester afforded 0.096 g (94%) of 2-tert-butoxycarbonylamino-5-[4-(3,5-difluorophenylethynyl) phenyl]imidazole-1-carboxylic acid tert-butyl ester as a brown solid: mp=197° C. (dec.); $^1$H NMR (300 MHz, DMSO-d$_6$) δ 9.60 (s, 1H), 8.02 (s, 1H), 7.91 (d, 2H, J=8.7 Hz), 7.59 (d, 2H, J=8.7 Hz), 7.34 (m, 3H), 1.58 (s, 9H), 1.44 (s, 9H); $^{13}$C NMR (100 MHz, DMSO-d$_6$) δ 163.5, 161.1, 152.8, 146.7, 139.9, 136.2, 133.9, 134.6, 133.6, 131.9, 128.0, 125.2, 119.9, 114.8, 114.5, 114.0, 105.0, 91.5, 87.6, 85.4, 80.1, 27.7, 27.3; HRMS (ESI) calcd for C$_{27}$H$_{27}$F$_2$N$_3$O$_4$Na (MNa$^+$) 518.1861. found 518.1861.

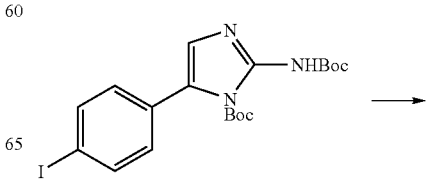

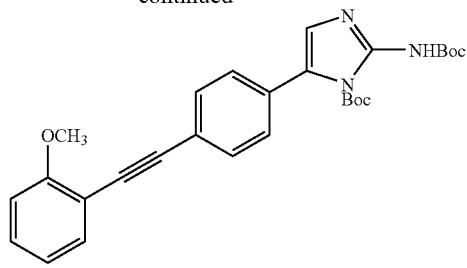

2-tert-butoxycarbonylamino-5-[4-(2-methoxyphenyl-ethynyl)phenyl]imidazole-1-carboxylic acid tert-butyl ester In a similar manner, 0.100 g (0.206 mmol) of 2-tert-butoxycarbonylamino-5-(4-iodophenyl)imidazole-1-carboxylic acid tert-butyl ester afforded 0.080 g (80%) of 2-tert-butoxycarbonylamino-5-[4-(2-methoxyphenylethynyl)phenyl]imidazole-1-carboxylic acid tert-butyl ester as a yellow foam: mp=97-98° C.; $^1$H NMR (400 MHz, DMSO-$d_6$) δ 9.60 (s, 1H), 7.99 (s, 1H), 7.85 (d, 2H, J=7.2 Hz), 7.53 (d, 2H, J=7.6 Hz), 7.49 (m, 1H), 7.39 (t, 1H, J=8.0 Hz), 7.11 (d, 1H, J=8.4 Hz), 6.97 (t, 1H, J=7.6 Hz), 3.86 (s, 3H), 1.58 (s, 9H), 1.43 (s, 9H); $^{13}$C NMR (100 MHz, DMSO-$d_6$) δ 159.6, 152.9, 146.8, 139.9, 136.3, 133.1, 132.7, 131.5, 130.4, 130.0, 124.9, 121.3, 120.5, 113.6, 111.4, 93.1, 86.7, 85.4, 80.1, 55.7, 27.9, 27.3; HRMS (ESI) calcd for $C_{28}H_{32}N_3O_5$ (MH$^+$) 490.2336. found 490.2335.

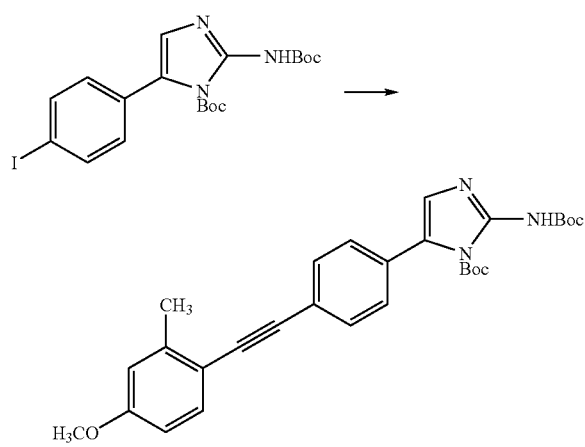

2-tert-butoxycarbonylamino-5-[4-(4-methoxy-2-methylphenylethynyl)phenyl]imidazole-1-carboxylic acid tert-butyl ester In a similar manner, 0.100 g (0.206 mmol) of 2-tert-butoxycarbonylamino-5-(4-iodophenyl)imidazole-1-carboxylic acid tert-butyl ester afforded 0.087 g (85%) of 2-tert-butoxycarbonylamino-5-[4-(4-methoxy-2-methylphenylethynyl)phenyl]imidazole-1-carboxylic acid tert-butyl ester as a yellow foam: mp=142-143° C.; $^1$H NMR (400 MHz, DMSO-$d_6$) δ 9.59 (s, 1H), 7.98 (s, 1H), 7.86 (d, 2H, J=8.4 Hz), 7.53 (d, 2H, J=8.4 Hz), 7.43 (d, 1H, J=8.4 Hz), 6.92 (d, 1H, J=2.4 Hz), 6.81 (dd, 1H, J=2.4, 8.4 Hz), 3.78 (s, 3H), 2.45 (s, 3H), 1.57 (s, 9H), 1.44 (s, 9H); $^{13}$C NMR (100 MHz, DMSO-$d_6$) δ 159.5, 152.9, 146.8, 141.5, 139.8, 136.4, 133.0, 132.5, 131.4, 124.8, 121.6, 115.2, 114.3, 113.5, 111.8, 92.0, 88.9, 85.4, 80.1, 55.2, 27.9, 27.3, 20.6; HRMS (ESI) calcd for $C_{29}H_{34}N_3O_5$ (MH$^+$) 504.2492. found 504.2493.

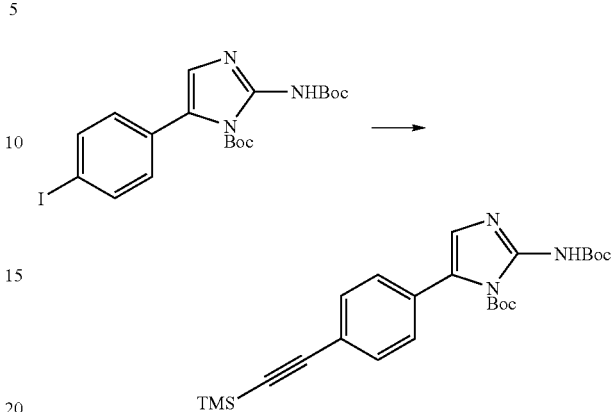

2-tert-butoxycarbonylamino-5-(4-trimethylsilanyl-ethynylphenyl)imidazole-1-carboxylic acid tert-butyl ester In a similar manner, 0.100 g (0.206 mmol) of 2-tert-butoxycarbonylamino-5-(4-iodophenyl)imidazole-1-carboxylic acid tert-butyl ester afforded 0.080 g (85%) of 2-tert-butoxycarbonylamino-5-(4-trimethylsilanylethynylphenyl)imidazole-1-carboxylic acid tert-butyl ester as a pale yellow solid: mp=88-89° C.; $^1$H NMR (400 MHz, DMSO-$d_6$) δ 9.59 (s, 1H), 7.99 (s, 1H), 7.81 (d, 2H, J=8.0 Hz), 7.46 (d, 2H, J=8.4 Hz), 1.57 (s, 9H), 1.43 (s, 9H), 0.23 (s, 9H); $^{13}$C NMR (75 MHz, DMSO-$d_6$) δ 152.8, 146.7, 139.9, 136.2, 133.2, 131.9, 124.8, 120.7, 113.8, 105.3, 94.6, 85.4, 80.1, 27.9, 27.3, −0.07; HRMS (ESI) calcd for $C_{24}H_{33}N_3O_4SiNa$ (MNa$^+$) 478.2132. found 478.2135.

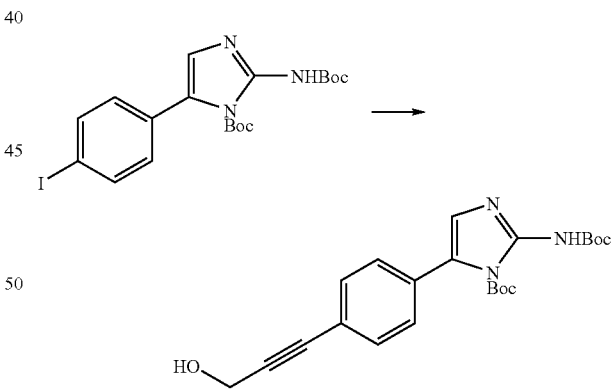

2-tert-butoxycarbonylamino-5-[4-(3-hydroxyprop-1-ynyl)phenyl]imidazole-1-carboxylic acid tert-butyl ester In a similar manner, 0.100 g (0.206 mmol) of 2-tert-butoxycarbonylamino-5-(4-iodophenyl)imidazole-1-carboxylic acid tert-butyl ester afforded 0.068 g (80%) of 2-tert-butoxycarbonylamino-5-[4-(3-hydroxyprop-1-ynyl)phenyl] imidazole-1-carboxylic acid tert-butyl ester as a yellow solid: mp=76-77° C.; $^1$H NMR (400 MHz, DMSO-$d_6$) δ 9.56 (s, 1H), 7.96 (s, 1H), 7.80 (d, 2H, J=7.2 Hz), 7.42 (d, 2H, J=7.2

Hz), 5.36 (t, 1H, J=5.6 Hz), 4.31 (d, 2H, J=5.6 Hz), 1.57 (s, 9H), 1.43 (s, 9H); ¹³C NMR (100 MHz, DMSO-d₆) δ 152.9, 146.8, 139.8, 136.3, 132.7, 131.6, 124.8, 121.1, 113.6, 90.4, 85.4, 83.7, 80.1, 49.5, 28.0, 27.3; HRMS (ESI) calcd for C$_{22}$H$_{27}$N$_3$O$_5$Na (MNa$^+$) 436.1842. found 436.1841.

mp=61-62° C.; ¹H NMR (300 MHz, DMSO-d₆) δ 9.57 (s, 1H), 7.95 (s, 1H), 7.77 (m, 2H), 7.40 (m, 2H), 3.77 (t, 2H, J=6.3 Hz), 2.59 (t, 2H, J=6.9 Hz), 1.99 (m, 2H), 1.57 (s, 9H), 1.44 (s, 9H); ¹³C NMR (100 MHz, DMSO-d₆) δ 152.9, 146.8, 139.8, 137.3, 136.4, 132.3, 131.6, 124.7, 121.6, 113.4, 89.4, 85.3, 81.2, 80.1, 44.4, 31.1, 27.9, 27.3, 16.3; HRMS (ESI) calcd for C$_{24}$H$_{30}$ClN$_3$O$_4$Na (MNa$^+$) 482.1817. found 482.1816.

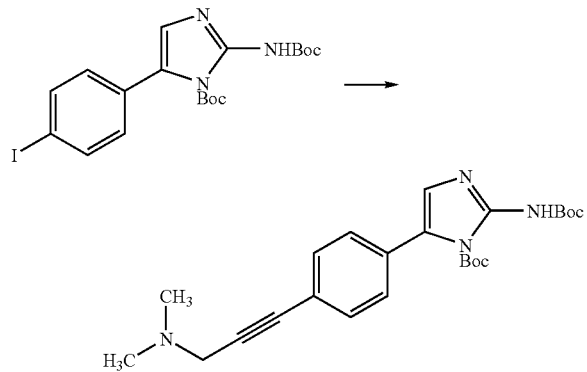

2-tert-butoxycarbonylamino-5-[4-(3-dimethylamino-prop-1-ynyl)phenyl]imidazole-1-carboxylic acid tert-butyl ester In a similar manner, 0.100 g (0.206 mmol) of 2-tert-butoxycarbonylamino-5-(4-iodophenyl)imidazole-1-carboxylic acid tert-butyl ester afforded 0.081 g (90%) of 2-tert-butoxycarbonylamino-5-[4-(3-dimethylaminoprop-1-ynyl)phenyl]imidazole-1-carboxylic acid tert-butyl ester as a yellow oil: ¹H NMR (400 MHz, DMSO-d₆) δ 9.58 (s, 1H), 7.96 (s, 1H), 7.81 (d, 2H, J=8.8 Hz), 7.43 (d, 2H, J=8.4 Hz), 3.46 (s, 2H), 2.25 (s, 6H), 1.57 (s, 9H), 1.44 (s, 9H); ¹³C NMR (75 MHz, DMSO-d₆) δ 152.9, 146.8, 139.8, 136.4, 132.5, 131.7, 124.8, 121.2, 113.5, 85.8, 85.4, 85.0, 80.1, 47.8, 43.8, 27.9, 27.3; HRMS (ESI) calcd for C$_{24}$H$_{32}$N$_4$O$_4$Na (MNa$^+$) 463.2315. found 463.2313.

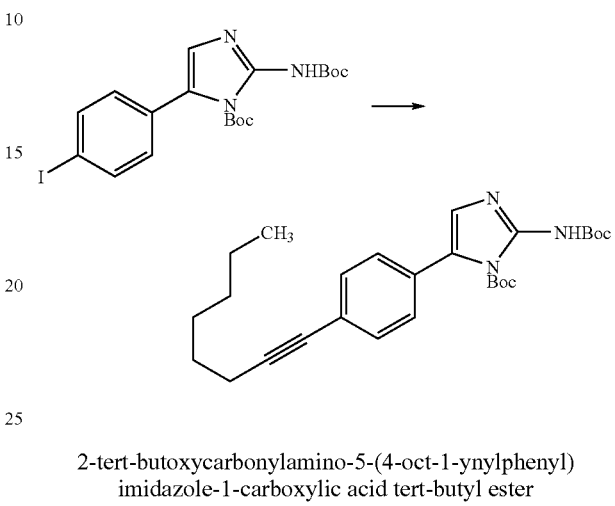

2-tert-butoxycarbonylamino-5-(4-oct-1-ynylphenyl)imidazole-1-carboxylic acid tert-butyl ester In a similar manner, 0.100 g (0.206 mmol) of 2-tert-butoxycarbonylamino-5-(4-iodophenyl)imidazole-1-carboxylic acid tert-butyl ester afforded 0.081 g (84%) of 2-tert-butoxycarbonylamino-5-(4-oct-1-ynylphenyl)imidazole-1-carboxylic acid tert-butyl ester as a yellow oil: ¹H NMR (400 MHz, CDCl₃) δ 9.17 (s, 1H), 7.75 (d, 2H, J=8.0 Hz), 7.37 (d, 2H, J=8.0 Hz), 7.25 (s, 1H), 2.40 (t, 2H, J=7.2 Hz), 1.63 (s, 9H), 1.60 (m, 2H), 1.54 (s, 9H), 1.45 (m, 2H), 1.33 (m, 4H), 0.090 (t, 3H, J=6.4 Hz); ¹³C NMR (100 MHz, DMSO-d₆) δ 150.1, 149.5, 142.6, 138.6, 131.8, 127.0, 125.4, 123.3, 108.1, 91.3, 86.9, 82.1, 80.9, 31.6, 29.0, 28.9, 28.5, 28.3, 28.2, 22.8, 19.7, 14.3; HRMS (ESI) calcd for C$_{27}$H$_{38}$N$_3$O$_4$ (MH$^+$) 468.2856. found 468.2860.

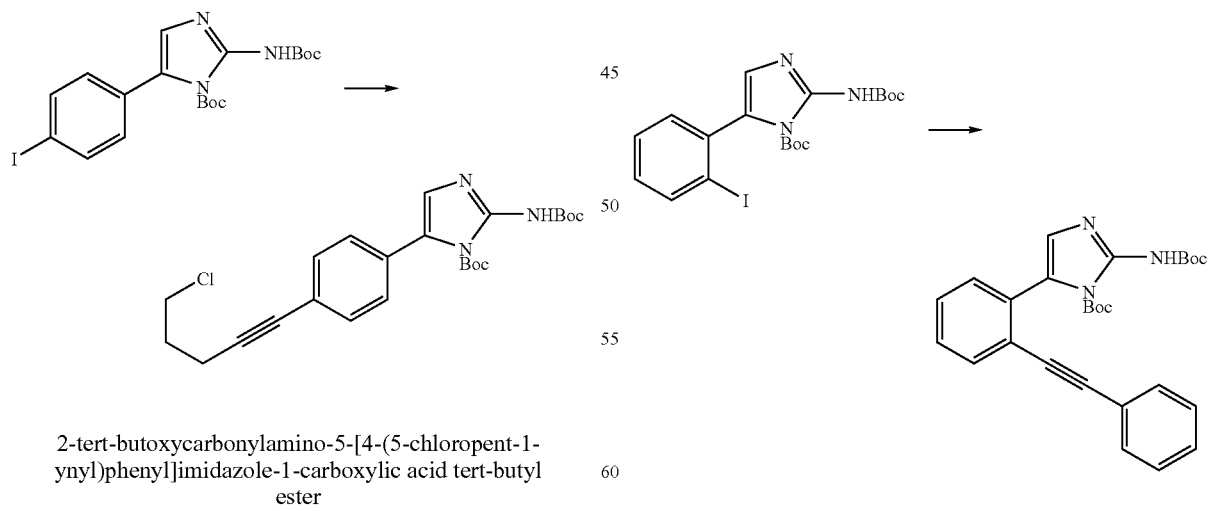

2-tert-butoxycarbonylamino-5-[4-(5-chloropent-1-ynyl)phenyl]imidazole-1-carboxylic acid tert-butyl ester In a similar manner, 0.100 g (0.206 mmol) of 2-tert-butoxycarbonylamino-5-(4-iodophenyl)imidazole-1-carboxylic acid tert-butyl ester afforded 0.062 g (82%) of 2-tert-butoxycarbonylamino-5-[4-(5-chloropent-1-ynyl)phenyl]imidazole-1-carboxylic acid tert-butyl ester as a yellow solid:

2-tert-butoxycarbonylamino-5-(2-phenylethynylphenyl)imidazole-1-carboxylic acid tert-butyl ester In a similar manner, 0.100 g (0.206 mmol) of 2-tert-butoxycarbonylamino-5-(2-iodophenyl)imidazole-1-carboxylic acid tert-butyl ester afforded 0.091 g (94%) of 2-tert-butoxycarbonylamino-5-(2-phenylethynylphenyl)imidazole-1-carboxylic acid tert-butyl ester as a yellow solid: mp=113-114° C.; $^1$H NMR (400 MHz, DMSO-d$_6$) δ 9.62 (s, 1H), 8.20 (s, 1H), 8.02 (d, 1H, J=8.4 Hz), 7.62 (m, 3H), 7.47 (m, 4H), 7.35 (m, 1H), 1.58 (s, 9H), 1.44 (s, 9H); $^{13}$C NMR (100 MHz, DMSO-d$_6$) δ 152.8, 146.7, 139.5, 134.9, 133.4, 133.4, 131.3, 129.2, 129.1, 128.9, 127.3, 127.1, 122.1, 117.9, 115.1, 94.0, 89.5, 85.5, 80.1, 27.9, 27.2; HRMS (ESI) calcd for C$_{27}$H$_{29}$N$_3$O$_4$Na (MNa$^+$) 482.2050. found 482.2050.

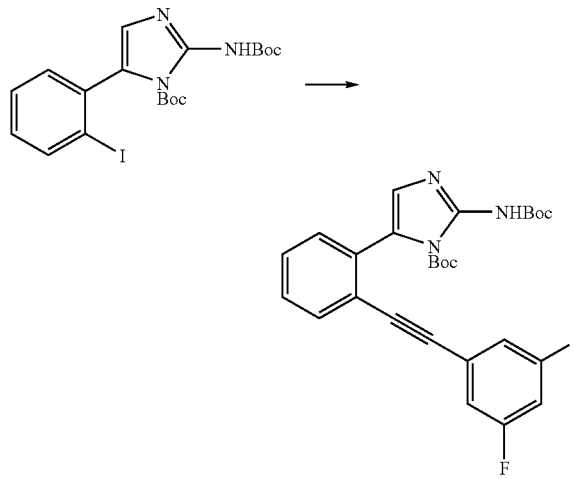

2-tert-butoxycarbonylamino-5-[2-(3,5-difluorophenylethynyl)phenyl]imidazole-1-carboxylic acid tert-butyl ester In a similar manner, 0.100 g (0.206 mmol) of 2-tert-butoxycarbonylamino-5-(2-iodophenyl)imidazole-1-carboxylic acid tert-butyl ester afforded 0.099 g (97%) of 2-tert-butoxycarbonylamino-5-[2-(3,5-difluorophenylethynyl)phenyl]imidazole-1-carboxylic acid tert-butyl ester as a yellow foam: mp=161-162° C.; $^1$H NMR (300 MHz, DMSO-d$_6$) δ 9.62 (s, 1H), 8.11 (s, 1H), 8.03 (m, 1H), 7.65 (m, 1H), 7.55 (m, 1H), 7.34-7.44 (m, 4H), 1.49 (s, 9H), 1.44 (s, 9H); $^{13}$C NMR (75 MHz, DMSO-d$_6$) δ 164.1, 160.7, 152.7, 146.7, 139.6, 134.7, 133.9, 133.5, 129.8, 127.3, 124.8, 117.1, 115.2, 114.8, 114.5, 105.3, 91.4, 91.4, 85.5, 80.2, 27.9, 27.1; HRMS (ESI) calcd for C$_{27}$H$_{27}$F$_2$N$_3$O$_4$Na (MNa$^+$) 518.1861. found 518.1865.

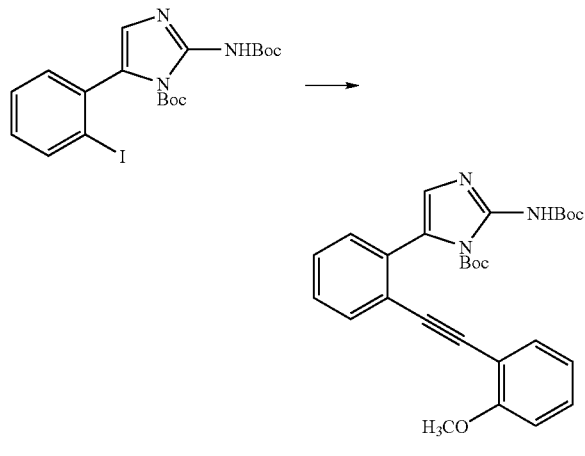

2-tert-butoxycarbonylamino-5-[2-(2-methoxyphenylethynyl)phenyl]imidazole-1-carboxylic acid tert-butyl ester In a similar manner, 0.100 g (0.206 mmol) of 2-tert-butoxycarbonylamino-5-(2-iodophenyl)imidazole-1-carboxylic acid tert-butyl ester afforded 0.081 g (81%) of 2-tert-butoxycarbonyl amino-5-[2-(2-methoxyphenylethynyl)phenyl]imidazole-1-carboxylic acid tert-butyl ester as a tan foam: mp=134-135° C.; $^1$H NMR (300 MHz, DMSO-d$_6$) δ 9.62 (s, 1H), 8.33 (s, 1H), 8.06 (d, 1H, J=7.2 Hz), 7.43-7.60 (m, 4H), 7.33 (t, 1H, J=6.3 Hz), 7.13 (d, 1H, J=8.4 Hz), 7.02 (t, 1H, J=7.8 Hz), 3.87 (s, 3H), 1.46 (s, 9H), 1.44 (s, 9H); $^{13}$C NMR (100 MHz, DMSO-d$_6$) δ 159.8, 153.0, 146.7, 139.2, 134.9, 133.4, 133.1, 133.0, 130.7, 128.9, 127.2, 126.9, 120.6, 118.3, 115.4, 111.4, 111.1, 92.9, 91.2, 85.4, 80.1, 55.8, 27.9, 27.2; HRMS (ESI) calcd for C$_{28}$H$_{32}$N$_3$O$_5$ (MH$^+$) 490.2336. found 490.2332.

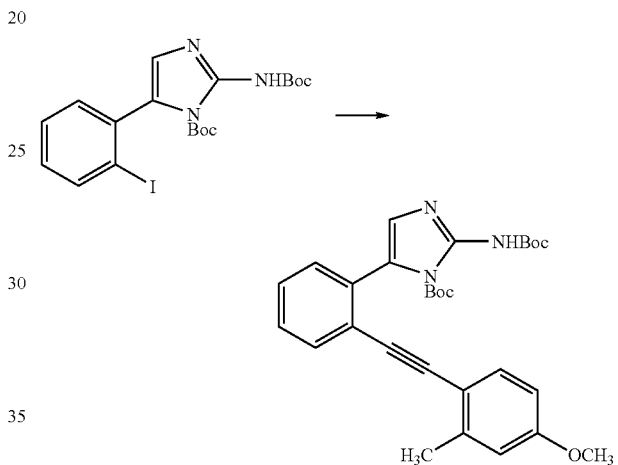

2-tert-butoxycarbonylamino-5-[2-(4-methoxy-2-methylphenylethynyl)phenyl]imidazole-1-carboxylic acid tert-butyl ester In a similar manner, 0.100 g (0.206 mmol) of 2-tert-butoxycarbonylamino-5-(2-iodophenyl)imidazole-1-carboxylic acid tert-butyl ester afforded 0.095 g (92%) of 2-tert-butoxycarbonylamino-5-[2-(4-methoxy-2-methylphenylethynyl)phenyl]imidazole-1-carboxylic acid tert-butyl ester as a yellow foam: mp=59-60° C.; $^1$H NMR (300 MHz, DMSO-d$_6$) δ 9.60 (s, 1H), 8.21 (s, 1H), 8.00 (d, 1H, J=7.5 Hz), 7.61 (d, 1H, J=7.8 Hz), 7.47 (m, 2H), 7.33 (t, 1H, J=6.9 Hz), 6.96 (d, 1H, J=2.1 Hz), 6.81 (dd, 1H, J=2.7, 8.7 Hz), 3.78 (s, 3H), 2.46 (s, 3H), 1.47 (s, 9H), 1.44 (s, 9H); $^{13}$C NMR (75 MHz, DMSO-d$_6$) δ 159.7, 152.8, 146.7, 141.6, 139.4, 135.1, 133.4, 133.1, 132.9, 128.7, 127.3, 127.0, 118.7, 115.3, 115.0, 114.1, 111.9, 93.2, 91.8, 85.5, 80.1, 55.3, 27.9, 27.2, 20.7; HRMS (ESI) calcd for C$_{29}$H$_{34}$N$_3$O$_5$ (MH$^+$) 504.2492. found 504.2495.

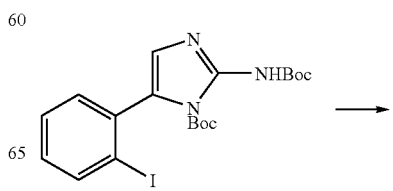

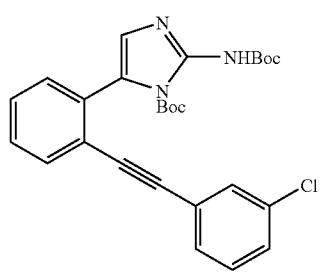

2-tert-butoxycarbonylamino-5-[2-(3-chlorophenyl-ethynyl)phenyl]imidazole-1-carboxylic acid tert-butyl ester In a similar manner, 0.100 g (0.206 mmol) of 2-tert-butoxycarbonylamino-5-(2-iodophenyl)imidazole-1-carboxylic acid tert-butyl ester afforded 0.086 g (85%) of 2-tert-butoxycarbonylamino-5-[2-(3-chlorophenylethynyl)phenyl]imidazole-1-carboxylic acid tert-butyl ester as an orange foam: mp=61-62° C.; $^1$H NMR (300 MHz, DMSO-$d_6$) δ 9.61 (s, 1H), 8.15 (s, 1H), 8.04 (m, 1H), 8.01-8.14 (m, 2H), 7.48-7.69 (m, 4H), 7.36 (m, 1H), 1.48 (s, 9H), 1.44 (s, 9H); $^{13}$C NMR (75 MHz, DMSO-$d_6$) δ 152.8, 146.6, 139.5, 134.8, 133.6, 133.5, 130.7, 130.7, 130.1, 129.5, 129.2, 127.3, 127.1, 124.1, 117.5, 115.2, 92.3, 90.7, 85.5, 80.2, 27.9, 27.2; HRMS (ESI) calcd for $C_{27}H_{28}ClN_3O_4Na$ (MNa$^+$) 516.1660. found 516.1658.

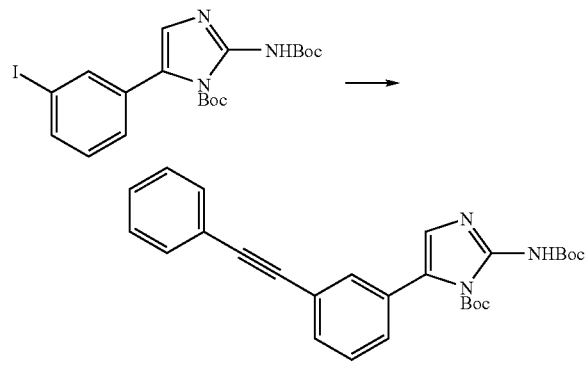

2-tert-butoxycarbonylamino-5-(3-phenylethynylphenyl)imidazole-1-carboxylic acid tert-butyl ester In a similar manner, 0.100 g (0.206 mmol) of 2-tert-butoxycarbonylamino-5-(3-iodophenyl)imidazole-1-carboxylic acid tert-butyl ester afforded 0.084 g (87%) of 2-tert-butoxycarbonylamino-5-(3-phenylethynylphenyl)imidazole-1-carboxylic acid tert-butyl ester as an orange foam: mp=76-77° C.; $^1$H NMR (300 MHz, DMSO-$d_6$) δ 9.58 (s, 1H), 8.04 (s, 1H), 8.01 (m, 1H), 7.85 (m, 1H), 7.59 (m, 2H), 7.44 (m, 5H), 1.58 (s, 9H), 1.44 (s, 9H); $^{13}$C NMR (100 MHz, DMSO-$d_6$) δ 152.9, 146.8, 139.8, 136.1, 133.2, 131.4, 130.1, 129.2, 128.8, 127.4, 125.0, 122.6, 122.3, 113.5, 115.1, 89.4, 89.3, 85.4, 80.1, 27.9, 27.3; HRMS (ESI) calcd for $C_{27}H_{29}N_3O_4Na$ (MNa$^+$) 482.2050. found 482.2053.

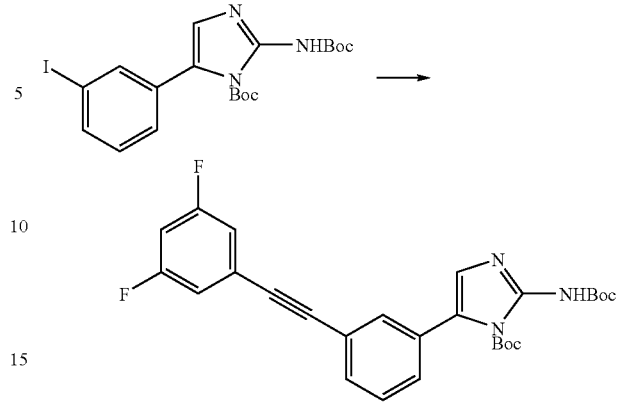

2-tert-butoxycarbonylamino-5-[3-(3,5-difluorophenylethynyl)phenyl]imidazole-1-carboxylic acid tert-butyl ester In a similar manner, 0.100 g (0.206 mmol) of 2-tert-butoxycarbonylamino-5-(3-iodophenyl)imidazole-1-carboxylic acid tert-butyl ester afforded 0.093 g (91%) of 2-tert-butoxycarbonylamino-5-[3-(3,5-difluorophenylethynyl)phenyl]imidazole-1-carboxylic acid tert-butyl ester as a tan solid: mp=69° C. (dec.); $^1$H NMR (300 MHz, DMSO-$d_6$) δ 9.58 (s, 1H), 8.04 (s, 1H), 8.02 (s, 1H), 7.90 (m, 1H), 7.48 (m, 1H), 7.37 (m, 3H), 1.58 (s, 9H), 1.44 (s, 9H); $^{13}$C NMR (100 MHz, DMSO-$d_6$) δ 163.6, 161.2, 152.8, 146.8, 139.8, 136.0, 133.3, 130.3, 129.3, 127.7, 125.6, 125.2, 121.7, 114.9, 114.6, 113.5, 105.2, 91.2, 87.1, 85.4, 80.1, 27.9, 27.3; HRMS (ESI) calcd for $C_{27}H_{27}F_2N_3O_4Na$ (MNa$^+$) 518.1861. found 518.1866.

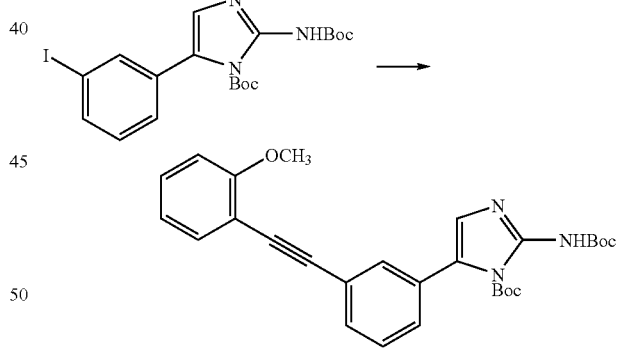

2-tert-butoxycarbonylamino-5-[3-(2-methoxyphenyl-ethynyl)phenyl]imidazole-1-carboxylic acid tert-butyl ester In a similar manner, 0.100 g (0.206 mmol) of 2-tert-butoxycarbonylamino-5-(3-iodophenyl)imidazole-1-carboxylic acid tert-butyl ester afforded 0.090 g (90%) of 2-tert-butoxycarbonylamino-5-[3-(2-methoxyphenylethynyl)phenyl]imidazole-1-carboxylic acid tert-butyl ester as an orange foam: mp=75-76° C.; $^1$H NMR (300 MHz, DMSO-$d_6$) δ 9.58 (s, 1H), 8.04 (s, 1H), 7.96 (s, 1H), 7.85 (m, 1H), 7.52 (m, 1H), 7.41 (m, 3H), 7.11 (d, 1H, J=8.1 Hz), 6.98 (t, 1H, J=7.5 Hz), 3.87 (s, 3H), 1.58 (s, 9H), 1.44 (s, 9H); $^{13}$C NMR (75 MHz, DMSO-d$_6$) δ 159.7, 152.8, 146.8, 139.8, 136.1, 133.6, 130.5, 130.0, 129.1, 127.2, 124.8, 123.1, 120.5, 113.5, 111.4, 111.2, 86.2, 85.3, 80.1, 55.7, 27.9, 27.3; HRMS (ESI) calcd for C$_2$H$_{32}$N$_3$O$_5$ (MH$^+$) 490.2336. found 490.2333.

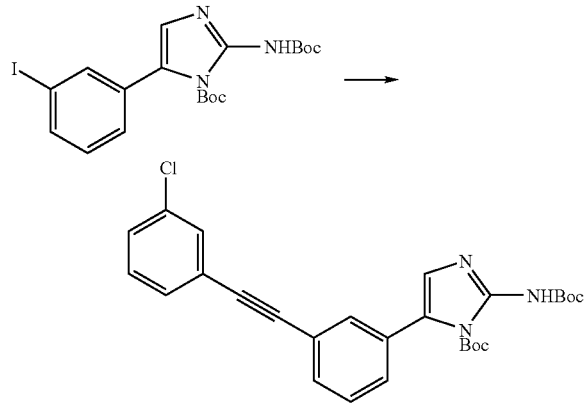

2-tert-butoxycarbonylamino-5-[3-(3-chlorophenyl-ethynyl)phenyl]imidazole-1-carboxylic acid tert-butyl ester In a similar manner, 0.100 g (0.206 mmol) of 2-tert-butoxycarbonylamino-5-(3-iodophenyl)imidazole-1-carboxylic acid tert-butyl ester afforded 0.087 g (86%) of 2-tert-butoxycarbonylamino-5-[3-(3-chlorophenylethynyl)phenyl]imidazole-1-carboxylic acid tert-butyl ester as an off-white foam: mp=67-68° C.; $^1$H NMR (300 MHz, DMSO-d$_6$) δ 9.58 (s, 1H), 8.03 (m, 2H), 7.86 (m, 1H), 7.66 (m, 1H), 7.45-7.57 (m, 5H), 7.36 (m, 1H), 1.48 (s, 9H), 1.44 (s, 9H); $^{13}$C NMR (100 MHz, DMSO-d$_6$) δ 152.8, 146.8, 139.8, 136.0, 133.4, 133.2, 130.9, 130.7, 130.2, 130.1, 129.2, 129.0, 127.6, 125.3, 124.2, 122.1, 113.5, 90.5, 87.8, 85.4, 80.1, 27.9, 27.3; HRMS (ESI) calcd for C$_{27}$H$_{28}$ClN$_3$O$_4$Na (MNa$^+$) 516.1660. found 516.1659.

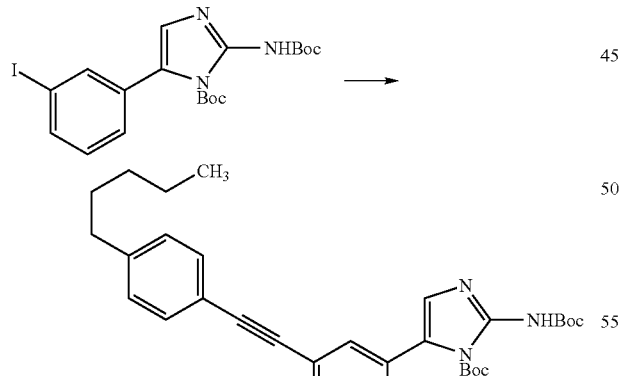

2-tert-butoxycarbonylamino-5-[3-(4-pentylphenyl-ethynyl)phenyl]imidazole-1-carboxylic acid tert-butyl ester In a similar manner, 0.100 g (0.206 mmol) of 2-tert-butoxycarbonylamino-5-(3-iodophenyl)imidazole-1-carboxylic acid tert-butyl ester afforded 0.099 g (91%) of 2-tert-butoxycarbonylamino-5-[3-(4-pentylphenylethynyl)phenyl]imidazole-1-carboxylic acid tert-butyl ester as a white foam: mp=51-52° C.; $^1$H NMR (300 MHz, DMSO-d$_6$) δ 9.58 (s, 1H), 8.03 (s, 1H), 7.98 (m, 1H), 7.82 (m, 1H), 7.40-7.50 (m, 4H), 7.25 (d, 2H, J=8.4 Hz), 2.60 (t, 2H, J=7.5 Hz), 1.59 (m, 2H), 1.57 (s, 9H), 1.44 (s, 9H), 1.24 (m, 4H), 0.861 (t, 3H, J=6.9 Hz); $^{13}$C NMR (100 MHz, DMSO-d$_6$) δ 152.8, 146.8, 143.5, 139.8, 136.1, 133.2, 131.3, 130.0, 129.1, 127.4, 124.8, 122.8, 119.5, 113.4, 89.6, 88.7, 85.3, 80.1, 35.0, 30.9, 30.4, 27.9, 27.3, 21.9, 13.9, HRMS (ESI) calcd for C$_{32}$H$_{39}$N$_3$O$_4$Na (MNa$^+$) 552.2832. found 552.2829.

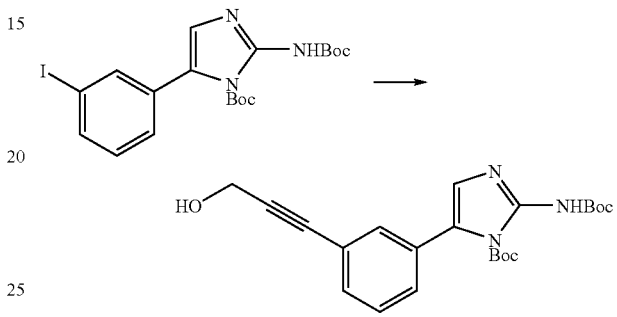

2-tert-butoxycarbonylamino-5-[3-(3-hydroxyprop-1-ynyl)phenyl]imidazole-1-carboxylic acid tert-butyl ester In a similar manner, 0.100 g (0.206 mmol) of 2-tert-butoxycarbonylamino-5-(3-iodophenyl)imidazole-1-carboxylic acid tert-butyl ester afforded 0.069 g (81%) of 2-tert-butoxycarbonylamino-5-[3-(3-hydroxyprop-1-ynyl)phenyl]imidazole-1-carboxylic acid tert-butyl ester as a white foam: mp=77-78° C.; $^1$H NMR (300 MHz, DMSO-d$_6$) δ 9.56 (s, 1H), 8.01 (s, 1H), 7.88 (m, 1H), 7.93 (m, 1H), 7.39 (t, 1H, J=7.8 Hz), 7.31 (m, 1H), 5.36 (t, 1H, J=5.7 Hz), 4.31 (d, 2H, J=6.0 Hz), 1.57 (s, 9H), 1.43 (s, 9H); $^{13}$C NMR (75 MHz, DMSO-d$_6$) δ 152.8, 146.8, 139.8, 136.1, 133.1, 129.9, 129.0, 127.4, 124.7, 122.8, 113.4, 89.9, 85.3, 83.5, 80.1, 49.1, 27.9, 27.3; HRMS (ESI) calcd for C$_{22}$H$_{27}$N$_3$O$_5$Na (MNa$^+$) 436.1842. found 436.1838.

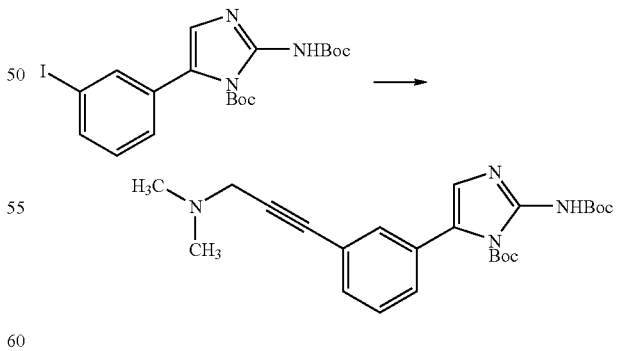

2-tert-butoxycarbonylamino-5-[3-(3-dimethylamino-prop-1-ynyl)phenyl]imidazole-1-carboxylic acid tert-butyl ester In a similar manner, 0.100 g (0.206 mmol) of 2-tert-butoxycarbonylamino-5-(3-iodophenyl)imidazole-1-carboxylic acid tert-butyl ester afforded 0.077 g (86%) of 2-tert-butoxycarbonylamino-5-[3-(3-dimethylaminoprop-1-ynyl)phenyl]imidazole-1-carboxylic acid tert-butyl ester as a white foam: mp=68-69° C.; $^1$H NMR (300 MHz, DMSO-d$_6$) δ 9.57 (s, 1H), 8.00 (s, 1H), 7.87 (m, 1H), 7.79 (m, 1H), 7.38 (t, 1H, J=7.5 Hz), 7.33 (m, 1H), 3.47 (s, 2H), 2.26 (s, 6H), 1.57 (s, 9H), 1.43 (s, 9H); $^{13}$C NMR (100 MHz, DMSO-d$_6$) δ 152.9, 146.8, 139.7, 136.1, 133.1, 132.0, 131.5, 131.4, 130.1, 129.0, 128.8, 128.7, 127.4, 124.6, 122.9, 113.4, 85.4, 85.3, 84.9, 80.1, 47.7, 43.8, 27.9, 27.3; HRMS (ESI) calcd for C$_{24}$H$_{32}$N$_4$O$_4$Na (MNa$^+$) 463.2315. found 463.2317.

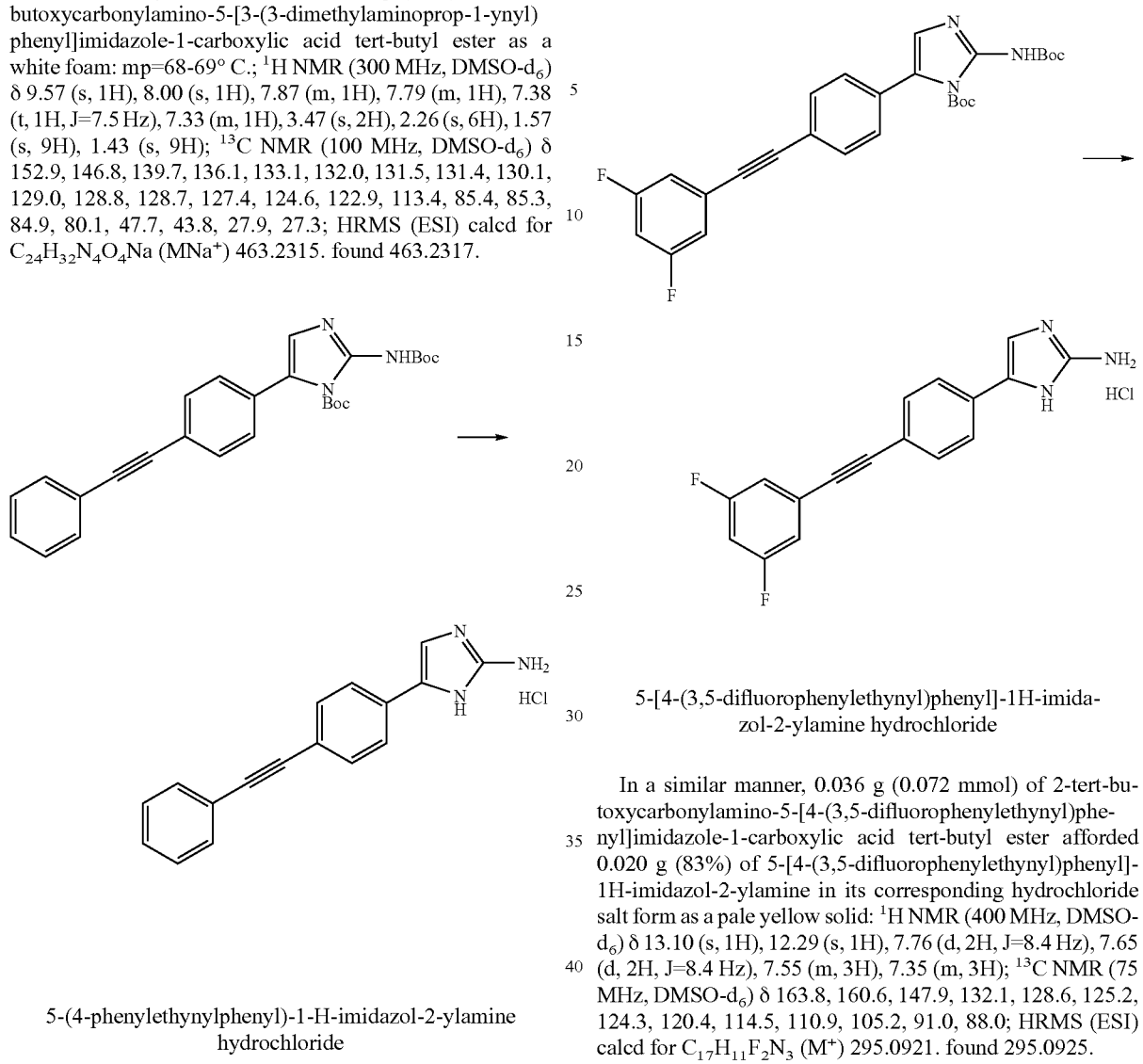

5-(4-phenylethynylphenyl)-1-H-imidazol-2-ylamine hydrochloride 2-tert-butoxycarbonylamino-5-(4-phenylethynylphenyl)imidazole-1-carboxylic acid tert-butyl ester (0.039 g, 0.109 mmol) was dissolved in anhydrous dichloromethane (5 mL) and cooled to 0° C. Trifluoroacetic acid (0.250 mL) was added drop-wise while the reaction continued to stir at 0° C. Upon completion, the reaction was allowed to warm to room temperature over the course of 12 h. Toluene (2 mL) was added and the reaction was evaporated to dryness. The crude TFA salt was then dissolved in dichloromethane (3 mL) and a 2M solution of HCl in diethyl ether (0.10 mL) was added. The solution was again concentrated under reduced pressure and the resulting product triturated with cold diethyl ether (5 mL) to afford 0.031 g (97%) of 5-(4-phenylethynylphenyl)-1H-imidazol-2-ylamine in its corresponding hydrochloride salt form as a brown solid: $^1$H NMR (300 MHz, DMSO-d$_6$) δ 13.06 (s, 1H), 12.27 (s, 1H), 7.74 (d, 2H, J=8.7 Hz), 7.62 (d, 2H, J=8.7 Hz), 7.55 (m, 5H), 7.43 (m, 3H); $^{13}$C NMR (75 MHz, DMSO-d$_6$) δ 147.9, 131.9, 131.2, 128.9, 128.7, 127.9, 125.7, 124.3, 122.1, 121.4, 110.6, 90.3, 89.0; HRMS (ESI) calcd for C$_{17}$H$_{13}$N$_3$ (M$^+$) 259.1110. found 259.1113.

5-[4-(3,5-difluorophenylethynyl)phenyl]-1H-imidazol-2-ylamine hydrochloride

In a similar manner, 0.036 g (0.072 mmol) of 2-tert-butoxycarbonylamino-5-[4-(3,5-difluorophenylethynyl)phenyl]imidazole-1-carboxylic acid tert-butyl ester afforded 0.020 g (83%) of 5-[4-(3,5-difluorophenylethynyl)phenyl]-1H-imidazol-2-ylamine in its corresponding hydrochloride salt form as a pale yellow solid: $^1$H NMR (400 MHz, DMSO-d$_6$) δ 13.10 (s, 1H), 12.29 (s, 1H), 7.76 (d, 2H, J=8.4 Hz), 7.65 (d, 2H, J=8.4 Hz), 7.55 (m, 3H), 7.35 (m, 3H); $^{13}$C NMR (75 MHz, DMSO-d$_6$) δ 163.8, 160.6, 147.9, 132.1, 128.6, 125.2, 124.3, 120.4, 114.5, 110.9, 105.2, 91.0, 88.0; HRMS (ESI) calcd for C$_{17}$H$_{11}$F$_2$N$_3$ (M$^+$) 295.0921. found 295.0925.

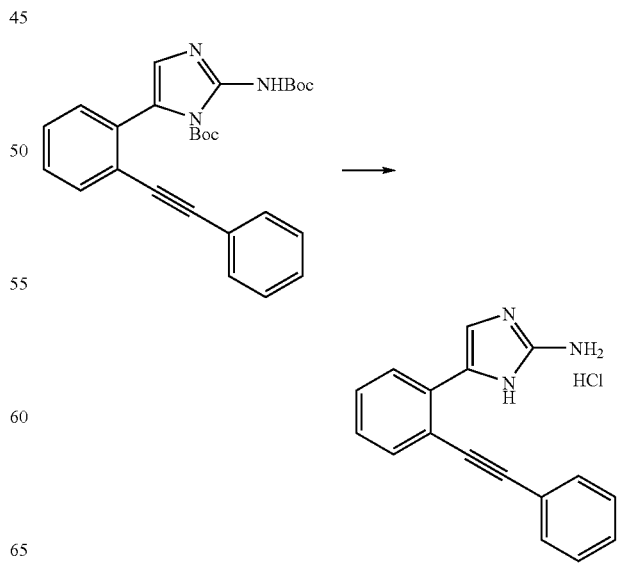

5-(2-phenylethynylphenyl)-1H-imidazol-2-ylamine hydrochloride)

In a similar manner, 0.046 g (0.127 mmol) of 2-tert-butoxycarbonylamino-5-(2-phenylethynylphenyl)imidazole-1-carboxylic acid tert-butyl ester afforded 0.037 g (97%) of 5-(2-phenylethynylphenyl)-1H-imidazol-2-ylamine in its corresponding hydrochloride salt form as a brown amorphous solid: $^1$H NMR (300 MHz, DMSO-$d_6$) δ 12.87 (s, 1H), 12.12 (s, 1H), 7.51-7.73 (m, 8H), 7.46 (m, 4H); $^{13}$C NMR (75 MHz, DMSO-$d_6$) δ 147.3, 133.5, 131.3, 129.2, 129.1, 128.6, 128.2, 126.9, 124.3, 121.9, 118.9, 112.2, 94.0, 88.2; HRMS (ESI) calcd for $C_{17}H_{13}N_3$ (M$^+$) 259.1110. found 259.1110.

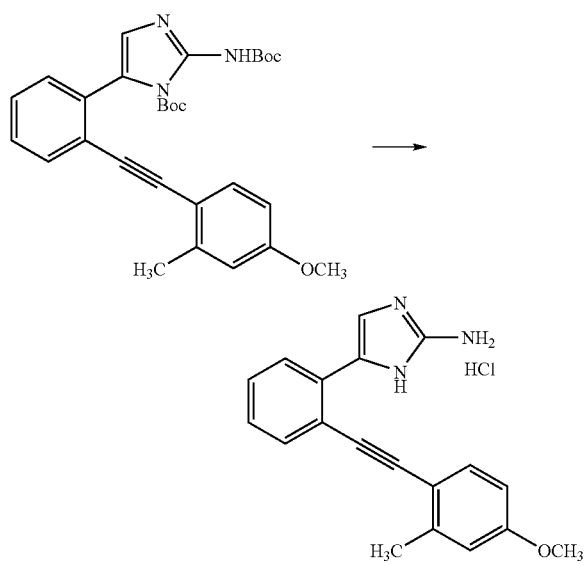

5-[2-(4-methoxy-2-methylphenylethynyl)phenyl]-1H-imidazol-2-ylamine hydrochloride In a similar manner, 0.039 g (0.077 mmol) of 2-tert-butoxycarbonylamino-5-[2-(4-methoxy-2-methylphenylethynyl)phenyl]imidazole-1-carboxylic acid tert-butyl ester afforded 0.024 g (92%) of 5-[2-(4-methoxy-2-methylphenylethynyl)phenyl]-1H-imidazol-2-ylamine in its corresponding hydrochloride salt form as a tan amorphous solid: $^1$H NMR (300 MHz, DMSO-$d_6$) δ 14.03 (s, 1H), 12.67 (s, 1H), 8.34 (d, 1H, J=8.1 Hz), 8.03 (d, 1H, J=8.1 Hz), 8.00 (br s, 2H), 7.66 (m, 3H), 7.51 (m, 1H), 7.26 (d, 1H, J=8.1 Hz), 7.00 (d, 1H, J=2.7 Hz), 6.92 (dd, 1H, J=2.7, 8.1 Hz), 3.83 (s, 3H), 2.14 (s, 3H); $^{13}$C NMR (75 MHz, DMSO-$d_6$) δ 159.3, 150.3, 137.5, 131.1, 129.8, 128.7, 128.1, 126.7, 125.5, 125.2, 124.1, 124.0, 120.7, 119.1, 115.7, 111.6, 55.2, 19.9; HRMS (ESI) calcd for $C_{19}H_{17}N_3O$ (M$^+$) 303.1372. found 303.1371.

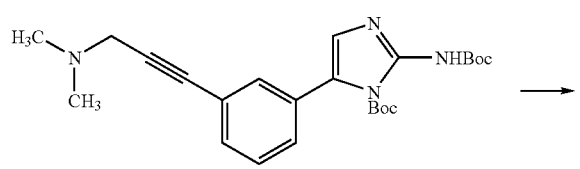

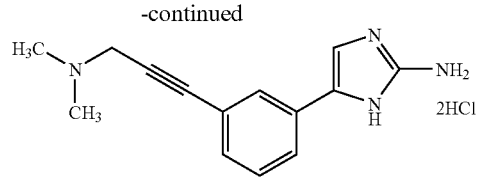

5-[3-(3-dimethylaminoprop-1-ynyl)-phenyl]-1H-imidazol-2-ylamine dihydrochloride In a similar manner, 0.036 g (0.082 mmol) of 2-tert-butoxycarbonylamino-5-[3-(3 dimethylaminoprop-1-ynyl)phenyl]imidazole-1-carboxylic acid tert-butyl ester afforded 0.025 g (99%) of 5-[3-(3-dimethylaminoprop-1-ynyl)-phenyl]-1H-imidazol-2-ylamine in its corresponding dihydrochloride salt form as a yellow solid: $^1$H NMR (300 MHz, DMSO-$d_6$) δ 13.18 (s, 1H), 12.30 (s, 1H), 11.43 (s, 1H), 7.91 (s, 1H), 7.67 (m, 1H), 7.50 (m, 5H), 4.33 (s, 2H), 2.86 (s, 6H); $^{13}$C NMR (75 MHz, DMSO-$d_6$) δ 147.9, 131.0, 129.6, 128.5, 127.1, 125.4, 125.2, 121.6, 110.6, 88.2, 79.7, 46.1, 41.6; HRMS (ESI) calcd for $C_{17}H_{13}N_3$ (M$^+$) 240.1375. found 240.1366.

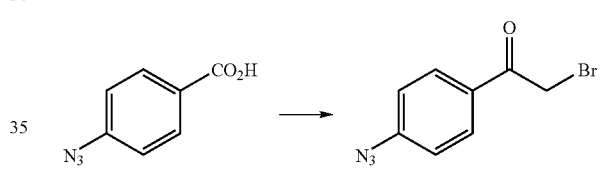

1-(4-azidophenyl)-2-bromoethanone 4-azidobenzoic acid (2.71 g, 10.0 mmol) was dissolved in anhydrous dichloromethane (80 mL) and cooled to 0° C. Oxalyl chloride (4.40 mL, 50.0 mmol) was added drop-wise followed by the addition of a catalytic amount of anhydrous DMF (0.01 mL). The reaction was allowed to warm to room temperature over the course of 1 h and after that time the solution was evaporated to dryness. The crude acid chloride was dissolved in anhydrous dichloromethane (10 mL) added drop-wise to a 0° C. solution of $CH_2N_2$ (50.0 mmol generated from Diazald®/KOH) in diethyl ether (150 mL). This solution was stirred at 0° C. for 1 h upon which the reaction was quenched via the drop-wise addition of 48% solution of concentrated HBr (6.0 mL). The reaction mixture was diluted with dichloromethane (15 mL) and immediately washed with sat. NaHCO$_3$ (3×25 mL) and brine (2×25 mL) before being dried (MgSO$_4$), filtered and concentrated. The crude oil was purified via flash column chromatography (10-50% EtOAc/Hexanes) to obtain the desired compound 1-(4-azidophenyl)-2-bromoethanone (3.84 g, 96%) as a pale yellow solid: $^1$H NMR (400 MHz, DMSO-$d_6$) δ 8.04 (m, 2H), 7.28 (m, 2H), 4.90 (s, 2H); $^{13}$C NMR (100 MHz, DMSO-$d_6$) δ 190.4, 145.0, 130.9, 130.5, 119.4, 33.8; HRMS (ESI) calcd for $C_8H_6BrN_3O$ (M$^+$) 238.9694. found 238.9688.

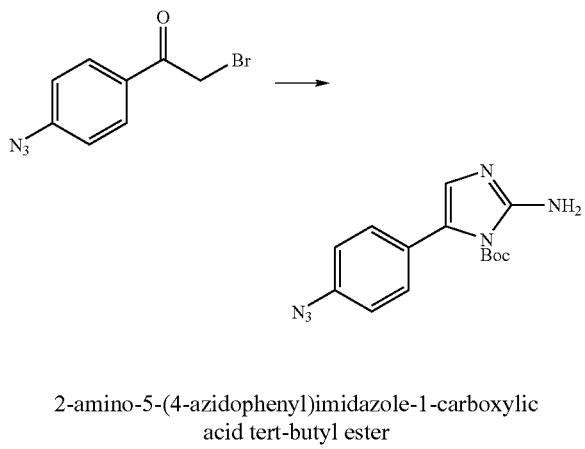

2-amino-5-(4-azidophenyl)imidazole-1-carboxylic acid tert-butyl ester

To a solution of 1-(4-azidophenyl)-2-bromoethanone (1.50 g, 6.24 mmol) in anhydrous DMF (20 mL) was added Boc-guanidine (3.00 g, 18.7 mmol). The reaction was stirred at ambient temperature for 48 hours upon which the mixture was partitioned between EtOAc (150 mL) and water (75 mL). The organic layer was successively washed with water (3×50 mL) and brine (2×50 mL) before being dried (Na$_2$SO$_4$) and evaporated to dryness. The resulting crude oil was purified via flash column chromatography (10-50% EtOAc/Hexanes) to obtain the target 2-amino-5-(4-azidophenyl)imidazole-1-carboxylic acid tert-butyl ester (1.84 g, 58%) as a yellow solid: $^1$H NMR (300 MHz, DMSO-d$_6$) δ 7.77 (d, 2H, J=8.1 Hz), 7.36 (s, 1H), 7.10 (dd, 2H, J=0.9, 8.1 Hz), 6.61 (br s, 2H), 1.58 (s, 9H); $^{13}$C NMR (75 MHz, DMSO-d$_6$) δ 150.4, 148.9, 137.6, 136.2, 130.5, 126.2, 119.1, 106.2, 84.7, 27.5; HRMS (ESI) calcd for C$_8$H$_6$BrN$_3$O (M$^+$) 300.1335. found 300.1329.

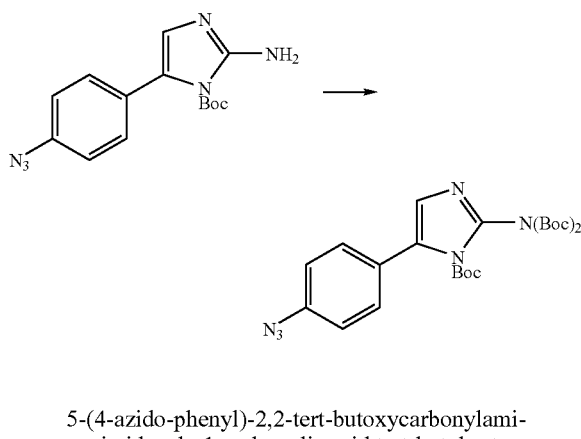

5-(4-azido-phenyl)-2,2-tert-butoxycarbonylaminoimidazole-1-carboxylic acid tert-butyl ester 2-amino-5-(4-azidophenyl)imidazole-1-carboxylic acid tert-butyl ester (0.155 g, 0.516 mmol) and Boc anhydride (0.563 g, 2.58 mmol) were dissolved in anhydrous THF (8 mL) at room temperature. Triethylamine (1.05 mL, 7.74 mmol) and a catalytic amount of DMAP (0.003 g) were added and the reaction was allowed to stir for 16 h. After that time, the solution was poured into ethyl acetate (50 mL) and washed with 1N aq. HCl (3×10 mL), sat. aq. NaHCO$_3$ (3×10 mL), and brine (1×10 mL). The combined organics were dried (Na$_2$SO$_4$), filtered, and evaporated to yield the crude product which was purified by flash column chromatography (10-30% EtOAc/Hexanes) to give 0.200 g (78%) of the title compound 5-(4-azido-phenyl)-2,2-tert-butoxycarbonylaminoimidazole-1-carboxylic acid tert-butyl ester as a tan foam: $^1$H NMR (400 MHz, DMSO-d$_6$) δ 8.13 (s, 1H), 7.89 (dd, 2H, J=0.8, 8.8 Hz), 7.14 (dd, 2H, J=0.8, 8.8 Hz), 1.56 (s, 9H), 1.37 (s, 18H); $^{13}$C NMR (75 MHz, DMSO-d$_6$) δ 149.0, 145.9, 138.5, 137.9, 137.3, 129.2, 126.4, 119.4, 114.0, 86.2, 83.4, 27.4, 27.3; HRMS (ESI) calcd for C$_{24}$H$_{32}$N$_6$O$_6$ (M$^+$) 500.2383. found 500.2374.

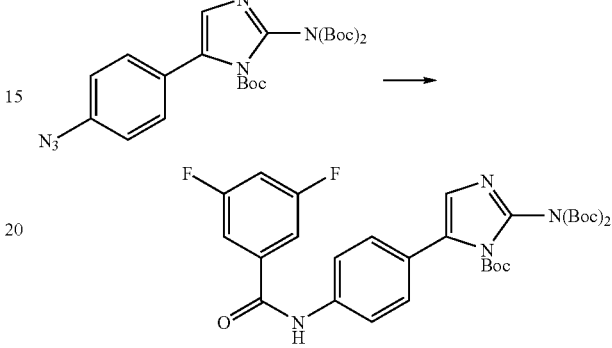

2,2-tert-butoxycarbonylamino-5-[4-(3,5-difluorobenzoylamino)phenyl]imidazole-1-carboxylic acid tert-butyl ester To a solution of anhydrous THF (5 mL) and 10% Pd/C (0.010 g) was charged 5-(4-azido-phenyl)-2,2-tert-butoxycarbonylaminoimidazole-1-carboxylic acid tert-butyl ester (0.100 g, 0.200 mmol). Air was removed from the system and the reaction was back flushed with hydrogen. This process was repeated three times before setting the reaction under a hydrogen balloon at atmospheric pressure and temperature for 12 h. After that time, the reaction was filtered to remove the catalyst. The filtrate was cooled to −78° C. and triethylamine (0.027 mL, 0.200 mmol) was added prior to the dropwise addition of 3,5-difluorobenzoyl chloride (0.035 g, 0.200 mmol) diluted in anhydrous dichloromethane (0.50 mL). The reaction was stirred at −78° C. for 30 mins and then quenched with methanol (1 mL) before being concentrated under reduced pressure and purified by flash column chromatography (10-40% EtOAc/Hexanes) to obtain the title compound 2,2-tert-butoxycarbonylamino-5-[4-(3,5-difluorobenzoylamino)phenyl]imidazole-1-carboxylic acid tert-butyl ester (0.094 g, 77%) as a pale yellow solid: $^1$H NMR (300 MHz, DMSO-d$_6$) δ 10.42 (s, 1H), 8.08 (s, 1H), 7.82 (m, 4H), 7.69 (m, 2H), 7.54 (m, 1H), 1.57 (s, 9H), 1.38 (s, 18H); $^{13}$C NMR (100 MHz, CD$_3$OD) δ 165.8, 163.2, 151.0, 147.7, 140.1, 139.6, 130.0, 126.7, 122.4, 114.7, 111.9, 108.1, 88.2, 85.7, 28.3; HRMS (ESI) calcd for C$_{31}$H$_{36}$F$_2$N$_4$O$_7$ (M$^+$) 614.2552. found 614.2554.

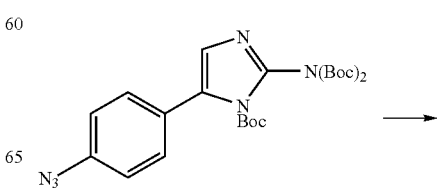

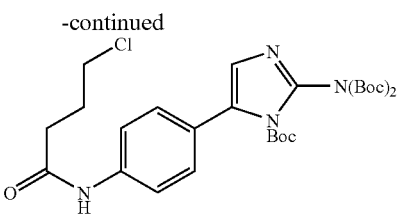

2,2-tert-butoxycarbonylamino-5-[4-(4-chlorobutyrylamino)phenyl]imidazole-1-carboxylic acid tert-butyl ester In a similar manner, 0.100 g (0.200 mmol) of 5-(4-azidophenyl)-2,2-tert-butoxycarbonylaminoimidazole-1-carboxylic acid tert-butyl ester afforded 0.074 g (64%) of 2,2-tert-butoxycarbonylamino-5-[4-(4-chlorobutyrylamino)phenyl]imidazole-1-carboxylic acid tert-butyl ester as a tan solid: $^1$H NMR (300 MHz, DMSO-$d_6$) δ 10.04 (s, 1H), 8.00 (s, 1H), 7.77 (d, 2H, J=8.4 Hz), 7.60 (d, 2H, J=8.4 Hz), 3.69 (t, 2H, J=6.3 Hz), 2.48 (m, 2H), 2.00 (m, 2H), 1.55 (s, 9H), 1.36 (s, 18H); $^{13}$C NMR (100 MHz, CD$_3$OD) δ 173.3, 151.0, 147.7, 140.0, 129.2, 126.7, 121.4, 114.4, 88.2, 85.6, 88.2, 85.6, 45.3, 35.0, 29.7, 28.3; HRMS (ESI) calcd for $C_{28}H_{39}ClN_4O_7$ (M$^+$) 578.2507. found 578.2510.

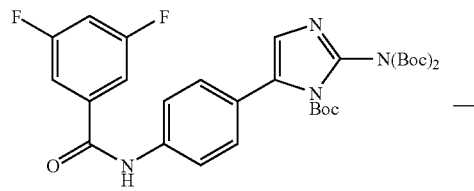

4-(2-amino-3H-imidazol-4-yl)phenyl]-3,5-difluorobenzamide hydrochloride 2,2-tert-butoxycarbonylamino-5-[4-(3,5-difluorobenzoylamino)phenyl]imidazole-1-carboxylic acid tert-butyl ester (0.046 g, 0.078 mmol) was dissolved in anhydrous dichloromethane (5 mL) and cooled to 0° C. Trifluoroacetic acid (0.50 mL) was added drop-wise while the reaction continued to stir at 0° C. Upon completion, the reaction was allowed to warm to room temperature over the course of 12 h. Toluene (2 mL) was added and the reaction was evaporated to dryness. The crude TFA salt was then dissolved in dichloromethane (3 mL) and a 2M solution of HCl in diethyl ether (0.10 mL) was added. The solution was again concentrated under reduced pressure and the resulting product triturated with cold diethyl ether (5 mL) to afford 0.026 g (99%) of 4-(2-amino-3H-imidazol-4-yl)phenyl]-3,5-difluorobenzamide in its corresponding hydrochloride salt form as a white solid: $^1$H NMR (300 MHz, DMSO-$d_6$) δ 12.94 (s, 1H), 12.14 (s, 1H), 10.57 (s, 1H), 7.85 (d, 2H, J=8.4 Hz), 7.72 (m, 2H), 7.66 (d, 2H, J=8.4 Hz), 7.48 (br s, 2H), 7.35 (s, 1H); $^{13}$C NMR (100 MHz, CD$_3$OD) δ 165.8, 149.6, 140.0, 139.8, 128.8, 126.2, 125.3, 122.6, 112.2, 111.9, 109.7, 108.1; HRMS (ESI) calcd for $C_{16}H_{12}F_2N_4O$ (M$^+$) 314.0979. found 314.0977.

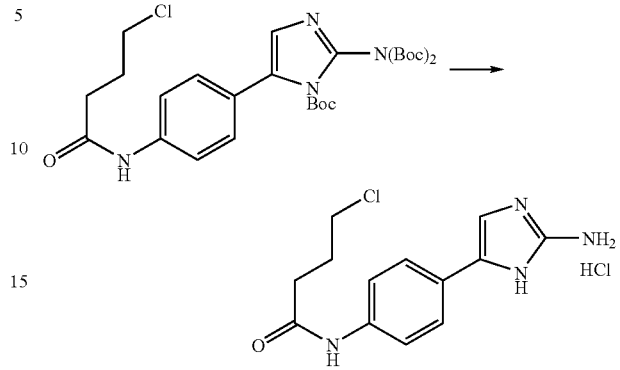

4-(2-amino-3H-imidazol-4-yl)phenyl]-4-chlorobutyramide hydrochloride

In a similar manner, 0.051 g (0.089 mmol) of 2,2-tert-butoxycarbonylamino-5-[4-(4-chlorobutyrylamino)phenyl]imidazole-1-carboxylic acid tert-butyl ester afforded 0.026 g (96%) of 4-(2-amino-3H-imidazol-4-yl)phenyl]-4-chlorobutyramide in its corresponding hydrochloride salt form as a tan solid: $^1$H NMR (300 MHz, DMSO-$d_6$) δ 12.82 (s, 1H), 12.07 (s, 1H), 10.19 (s, 1H), 7.65 (d, 2H, J=9.0 Hz), 7.57 (d, 2H, J=8.7 Hz), 7.45 (br s, 2H), 7.29 (s, 1H), 3.70 (d, 2H, J=6.3 Hz), 2.47 (m, 2H), 2.03 (m, 2H); $^{13}$C NMR (100 MHz, CD$_3$OD) δ 173.5, 148.5, 140.4, 129.0, 126.3, 124.6, 121.6, 109.4, 45.3, 35.0, 29.7; HRMS (ESI) calcd for $C_{13}H_{15}ClN_4O$ (M$^+$) 278.0934. found 278.0931.

cyclopropanecarboxylic acid [4-(2-amino-3H-imidazol-4-yl)phenyl]amide hydrochloride In a similar manner, 0.060 g (0.111 mmol) of 2,2-tert-butoxycarbonylamino-5-[4-(cyclopropanecarbonylamino)phenyl]imidazole-1-carboxylic acid tert-butyl ester afforded 0.030 g (99%) of cyclopropanecarboxylic acid [4-(2-amino-3H-imidazol-4-yl)phenyl]amide in its corresponding hydrochloride salt form as a tan amorphous solid: $^1$H NMR (400 MHz, DMSO-$d_6$) δ 12.78 (s, 1H), 12.05 (s, 1H), 10.41 (s, 1H), 7.67 (d, 2H, J=8.0 Hz), 7.56 (d, 2H, J=8.0 Hz), 7.45 (br s, 2H), 7.28 (s, 1H), 1.84 (m, 1H), 0.80 (m, 4H); $^{13}$C NMR (100 MHz, CD$_3$OD) δ 175.2, 163.2, 149.3, 140.7, 126.3, 124.4, 121.4, 109.4, 15.8, 8.29; HRMS (ESI) calcd for $C_{13}H_{14}N_4O$ (M$^+$) 242.1168. found 242.1160.

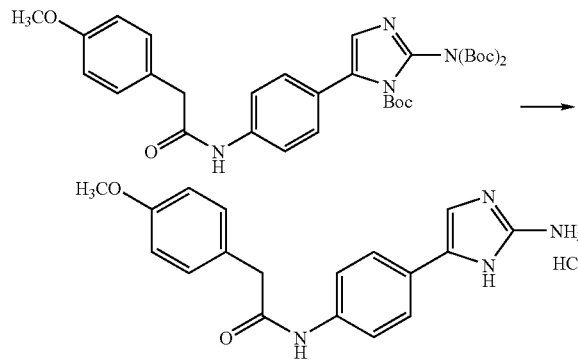

4-(2-amino-3H-imidazol-4-yl)phenyl-2-(4-methoxyphenyl)acetamide hydrochloride

In a similar manner, 0.041 g (0.066 mmol) of 2,2-tert-butoxycarbonylamino-5-{4-[2-(4-methoxyphenyl)acetylamino]phenyl}imidazole-1-carboxylic acid tert-butyl ester afforded 0.023 g (99%) of 4-(2-amino-3H-imidazol-4-yl)phenyl-2-(4-methoxyphenyl)acetamide in its corresponding hydrochloride salt form as a tan solid: $^1$H NMR (300 MHz, DMSO-d$_6$) δ 12.80 (s, 1H), 12.06 (s, 1H), 10.36 (s, 1H), 7.65 (d, 2H, J=8.7 Hz), 7.56 (d, 2H, J=8.7 Hz), 7.44 (br s, 2H), 7.24 (m, 3H), 6.86 (d, 2H, J=8.7 Hz), 3.71 (s, 3H), 3.57 (s, 2H); $^{13}$C NMR (100 MHz, CD$_3$OD) δ 160.3, 149.3, 140.3, 131.2, 129.2, 128.8, 127.3, 126.2, 124.7, 121.6, 115.1, 109.7, 55.8, 43.9; HRMS (ESI) calcd for $CO_{18}H_{18}N_4O_2$ (M$^+$) 322.1430. found 322.1428.

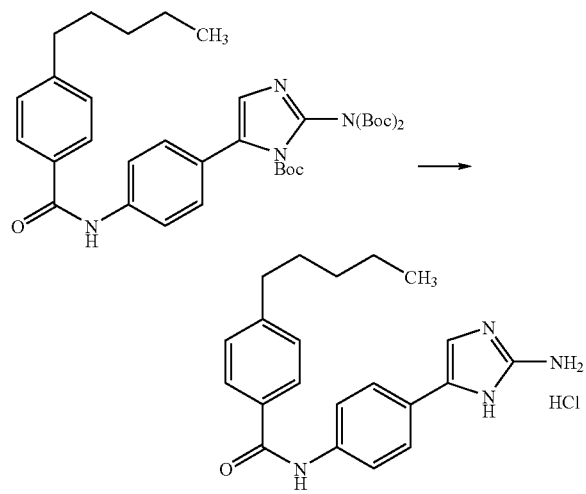

4-(2-amino-3H-imidazol-4-yl)phenyl]-4-pentylbenzamide hydrochloride

In a similar manner, 0.085 g (0.131 mmol) of 2,2-tert-butoxycarbonylamino-5-[4-(4-pentylbenzoylamino)phenyl]imidazole-1-carboxylic acid tert-butyl ester afforded 0.050 g (99%) of 4-(2-amino-3H-imidazol-4-yl)phenyl]-4-pentylbenzamide in its corresponding hydrochloride salt form as a tan amorphous solid: $^1$H NMR (400 MHz, DMSO-d$_6$) δ 13.09 (s, 1H), 12.23 (s, 1H), 10.36 (s, 1H), 7.86 (m, 4H), 7.64 (d, 2H, J=8.8 Hz), 7.52 (br s, 2H), 7.33 (m, 3H), 2.62 (t, 2H, J=7.6 Hz), 1.60 (m, 2H), 1.28 (m, 4H), 0.83 (t, 3H, J=5.7 Hz); $^{13}$C NMR (100 MHz, CD$_3$OD) δ 167.7, 147.6, 139.2, 133.6, 131.0, 129.8, 129.6, 128.9, 126.2, 124.9, 122.6, 108.2, 35.6, 31.4, 30.9, 22.4, 13.2; HRMS (ESI) calcd for $C_{21}H_{24}N_4O$ (M$^+$) 348.1950. found 348.1939.

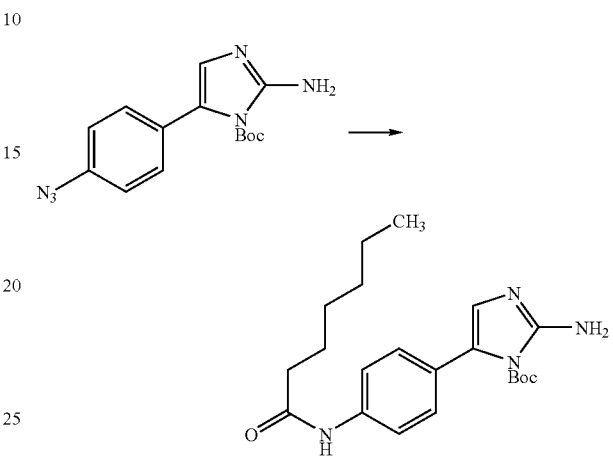

2-amino-5-(4-heptanoylaminophenyl)imidazole-1-carboxylic acid tert-butyl ester

To a solution of anhydrous THF (5 mL) and 10% Pd/C (0.010 g) was charged 2-amino-5-(4-azidophenyl)imidazole-1-carboxylic acid tert-butyl ester (0.100 g, 0.332 mmol). Air was removed from the system and the reaction was back flushed with hydrogen. This process was repeated three times before setting the reaction under a hydrogen balloon at atmospheric pressure and temperature for 12 h. After that time, the reaction was filtered to remove the catalyst. The filtrate was cooled to –78° C. and triethylamine (0.046 mL, 0.332 mmol) was added prior to the drop-wise addition of heptanoyl chloride (0.049 g, 0.332 mmol) diluted in anhydrous dichloromethane (0.50 mL). The reaction was stirred at –78° C. for 30 mins and then quenched with methanol (1 mL) before being concentrated under reduced pressure and purified by flash column chromatography (10-60% EtOAc/Hexanes) to obtain the title compound 2-amino-5-(4-heptanoylaminophenyl)imidazole-1-carboxylic acid tert-butyl ester (0.124 g, 97%) as a yellow solid: $^1$H NMR (300 MHz, DMSO-d$_6$) δ 10.08 (s, 1H), 8.14 (br s, 2H), 7.67 (m, 4H), 7.56 (s, 1H), 2.32 (t, 2H, J=7.5 Hz), 1.49 (m, 11H), 1.28 (br s, 6H), 0.87 (t, 2H, J=6.0 Hz); $^{13}$C NMR (75 MHz, DMSO-d$_6$) δ 171.4, 147.5, 139.1, 126.4, 124.7, 122.2, 119.2, 119.0, 111.4, 108.4, 36.4, 31.0, 28.3, 27.4, 25.0, 21.9, 13.9; HRMS (ESI) calcd for $C_{21}H_{30}N_4O_3$ (M$^+$) 386.2318. found

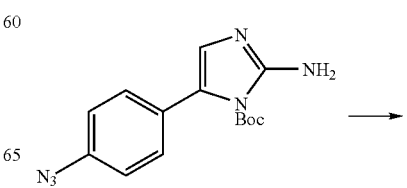

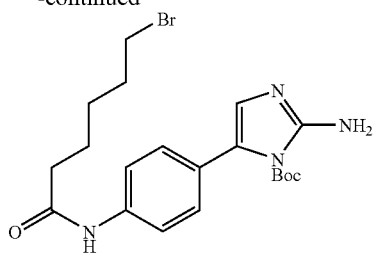

2-amino-5-[4-(6-bromohexanoylamino)phenyl]imidazole-1-carboxylic acid tert-butyl ester In a similar manner, 0.100 g (0.332 mmol) of 2-amino-5-(4-azidophenyl)imidazole-1-carboxylic acid tert-butyl ester afforded 0.124 g (83%) of 2-amino-5-[4-(6-bromohexanoylamino)phenyl]imidazole-1-carboxylic acid tert-butyl ester as a pale yellow foam: $^1$H NMR (300 MHz, DMSO-$d_6$) δ 9.89 (s, 1H), 7.63 (d, 2H, J=8.4 Hz), 7.57 (d, 2H, J=8.0 Hz), 7.24 (s, 1H), 6.58 (br s, 2H), 3.53 (m, 2H), 2.30 (t, 2H, J=7.2 Hz), 1.82 (tt, 2H, J=6.8, 13.6 Hz), 1.57 (m, 11H), 1.41 (m, 2H); $^{13}$C NMR (100 MHz, DMSO-$d_6$) δ 171.6, 151.1, 149.9, 137.7, 129.6, 126.0, 120.3, 106.3, 85.7, 37.8, 34.2, 32.9, 28.5, 28.2, 25.1; HRMS (ESI) calcd for $C_{20}H_{27}N_4O_3$ (M$^+$) 450.1267. found 450.1258.

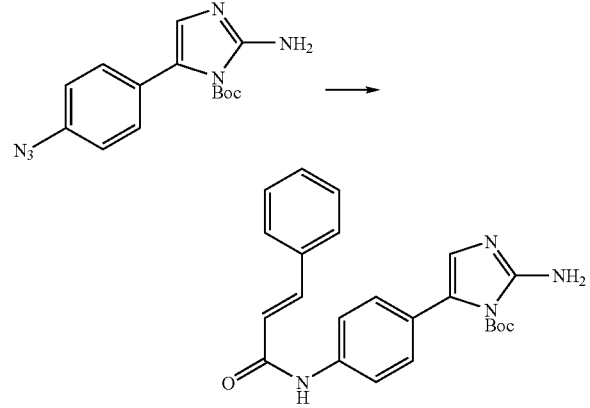

2-amino-5-[4-(3-phenylacryloylamino)phenyl]imidazole-1-carboxylic acid tert-butyl ester In a similar manner, 0.100 g (0.332 mmol) of 2-amino-5-(4-azidophenyl)imidazole-1-carboxylic acid tert-butyl ester afforded 0.078 g (58%) of 2-amino-5-[4-(3-phenylacryloylamino)phenyl]imidazole-1-carboxylic acid tert-butyl ester as a tan amorphous solid: $^1$H NMR (400 MHz, DMSO-$d_6$) δ 10.25 (s, 1H), 7.68 (m, 7H), 7.43 (m, 3H), 7.28 (s, 1H), 6.83 (d, 1H, J=15.2 Hz), 6.60 (br s, 2H), 1.58 (s, 9H); $^{13}$C NMR (100 MHz, CDCl$_3$) δ 164.3, 150.7, 149.6, 142.4, 137.6, 137.4, 134.9, 130.1, 129.5, 129.0, 128.1, 125.9, 121.2, 120.2, 106.1, 85.4, 28.2; HRMS (ESI) calcd for $C_{23}H_{24}N_4O_3$ (M$^+$) 404.1848. found 484.1850.

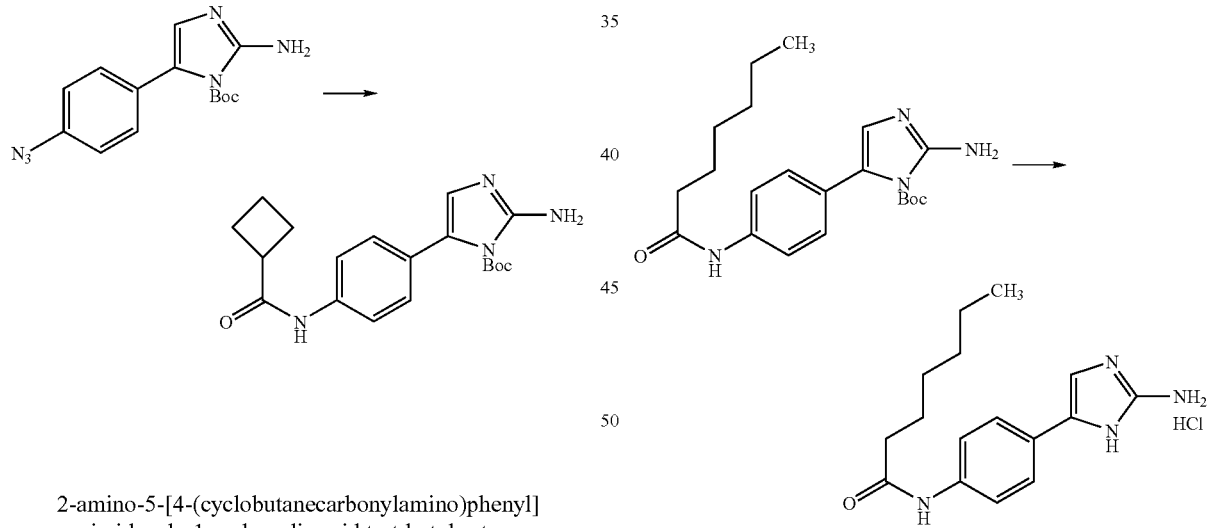

2-amino-5-[4-(cyclobutanecarbonylamino)phenyl]imidazole-1-carboxylic acid tert-butyl ester In a similar manner, 0.100 g (0.332 mmol) of 2-amino-5-(4-azidophenyl)imidazole-1-carboxylic acid tert-butyl ester afforded 0.088 g (75%) of 2-amino-5-[4-(cyclobutanecarbonylamino)phenyl]imidazole-1-carboxylic acid tert-butyl ester as a white foam: $^1$H NMR (400 MHz, DMSO-$d_6$) δ 9.73 (s, 1H), 7.63 (d, 2H, J=8.0 Hz), 7.57 (d, 2H, J=8.0 Hz), 7.25 (s, 1H), 6.58 (br s, 2H), 3.21 (m, 1H), 2.21 (m, 2H), 2.10 (m, 2H), 1.94 (m, 1H), 1.81 (m, 1H), 1.58 (s, 9H); $^{13}$C NMR (100 MHz, DMSO-$d_6$) δ 173.4, 150.7, 149.6, 137.5, 129.2, 125.9, 125.7, 119.8, 105.9, 85.4, 41.0, 28.2, 25.5, 18.2; HRMS (ESI) calcd for $C_{19}H_{24}N_4O_3$ (M$^+$) 356.1848. found 356.1844.

heptanoic acid [4-(2-amino-3H-imidazol-4-yl)phenyl]amide hydrochloride 2-amino-5-(4-heptanoylaminophenyl)imidazole-1-carboxylic acid tert-butyl ester (0.089 g, 0.230 mmol) was dissolved in anhydrous dichloromethane (5 mL) and cooled to 0° C. Trifluoroacetic acid (0.50 mL) was added drop-wise while the reaction continued to stir at 0° C. Upon completion, the reaction was allowed to warm to room temperature over the course of 12 h. Toluene (2 mL) was added and the reaction was evaporated to dryness. The crude TFA salt was then dissolved in dichloromethane (3 mL) and a 2M solution of HCl in diethyl ether (0.10 mL) was added. The solution was again concentrated under reduced pressure and the resulting product triturated with cold diethyl ether (5 mL) to afford 0.072 g (97%) of the desired compound heptanoic acid [4-(2-amino-3H-imidazol-4-yl)phenyl]amide in its corresponding hydrochloride form as a yellow amorphous solid: $^1$H NMR (300 MHz, DMSO-$d_6$) δ 12.80 (s, 1H), 12.05 (s, 1H), 10.08 (s, 1H), 7.67 (d, 2H, J=8.1 Hz), 7.59 (d, 2H, J=8.1 Hz), 7.43 (br s, 2H), 7.27 (s, 1H), 2.31 (t, 2H, J=6.8 Hz), 1.58 (m, 2H), 1.27 (m, 6H), 0.86 (t, 3H, J=5.7 Hz); $^{13}$C NMR (75 MHz, DMSO-$d_6$) δ 172.1, 148.2, 139.8, 127.1, 125.4, 123.0, 119.9, 109.1, 37.1, 31.7, 29.0, 25.7, 22.7, 14.6; HRMS (ESI) calcd for $C_{16}H_{22}N_4O$ (M$^+$) 286.1794. found 286.1788.

6-bromohexanoic acid [4-(2-amino-3H-imidazol-4-yl)phenyl]amide hydrochloride In a similar manner, 0.046 g (0.101 mmol) of 2-amino-5-[4-(6-bromohexanoylamino)phenyl]imidazole-1-carboxylic acid tert-butyl ester afforded 0.039 g (99%) of 6-bromohexanoic acid [4-(2-amino-3H-imidazol-4-yl)phenyl]amide in its corresponding hydrochloride salt form as a yellow solid: $^1$H NMR (400 MHz, DMSO-$d_6$) δ 12.80 (s, 1H), 12.05 (s, 1H), 10.10 (s, 1H), 7.65 (d, 2H, J=8.7 Hz), 7.56 (d, 2H, J=8.7 Hz), 7.44 (br s, 2H), 7.28 (s, 1H), 3.54 (t, 2H, J=6.4 Hz), 2.33 (t, 2H, J=7.2 Hz), 1.82 (tt, 2H, J=6.8, 14.0 Hz), 1.61 (tt, 2H, J=6.8, 14.8 Hz), 1.41 (tt, 2H, J=7.6, 14.8 Hz); $^{13}$C NMR (100 MHz, CD$_3$OD) δ 175.0, 148.1, 140.8, 129.3, 126.6, 124.9, 121.9, 109.8, 38.2, 34.6, 34.1, 29.3, 26.4; HRMS (ESI) calcd for $C_{15}H_{19}BrN_4O$ (M$^+$) 350.0742. found 350.0739.

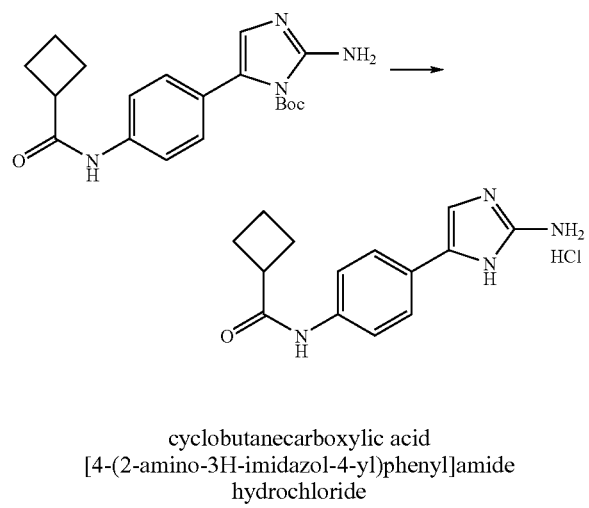

cyclobutanecarboxylic acid [4-(2-amino-3H-imidazol-4-yl)phenyl]amide hydrochloride In a similar manner, 0.060 g (0.168 mmol) of 2-amino-5-[4-(cyclobutanecarbonylamino)phenyl]imidazole-1-carboxylic acid tert-butyl ester afforded 0.048 g (98%) of cyclobutanecarboxylic acid [4-(2-amino-3H-imidazol-4-yl)phenyl]amide in its corresponding hydrochloride salt form as a yellow solid: $^1$H NMR (400 MHz, DMSO-$d_6$) δ 12.76 (s, 1H), 12.03 (s, 1H), 9.92 (s, 1H), 7.67 (d, 2H, J=9.2 Hz), 7.56 (d, 2H, J=8.4 Hz), 7.42 (br s, 2H), 7.28 (s, 1H), 3.22 (m, 1H), 2.19 (m, 2H), 2.11 (m, 2H), 1.92 (m, 1H), 1.81 (m, 1H); $^{13}$C NMR (100 MHz, CD$_3$OD) δ 176.4, 149.3, 140.6, 128.9, 126.2, 124.4, 121.6, 109.4, 41.8, 26.2, 19.1; HRMS (ESI) calcd for $C_{14}H_{16}N_4O$ (M$^+$) 256.1324. found 256.1321.

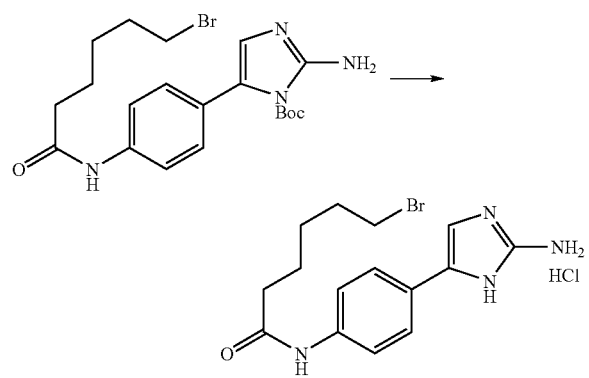

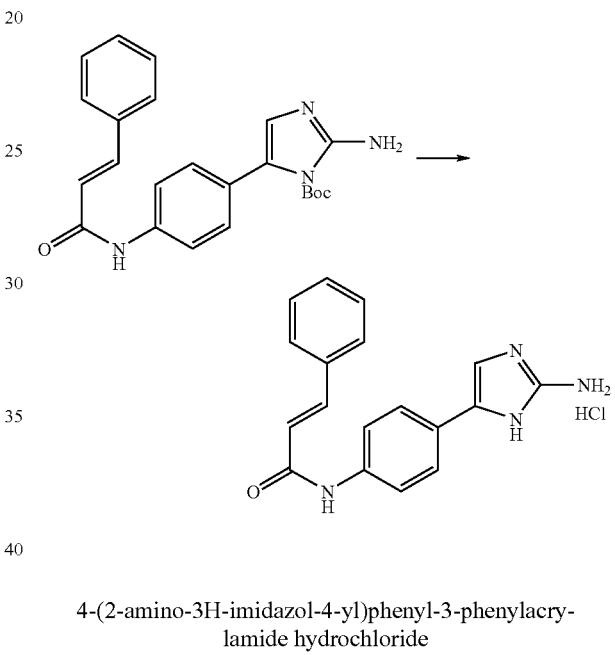

4-(2-amino-3H-imidazol-4-yl)phenyl-3-phenylacrylamide hydrochloride

In a similar manner, 0.061 g (0.151 mmol) of 2-amino-5-[4-(3-phenylacryloylamino)phenyl]imidazole-1-carboxylic acid tert-butyl ester afforded 0.050 g (98%) of 4-(2-amino-3H-imidazol-4-yl)phenyl-3-phenylacrylamide in its corresponding hydrochloride salt form as a yellow solid: $^1$H NMR (300 MHz, DMSO-$d_6$) δ 12.80 (s, 1H), 12.06 (s, 1H), 10.49 (s, 1H), 7.77 (d, 2H, J=8.7 Hz), 7.62 (m, 5H), 7.43 (m, 5H), 7.32 (s, 1H), 6.87 (d, 1H, J=15.9 Hz); $^{13}$C NMR (100 MHz, CD$_3$OD) δ 166.8, 149.3, 143.2, 140.5, 136.3, 131.3, 130.2, 129.1, 128.9, 126.3, 124.7, 122.2, 121.6, 109.5; HRMS (ESI) calcd for $C_{18}H_{16}N_4O$ (M$^+$) 304.1324. found 304.1319.

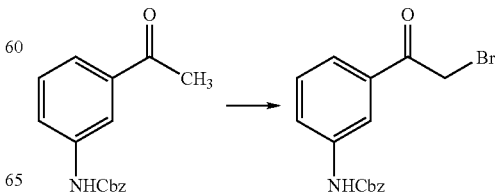

3-(2-bromoacetyl)phenyl carbamic acid benzyl ester 3-acetylphenyl carbamic acid benzyl ester (3.50 g, 13.0 mmol) was dissolved in diethyl ether (70 mL) and THF (20 mL) and brought to 0° C. A catalytic amount of aluminum (III) chloride (0.010 g) was added followed by the drop-wise addition of bromine (0.731 mL, 14.3 mmol) in diethyl ether (10 mL). The reaction was kept at 0° C. for 30 mins before being allowed to warm to room temperature on its own accord. Sat. NaHCO$_3$ (30 mL) was added to quench the reaction and the solution was poured into ethyl acetate (30 mL). The combined organics were washed with sat. NaHCO$_3$ (3×30 mL) and brine (1×30 mL) before being dried (Na$_2$SO$_4$), filtered, and evaporated to dryness. Trituration of the resulting crude product with a 2:1 mixture of dichloromethane/diethyl ether (6 mL) followed by filtration afforded 2.57 g (57%) of 3-(2-bromoacetyl)phenyl carbamic acid benzyl ester as a light pink solid: $^1$H NMR (400 MHz, DMSO-d$_6$) δ 10.04 (s, 1H), 8.11 (s, 1H), 7.69 (m, 2H), 7.43 (m, 6H), 5.18 (s, 2H), 4.88 (s, 2H); $^{13}$C NMR (100 MHz, DMSO-d$_6$) δ 201.5, 163.4, 149.8, 146.5, 144.6, 139.4, 138.5, 138.2, 133.3, 131.9, 127.6, 126.7, 76.0, 44.1; HRMS (ESI) calcd for C$_{16}$H$_{14}$BrNO$_3$ (M$^+$) 347.0157. found 347.0151.

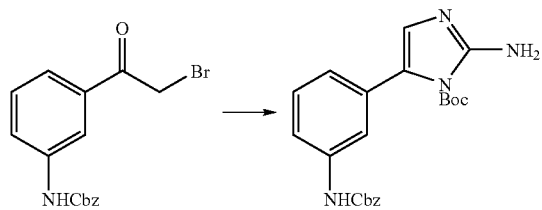 [SMILES: O=C(Nc1cccc(C(=O)CBr)c1)OCc1ccccc1 ; CC(C)(C)OC(=O)n1c(-c2cccc(NC(=O)OCc3ccccc3)c2)cnc1N]

2-amino-5-(3-benzyloxycarbonyl aminophenyl)imidazole-1-carboxylic acid tert-butyl ester 3-(2-bromoacetyl)phenyl carbamic acid benzyl ester (2.94 g, 8.43 mmol) and Boc-guanidine (4.02 g, 25.3 mmol) were dissolved in DMF (25 mL) and allowed to stir at room temperature. After 24 h the DMF was removed under reduced pressure and the residue taken up in ethyl acetate (50 mL) and washed with water (3×25 mL) and brine (25 mL) before being dried (Na$_2$SO$_4$), filtered, and evaporated to dryness. The resulting crude oil was purified by flash column chromatography (10-40% EtOAc/Hexanes) to obtain the pure product as an oil. This oil was triturated with cold hexanes (15 mL) and filtered to afford 1.40 g (48%) of 2-amino-5-(3-benzyloxycarbonyl aminophenyl)imidazole-1-carboxylic acid tert-butyl ester as a white solid: $^1$H NMR (300 MHz, DMSO-d$_6$) δ 9.75 (s, 1H), 7.89 (s, 1H), 7.22-7.42 (m, 9H), 6.62 (s, 2H), 5.15 (s, 2H), 1.58 (s, 9H); $^{13}$C NMR (100 MHz, DMSO-d$_6$) δ 153.4, 150.4, 148.9, 139.2, 137.0, 136.7, 134.0, 128.7, 128.4, 128.0, 119.0, 117.0, 114.7, 106.0, 84.7, 65.7, 27.6; HRMS (ESI) calcd for C$_{22}$H$_{24}$N$_4$O$_4$ (M$^+$) 408.1798. found 408.1796.

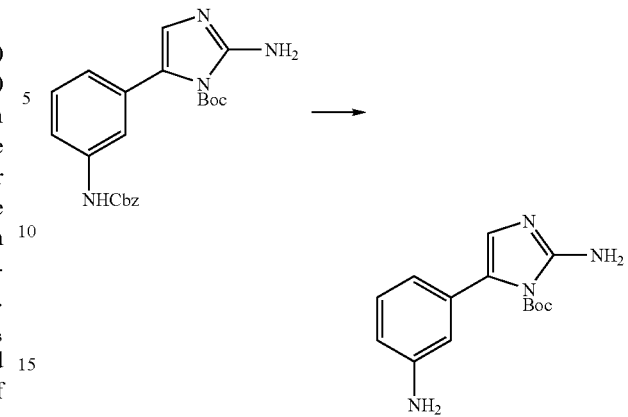

2-amino-5-(3-aminophenyl)imidazole-1-carboxylic acid tert-butyl ester

To a solution of absolute ethanol (50 mL) and 10% Pd/C (0.150 g) was charged 2-amino-5-(3-benzyloxycarbonyl aminophenyl)imidazole-1-carboxylic acid tert-butyl ester (1.40 g, 3.42 mmol). Air was removed from the system and the reaction was back flushed with hydrogen. This process was repeated three times before setting the reaction under 35 psi of hydrogen using a Parr-Shaker apparatus at room temperature for 16 h. After that time, the reaction was filtered to remove the catalyst and the filtrate evaporated to deliver 0.928 g (99%) of 2-amino-5-(3-aminophenyl)imidazole-1-carboxylic acid tert-butyl ester as a white solid. $^1$H NMR (300 MHz, DMSO-d$_6$) δ 7.11 (s, 1H), 6.95 (m, 2H), 6.85 (dd, 1H, J=0.9, 7.5 Hz), 6.53 (br s, 2H), 6.42 (m, 1H), 5.01 (br s, 2H), 1.57 (s, 9H); $^{13}$C NMR (100 MHz, DMSO-d$_6$) δ 150.2, 150.0, 148.6, 137.8, 133.8, 128.8, 112.9, 112.7, 110.4, 105.3, 84.5, 27.6; HRMS (ESI) calcd for C$_{14}$H$_{18}$N$_4$O$_2$ (M$^+$) 274.1430. found 274.1425.

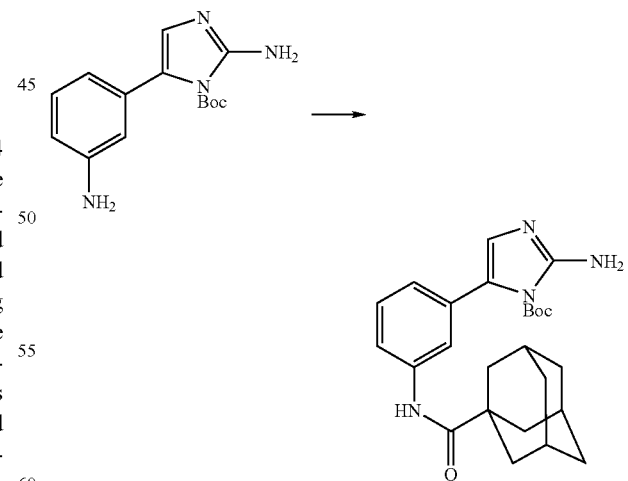

5-[3-(adamantane-1-carbonylamino)phenyl]-2-aminoimidazole-1-carboxylic acid tert-butyl ester In a similar manner, 0.075 g (0.273 mmol) of 2-amino-5-(3-aminophenyl)imidazole-1-carboxylic acid tert-butyl ester afforded 0.102 g (86%) of 5-[3-(adamantane-1-carbonylamino)phenyl]-2-aminoimidazole-1-carboxylic acid tert-butyl ester as a white solid: $^1$H NMR (400 MHz, DMSO-d$_6$) δ 9.15 (s, 1H), 8.00 (s, 1H), 7.56 (d, 1H, J=7.6 Hz), 7.38 (d, 1H, J=7.6 Hz), 7.22 (m, 2H), 6.63 (br s, 2H), 2.01 (br s, 4H), 1.92 (br s, 6H), 1.70 (br s, 6H), 1.58 (s, 9H); $^{13}$C NMR (100 MHz, DMSO-d$_6$) δ 175.9, 150.4, 148.9, 139.5, 137.1, 133.5, 128.4, 119.6, 118.9, 116.7, 105.8, 84.7, 40.9, 38.3, 36.0, 27.7, 27.5; HRMS (ESI) calcd for C$_{25}$H$_{32}$N$_4$O$_3$ (M$^+$) 436.2474. found 436.2468.

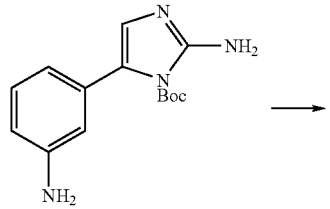

2-amino-5-{3-[(benzo[1,3]dioxole-5-carbonyl)-amino]phenyl}imidazole-1-carboxylic acid tert-butyl ester In a similar manner, 0.075 g (0.273 mmol) of 2-amino-5-(3-aminophenyl)imidazole-1-carboxylic acid ter-t-butyl ester afforded 0.091, (79%) of 2-amino-5-{3-[(benzo[1,3]dioxole-5-carbonyl)-amino]phenyl}imidazole-1-carboxylic acid tert-butyl ester as a white solid: $^1$H NMR (300 MHz, DMSO-d$_6$) δ 10.07 (s, 1H), 8.12 (m, 1H), 7.54-7.65 (m, 3H), 7.44 (m, 1H), 7.29 (t, 1H, J=7.8 Hz), 7.26 (s, 1H), 7.04 (d, 1H, J=8.4 Hz), 6.63 (br s, 2H), 6.14 (s, 2H), 1.59 (s, 9H); $^{13}$C NMR (100 MHz, DMSO-d$_6$) δ 164.3, 150.4, 150.0, 148.9, 147.4, 139.4, 139.3, 137.0, 133.7, 128.7, 128.6, 122.9, 120.0, 118.9, 116.8, 107.9, 107.7, 106.0, 101.8, 84.7, 27.5; HRMS (ESI) calcd for C$_{22}$H$_{22}$N$_4$O$_5$ (M$^+$) 422.1590. found 422.1585.

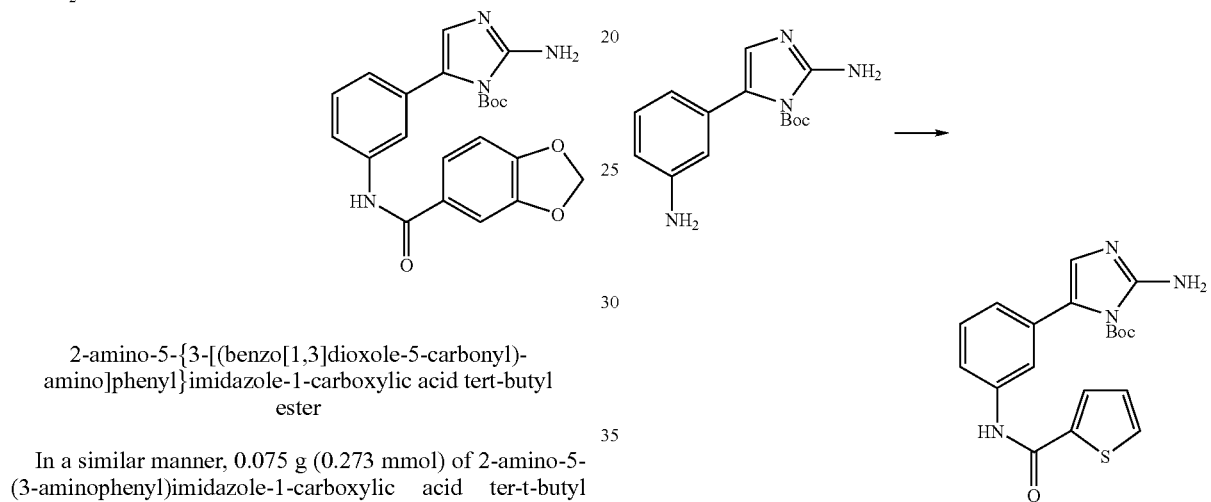

2-amino-5-[3-(4-pentylbenzoylamino)phenyl]imidazole-1-carboxylic acid tert-butyl ester In a similar manner, 0.075 g (0.273 mmol) of 2-amino-5-(3-aminophenyl)imidazole-1-carboxylic acid tert-butyl ester afforded 0.094 g (77%) of 2-amino-5-[3-(4-pentylbenzoylamino)phenyl]imidazole-1-carboxylic acid tert-butyl ester as a white solid: $^1$H NMR (300 MHz, DMSO-d$_6$) δ 10.18 (s, 1H), 8.12 (m, 1H), 7.90 (d, 2H, J=8.4 Hz), 7.64 (d, 1H, J=7.8 Hz), 7.45 (d, 1H, J=7.8 Hz), 7.31 (m, 4H), 6.64 (br s, 2H), 2.65 (t, 2H, J=7.8 Hz), 1.66 (m, 2H), 1.59 (s, 9H), 1.29 (m, 4H), 0.87 (t, 3H, J=5.1 Hz); $^{13}$C NMR (100 MHz, CDCl$_3$) δ 165.9, 150.7, 149.6, 147.5, 138.6, 137.3, 134.2, 132.5, 129.5, 127.3, 121.1, 119.1, 116.7, 106.8, 85.5, 36.0, 31.6, 31.1, 28.2, 22.7, 14.2; HRMS (ESI) calcd for C$_{26}$H$_{32}$N$_4$O$_3$ (M$^+$) 448.2474. found 448.2472.

2-amino-5-{3-[(thiophene-2-carbonyl)amino]phenyl}imidazole-1-carboxylic acid tert-butyl ester In a similar manner, 0.075 g (0.273 mmol) of 2-amino-5-(3-aminophenyl)imidazole-1-carboxylic acid tert-butyl ester afforded 0.061 g (59%) of 2-amino-5-{3-[(thiophene-2-carbonyl)amino]phenyl}imidazole-1-carboxylic acid tert-butyl ester as a white foam: $^1$H NMR (400 MHz, CDCl$_3$) δ 7.96 (s, 1H), 7.86 (t, 1H, J=1.6 Hz), 7.70 (m, 1H), 7.61 (dd, 1H, J=1.2, 4.0 Hz), 7.53 (dd, 1H, J=1.2, 4.8 Hz), 7.45 (m, 1H), 7.34 (t, 1H, J=7.6 Hz), 7.14 (s, 1H), 7.10 (m, 1H), 5.93 (br s, 2H), 1.63 (s, 9H); $^{13}$C NMR (100 MHz, CDCl$_3$) δ 160.1, 150.6, 149.6, 139.6, 138.2, 137.2, 134.3, 130.9, 129.5, 128.6, 128.0, 121.3, 119.2, 116.7, 106.9, 85.5, 28.2; HRMS (ESI) calcd for C$_{19}$H$_{20}$N$_4$O$_3$S (M$^+$) 384.1256. found 384.1250.

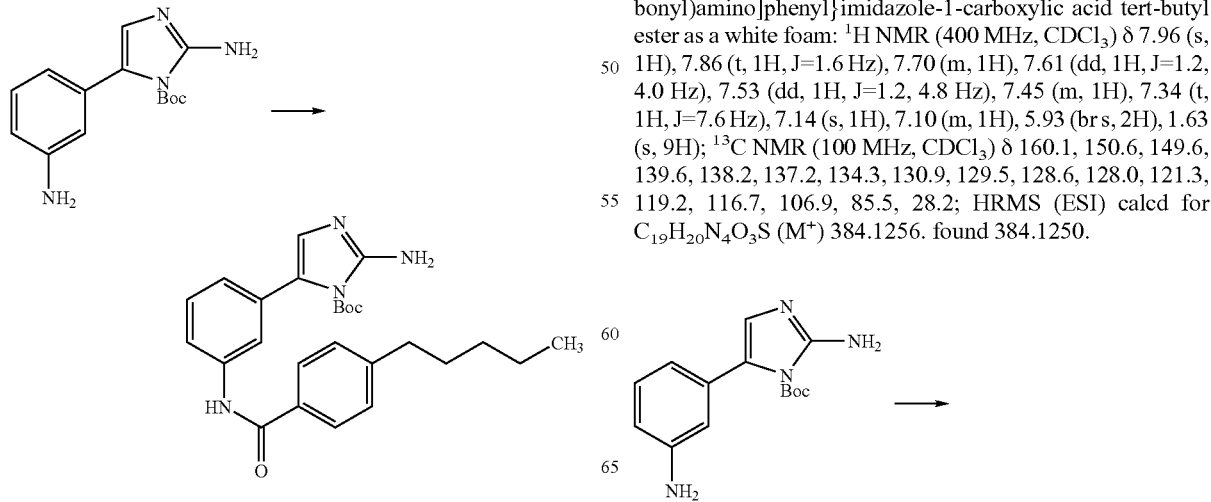

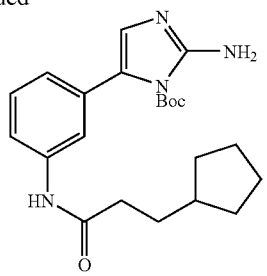

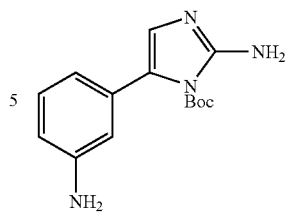

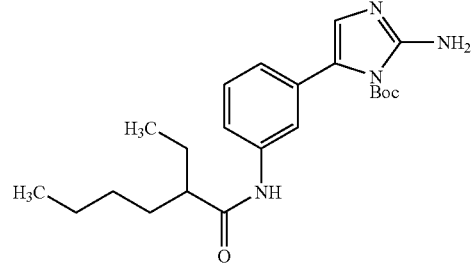

2-amino-5-[3-(3-cyclopentylpropionylamino)phenyl]imidazole-1-carboxylic acid tert-butyl ester In a similar manner, 0.075 g (0.273 mmol) of 2-amino-5-(3-aminophenyl)imidazole-1-carboxylic acid tert-butyl ester afforded 0.085 g (79%) of 2-amino-5-[3-(3-cyclopentylpropionylamino)phenyl]imidazole-1-carboxylic acid tert-butyl ester as a white foam: $^1$H NMR (300 MHz, DMSO-$d_6$) δ 9.91 (s, 1H), 7.96 (s, 1H), 7.45 (d, 1H, J=8.1 Hz), 7.37 (d, 1H, J=8.1 Hz), 7.27 (m, 2H), 6.98 (br s, 2H), 2.31 (t, 2H, J=7.5 Hz), 1.75 (m, 2H), 1.51 (m, 16H), 1.10 (m, 2H); $^{13}$C NMR (100 MHz, CDCl$_3$) δ 172.0, 150.5, 149.1, 138.8, 135.0, 132.1, 129.6, 120.8, 119.4, 116.2, 106.6, 86.6, 39.9, 37.2, 32.7, 32.0, 28.2, 25.3; HRMS (ESI) calcd for C$_{22}$H$_{30}$N$_4$O$_3$ (M$^+$) 398.2318. found 398.2311.

2-amino-5-[3-(2-ethylhexanoylamino)phenyl]imidazole-1-carboxylic acid tert-butyl ester In a similar manner, 0.075 g (0.273 mmol) of 2-amino-5-(3-aminophenyl)imidazole-1-carboxylic acid tert-butyl ester afforded 0.088 g (81%) of 2-amino-5-[3-(2-ethylhexanoylamino)phenyl]imidazole-1-carboxylic acid tert-butyl ester as a white solid: $^1$H NMR (300 MHz, DMSO-$d_6$) δ 9.87 (s, 1H), 8.00 (s, 1H), 7.47 (m, 1H), 7.38 (m, 1H), 7.24 (m, 2H), 6.70 (br s, 2H), 2.28 (tt, 1H, J=4.5, 9.0 Hz), 1.23-1.58 (m, 17H), 0.85 (m, 6H); $^{13}$C NMR (100 MHz, CDCl$_3$) δ 174.7, 150.5, 149.7, 138.5, 136.8, 133.7, 129.5, 120.9, 119.0, 116.2, 106.8, 85.8, 51.2, 32.9, 30.1, 28.2, 26.4, 23.0, 14.2, 12.3; HRMS (ESI) calcd for C$_{22}$H$_{32}$N$_4$O$_3$ (M$^+$) 400.2474. found 400.2472.

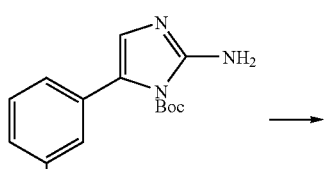

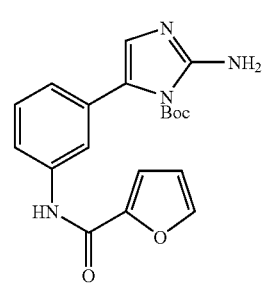

2-amino-5-{3-[furan-2-carbonyl)amino]phenyl}imidazole-1-carboxylic acid tert-butyl ester In a similar manner, 0.075 g (0.273 mmol) of 2-amino-5-(3-aminophenyl)imidazole-1-carboxylic acid tert-butyl ester afforded 0.058 g (58%) of 2-amino-5-{3-[(furan-2-carbonyl)amino]phenyl}imidazole-1-carboxylic acid tert-butyl ester as a white foam: $^1$H NMR (300 MHz, DMSO-$d_6$) δ 10.17 (s, 1H), 8.11 (m, 1H), 7.94 (m, 1H), 7.62 (m, 1H), 7.45 (m, 1H), 7.35 (dd, 1H, J=1.2, 3.6 Hz), 7.30 (t, 1H, J=8.1 Hz), 7.27 (s, 1H), 6.71 (m, 1H), 6.63 (br s, 2H), 1.51 (s, 9H); $^{13}$C NMR (100 MHz, CDCl$_3$) δ 156.3, 150.8, 149.6, 148.0, 144.4, 137.8, 137.3, 134.3, 129.5, 121.2, 118.2, 116.4, 115.3, 112.7, 106.8, 85.4, 28.2; HRMS (ESI) calcd for C$_{19}$H$_{20}$N$_4$O$_4$ (M$^+$) 368.1485. found 368.1479.

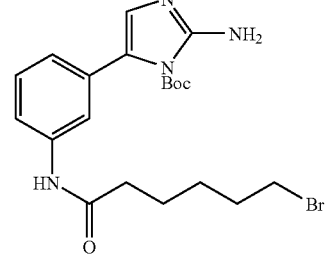

2-amino-5-[3-(6-bromohexanoylamino)phenyl]imidazole-1-carboxylic acid tert-butyl ester In a similar manner, 0.075 g (0.273 mmol) of 2-amino-5-(3-aminophenyl)imidazole-1-carboxylic acid tert-butyl ester afforded 0.090 g (73%) of 2-amino-5-[3-(6-bromohexanoylamino)phenyl]imidazole-1-carboxylic acid tert-butyl ester as a white solid: $^1$H NMR (300 MHz, DMSO-$d_6$) δ 9.89 (s, 1H), 7.96 (s, 1H), 7.35 (d, 1H, J=8.1 Hz), 7.26 (d, 1H, J=7.8 Hz), 7.22 (s, 1H), 6.61 (br s, 2H), 3.54 (t, 2H, J=5.4 Hz), 2.31 (m, 2H), 1.83 (m, 2H), 1.55 (s, 9H), 1.42 (m, 2H); $^{13}$C NMR (100 MHz, CD$_3$OD) δ 171.2, 150.6, 149.6, 138.4, 137.4, 134.2, 129.5, 121.1, 118.9, 116.3, 107.0, 85.6, 37.6, 33.8, 32.7, 28.2, 28.0, 24.8; HRMS (ESI) calcd for $C_{14}H_{17}N_4O$ (M$^+$) 256.1324. found 256.1319.

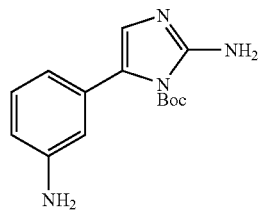

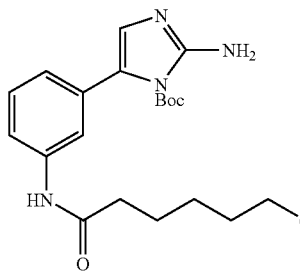

2-amino-5-(3-heptanoylaminophenyl)imidazole-1-carboxylic acid tert-butyl ester In a similar manner, 0.075 g (0.273 mmol) of 2-amino-5-(3-aminophenyl)imidazole-1-carboxylic acid tert-butyl ester afforded 0.075 g (69%) of 2-amino-5-(3-heptanoylaminophenyl)imidazole-1-carboxylic acid tert-butyl ester as a white solid: $^1$H NMR (300 MHz, DMSO-d$_6$) δ 9.87 (s, 1H), 7.96 (s, 1H), 7.37 (d, 1H, J=7.5 Hz), 7.35 (d, 1H, J=6.9 Hz), 7.23 (s, 1H), 6.61 (br s, 2H), 2.27 (t, 2H, J=7.5 Hz), 1.59 (s, 9H), 1.27 (m, 8H), 0.85 (m, 3H); $^{13}$C NMR (100 MHz, CD$_3$OD) δ 171.7, 150.7, 149.6, 138.5, 137.3, 134.1, 129.4, 121.0, 118.9, 116.3, 106.8, 85.6, 38.1, 31.8, 29.1, 28.2, 25.8, 22.7, 14.2; HRMS (ESI) calcd for $C_{21}H_{30}N_4O_3$ (M$^+$) 386.2318. found 386.2313.

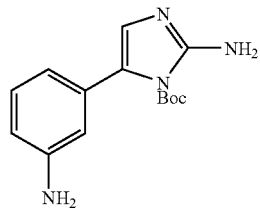

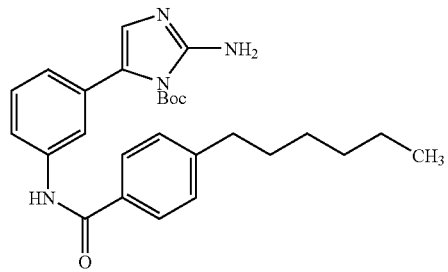

2-amino-5-[3-(4-hexylbenzoylamino)phenyl]imidazole-1-carboxylic acid tert-butyl ester In a similar manner, 0.075 g (0.273 mmol) of 2-amino-5-(3-aminophenyl)imidazole-1-carboxylic acid tert-butyl ester afforded 0.086 g (68%) of 2-amino-5-[3-(4-hexylbenzoylamino)phenyl]imidazole-1-carboxylic acid tert-butyl ester as a white foam: $^1$H NMR (300 MHz, DMSO-d$_6$) δ 10.17 (s, 1H), 8.15 (s, 1H), 7.89 (d, 2H, J=8.1), 7.65 (m, 1H), 7.45 (m, 1H), 7.34 (d, 2H, J=8.1 Hz), 7.30 (s, 1H), 7.26 (s, 1H), 6.64 (br s, 2H), 2.65 (m, 2H), 1.59 (s, 9H), 1.27 (m, 8H), 0.85 (m, 3H); $^{13}$C NMR (100 MHz, CD$_3$OD) δ 168.9, 152.8, 150.7, 148.6, 140.3, 138.1, 134.8, 133.7, 130.9, 130.1, 129.5, 122.3, 121.4, 118.8, 107.9, 86.9, 37.0, 33.0, 32.5, 30.2, 28.3, 23.8, 14.6; HRMS (ESI) calcd for $C_{27}H_{34}N_4O_3$ (M$^+$) 462.2631. found 462.2624.

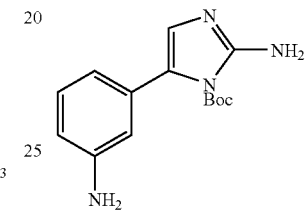

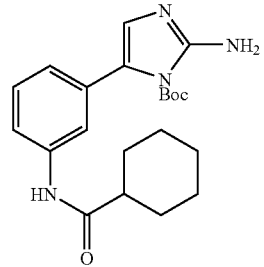

2-amino-5-[3-(cyclohexanecarbonylamino)phenyl]imidazole-1-carboxylic acid tert-butyl ester In a similar manner, 0.075 g (0.273 mmol) of 2-amino-5-(3-aminophenyl)imidazole-1-carboxylic acid tert-butyl ester afforded 0.088 g (82%) of 2-amino-5-[3-(cyclohexanecarbonylamino)phenyl]imidazole-1-carboxylic acid tert-butyl ester as a white foam: $^1$H NMR (300 MHz, DMSO-d$_6$) δ 9.72 (s, 1H), 7.97 (s, 1H), 7.50 (d, 1H, J=8.1 Hz), 7.40 (d, 1H, J=5.6 Hz), 7.26 (m, 1H), 6.61 (br s, 2H), 3.30 (m, 1H), 2.19 (m, 4H), 2.07 (m, 4H), 1.90 (m, 2H), 1.55 (s, 9H); $^{13}$C NMR (100 MHz, CD$_3$OD) δ 174.6, 150.9, 149.5, 138.6, 137.1, 133.9, 129.4, 120.9, 118.9, 116.3, 106.7, 85.6, 43.8, 29.9, 28.2, 26.1, 25.9; HRMS (ESI) calcd for $C_{21}H_{25}N_4O_3$ (M$^+$) 384.2161. found 384.2158.

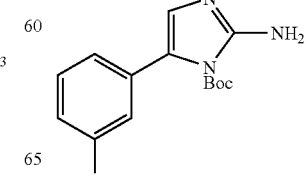

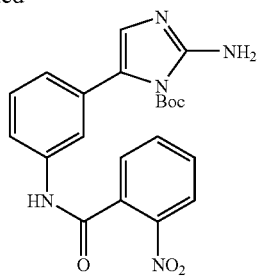

2-amino-5-[3-(2-nitrobenzoylamino)phenyl]imidazole-1-carboxylic acid tert-butyl ester In a similar manner, 0.075 g (0.273 mmol) of 2-amino-5-(3-aminophenyl)imidazole-1-carboxylic acid tert-butyl ester afforded 0.095 g (83%) of 2-amino-5-[3-(2-nitrobenzoylamino)phenyl]imidazole-1-carboxylic acid tert-butyl ester as a white foam: $^1$H NMR (300 MHz, DMSO-$d_6$) δ 10.67 (s, 1H), 8.12 (m, 1H), 8.11 (s, 1H), 7.85 (m, 1H), 7.80 (m, 2H), 7.48 (m, 2H), 7.35 (m, 1H), 7.28 (s, 1H), 6.64 (br s, 2H), 1.55 (s, 9H); $^{13}$C NMR (100 MHz, CD$_3$OD) δ 167.5, 152.9, 150.7, 147.8, 140.1, 138.2, 135.3, 135.2, 134.4, 132.1, 130.3, 125.7, 122.7, 120.7, 118.2, 108.0, 86.9; HRMS (ESI) calcd for CH$_{21}$H$_{21}$N$_5$O$_5$ (M$^+$) 423.1543. found 423.1564.

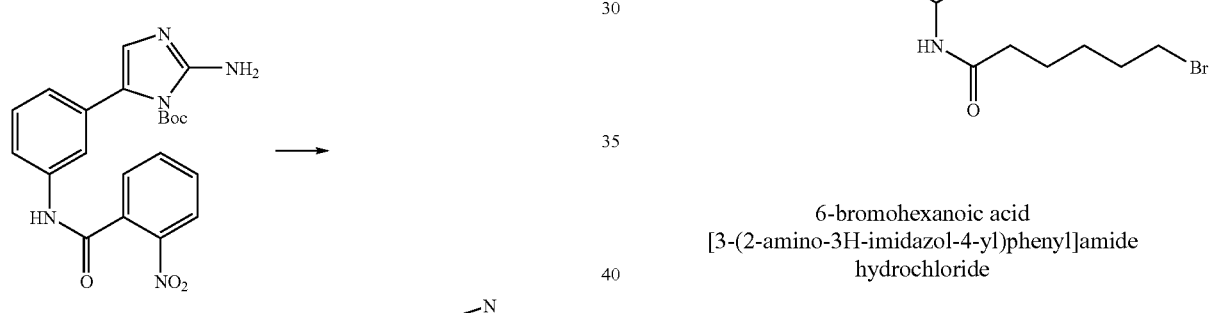

3-(2-amino-3H-imidazol-4-yl)phenyl]-2-nitrobenzamide hydrochloride 2-amino-5-[3-(2-nitrobenzoylamino)phenyl]imidazole-1-carboxylic acid tert-butyl ester (0.070 g, 0.165 mmol) was dissolved in anhydrous dichloromethane (5 mL) and cooled to 0° C. Trifluoroacetic acid (0.50 mL) was added drop-wise while the reaction continued to stir at 0° C. Upon completion, the reaction was allowed to warm to room temperature over the course of 12 h. Toluene (2 mL) was added and the reaction was evaporated to dryness. The crude TFA salt was then dissolved in dichloromethane (3 mL) and a 2M solution of HCl in diethyl ether (0.10 mL) was added. The solution was again concentrated under reduced pressure and the resulting product triturated with cold diethyl ether (5 mL) to afford 0.058 g (98%) of the desired compound 3-(2-amino-3H-imidazol-4-yl)phenyl]-2-nitrobenzamide in its corresponding hydrochloride salt form as a yellow foam: $^1$H NMR (300 MHz, DMSO-$d_6$) δ 12.82 (s, 1H), 12.17 (s, 1H), 10.85 (s, 1H), 8.17 (m, 1H), 8.00 (s, 1H), 7.83 (m, 1H), 7.79 (m, 2H), 7.42-7.52 (m, 5H), 7.32 (s, 1H); $^{13}$C NMR (100 MHz, CD$_3$OD) δ 165.8, 148.0, 147.0, 139.3, 134.1, 132.8, 131.0, 129.8, 129.0, 128.5, 127.0, 124.5, 120.8, 120.4, 116.3, 109.0; HRMS (ESI) calcd for C$_{16}$H$_{13}$N$_5$O$_3$ (M$^+$) 323.1018. found 323.1022.

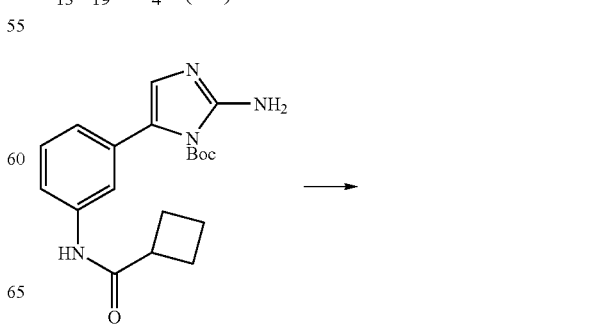

6-bromohexanoic acid [3-(2-amino-3H-imidazol-4-yl)phenyl]amide hydrochloride In a similar manner, 0.050 g (0.110 mmol) of 2-amino-5-[3-(6-bromohexanoylamino)phenyl]imidazole-1-carboxylic acid tert-butyl ester afforded 0.041 g (98%) of 6-bromohexanoic acid [3-(2-amino-3H-imidazol-4-yl)phenyl]amide in its corresponding hydrochloride salt form as a yellow solid: $^1$H NMR (300 MHz, DMSO-$d_6$) δ 12.79 (s, 1H), 12.10 (s, 1H), 10.12 (s, 1H), 7.94 (s, 1H), 7.44 (s, 2H), 7.29 (m, 4H), 3.54 (t, 2H, J=6.3 Hz), 2.34 (m, 2H), 1.83 (m, 2H), 1.62 (m, 2H), 1.45 (m, 2H); $^{13}$C NMR (100 MHz, CD$_3$OD) δ 173.0, 148.0, 140.0, 131.0, 129.6, 128.5, 128.0, 120.1, 116.1, 109.0, 36.6, 33.01, 32.5, 27.6, 24.8; HRMS (ESI) calcd for C$_{15}$H$_{19}$BrN$_4$O (M$^+$) 350.0742. found 350.0738.

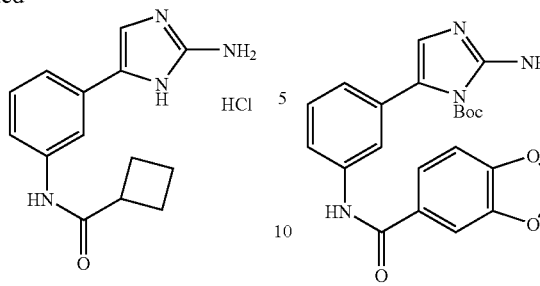

cyclobutanecarboxylic acid [3-(2-amino-3H-imidazol-4-yl)phenyl]amide hydrochloride In a similar manner, 0.050 g (0.140 mmol) of 2-amino-5-[3-(cyclobutanecarbonylamino)phenyl]imidazole-1-carboxylic acid tert-butyl ester afforded 0.059 g (85%) of cyclobutanecarboxylic acid [3-(2-amino-3H-imidazol-4-yl)phenyl]amide in its corresponding hydrochloride salt form as a white solid: $^1$H NMR (300 MHz, DMSO-$d_6$) δ 12.71 (s, 1H), 12.10 (s, 1H), 9.90 (s, 1H), 7.97 (s, 1H), 7.43 (s, 2H), 7.34 (m, 4H), 3.26 (t, 1H, J=8.1 Hz), 2.17 (m, 4H), 1.94 (m, 2H); $^{13}$C NMR (100 MHz, CD$_3$OD) δ 176.4, 161.5, 150.0, 141.0, 130.8, 129.6, 121.4, 121.3, 117.4, 110.3, 41.7, 26.2, 19.2; HRMS (ESI) calcd for $C_{14}H_{17}N_4O$ (M$^+$) 256.1324. found 256.1323.

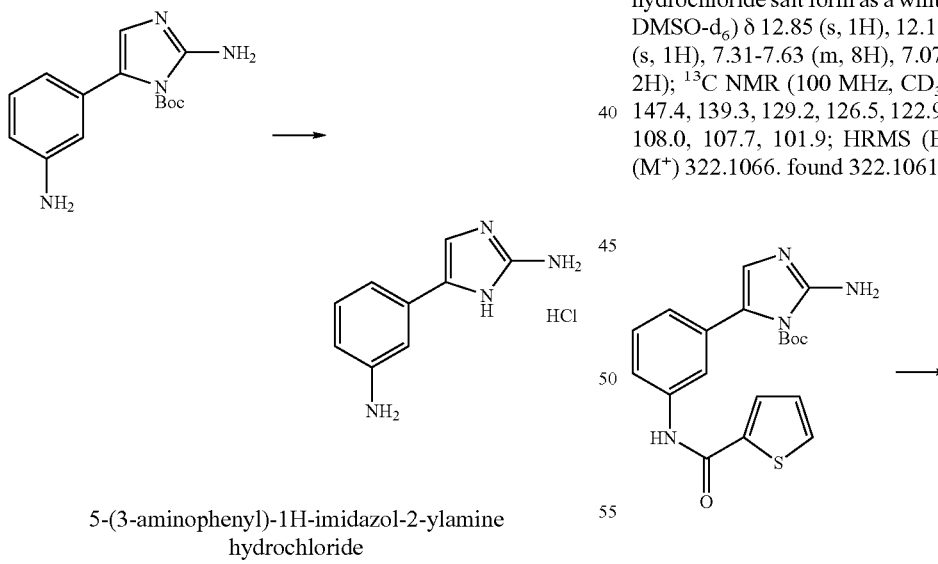

5-(3-aminophenyl)-1H-imidazol-2-ylamine hydrochloride

In a similar manner, 0.045 g (0.165 mmol) of 2-amino-5-(3-aminophenyl)imidazole-1-carboxylic acid tert-butyl ester afforded 0.033 g (97%) of 5-(3-aminophenyl)-1H-imidazol-2-ylamine in its corresponding hydrochloride salt form as a yellow amorphous solid: $^1$H NMR (300 MHz, DMSO-$d_6$) δ 13.02 (s, 1H), 12.23 (s, 1H), 7.40-7.51 (m, 8H), 7.17 (d, 1H, J=7.2 Hz); $^{13}$C NMR (100 MHz, CD$_3$OD) δ 149.5, 133.2, 132.3, 131.3, 127.5, 126.2, 124.0, 120.4, 111.9; HRMS (ESI) calcd for $C_9H_{10}N_4$ (M$^+$) 174.0906. found 174.0902.

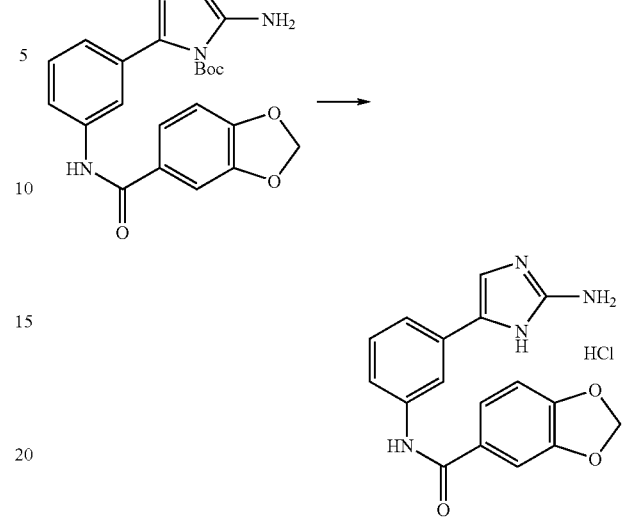

benzo[1,3]dioxole-5-carboxylic acid [3-(2-amino-3H-imidazol-4-yl)phenyl]amide hydrochloride In a similar manner, 0.049 g (0.116 mmol) of 2-amino-5-{3[(benzo[1,3]dioxole-5-carbonyl)-amino]phenyl}imidazole-1-carboxylic acid tert-butyl ester afforded 0.040 g (97%) of benzo[1,3]dioxole-5-carboxylic acid [3-(2-amino-3H-imidazol-4-yl)phenyl]amide in its corresponding hydrochloride salt form as a white solid: $^1$H NMR (300 MHz, DMSO-$d_6$) δ 12.85 (s, 1H), 12.18 (s, 1H), 10.23 (s, 1H), 8.09 (s, 1H), 7.31-7.63 (m, 8H), 7.07 (d, 1H, J=8.1 Hz), 6.14 (s, 2H); $^{13}$C NMR (100 MHz, CD$_3$OD) δ 164.6, 150.2, 147.9, 147.4, 139.3, 129.2, 126.5, 122.9, 120.5, 119.8, 116.6, 109.5, 108.0, 107.7, 101.9; HRMS (ESI) calcd for $C_{17}H_{14}N_4O_3$ (M$^+$) 322.1066. found 322.1061.

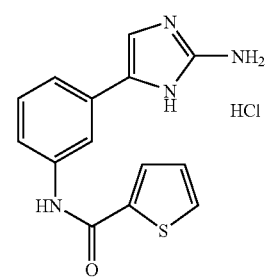

thiophene-2-carboxylic acid [3-(2-amino-3H-imidazol-4-yl)phenyl]amide hydrochloride In a similar manner, 0.025 g (0.065 mmol) of 2-amino-5-{3-[(thiophene-2-carbonyl)amino]phenyl}imidazole-1-carboxylic acid tert-butyl ester afforded 0.020 g (95%) of thiophene-2-carboxylic acid [3-(2-amino-3H-imidazol-4-yl)phenyl]amide in its corresponding hydrochloride salt form as a white solid: $^1$H NMR (300 MHz, DMSO-d$_6$) δ 12.82 (s, 1H), 12.16 (s, 1H), 10.44 (s, 1H), 8.17 (m, 1H), 8.06 (s, 1H), 7.88 (m, 1H), 7.57 (m, 1H), 7.42 (m, 4H), 7.33 (s, 1H), 7.24 (m, 1H); $^{13}$C NMR (100 MHz, CD$_3$OD) δ 163.0, 149.2, 140.7, 140.6, 133.0, 130.9, 130.5, 129.7, 129.2, 129.0, 122.3, 121.8, 118.5, 110.4; HRMS (ESI) calcd for C$_{14}$H$_{12}$N$_4$OS (M$^+$) 284.0732. found 284.0729.

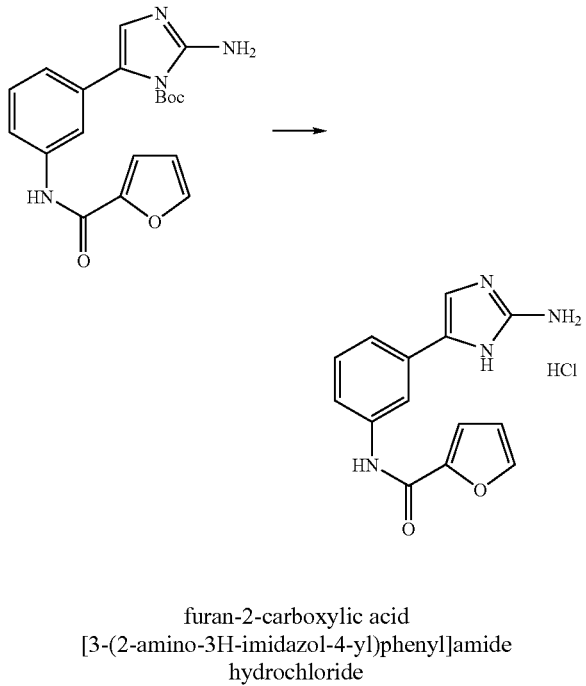

furan-2-carboxylic acid [3-(2-amino-3H-imidazol-4-yl)phenyl]amide hydrochloride In a similar manner, 0.031 g (0.084 mmol) of 2-amino-5-{3-[(furan-2-carbonyl)amino]phenyl}imidazole-1-carboxylic acid tert-butyl ester afforded 0.025 g (99%) of furan-2-carboxylic acid [3-(2-amino-3H-imidazol-4-yl)phenyl]amide in its corresponding hydrochloride salt form as a colorless film: $^1$H NMR (300 MHz, DMSO-d$_6$) δ 12.88 (s, 1H), 12.21 (s, 1H), 10.33 (s, 1H), 8.00 (m, 1H), 7.60 (m, 1H), 7.52 (br s, 2H), 7.39 (m, 4H), 7.30 (s, 1H), 6.72 (m, 1H); $^{13}$C NMR (100 MHz, CD$_3$OD) δ 159.1, 149.5, 148.9, 147.0, 140.1, 130.9, 129.6, 128.9, 122.3, 121.8, 118.3, 116.5, 113.4, 110.3; HRMS (ESI) calcd for C$_{14}$H$_{12}$N$_4$O$_2$ (M$^+$) 268.0960. found 268.0956.

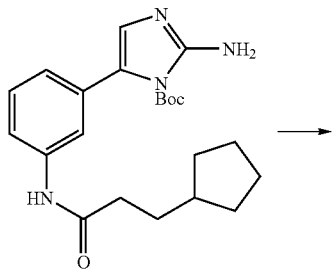

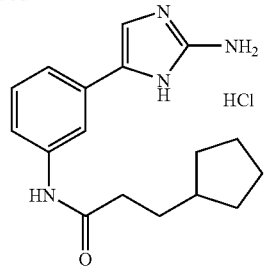

3-(2-amino-3H-imidazol-4-yl)phenyl-3-cyclopentyl-propionamide hydrochloride

In a similar manner, 0.040 g (0.100 mmol) of 2-amino-5-[3-(3-cyclopentylpropionylamino)phenyl]imidazole-1-carboxylic acid tert-butyl ester afforded 0.033 g (99%) of 3-(2-amino-3H-imidazol-4-yl)phenyl-3-cyclopentylpropionamide in its corresponding hydrochloride salt form as a tan amorphous solid: $^1$H NMR (300 MHz, DMSO-d$_6$) δ 12.87 (s, 1H), 12.21 (s, 1H), 10.13 (s, 1H), 7.93 (s, 1H), 7.45 (m, 3H), 7.25-7.38 (m, 3H), 2.34 (t, 2H, J=7.2 Hz), 1.73 (m, 3H), 1.46-1.64 (m, 6H), 1.10 (m, 2H); $^{13}$C NMR (100 MHz, CD$_3$OD) δ 175.2, 149.4, 140.9, 130.8, 129.6, 129.0, 121.3, 117.3, 110.3, 41.2, 37.5, 33.7, 33.3, 26.2; HRMS (ESI) calcd for C$_{17}$H$_{22}$N$_4$O (M$^+$) 298.1794. found 298.1789.

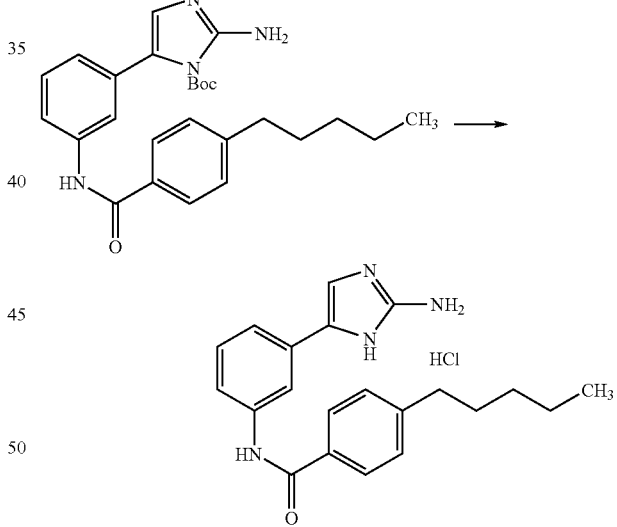

3-(2-amino-3H-imidazol-4-yl)phenyl-4-pentylbenzamide hydrochloride

In a similar manner, 0.050 g (0.111 mmol) of 2-amino-5-[3-(4-pentylbenzoylamino)phenyl]imidazole-1-carboxylic acid tert-butyl ester afforded 0.042 g (98%) of 3-(2-amino-3H-imidazol-4-yl)phenyl-4-pentylbenzamide in its corresponding hydrochloride salt form as a tan amorphous solid: $^1$H NMR (400 MHz, DMSO-d$_6$) δ 12.74 (s, 1H), 12.10 (s, 1H), 10.30 (s, 1H), 8.09 (s, 1H), 7.88 (d, 2H, J=8.0 Hz), 7.57 (m, 1H), 7.30-7.45 (m, 7H), 2.64 (t, 2H, J=7.2 Hz), 1.60 (m, 2H), 1.29 (m, 4H), 0.87 (t, 3H, J=6.6 Hz); $^{13}$C NMR (100

MHz, CD$_3$OD) δ 169.5, 149.3, 149.0, 141.3, 133.8, 132.4, 131.2, 130.2, 130.0, 129.3, 122.8, 122.1, 118.9, 110.7, 37.2, 33.1, 32.6, 24.1, 14.8; HRMS (ESI) calcd for C$_{21}$H$_{24}$N$_4$O (M$^+$) 348.1950. found 348.1944.

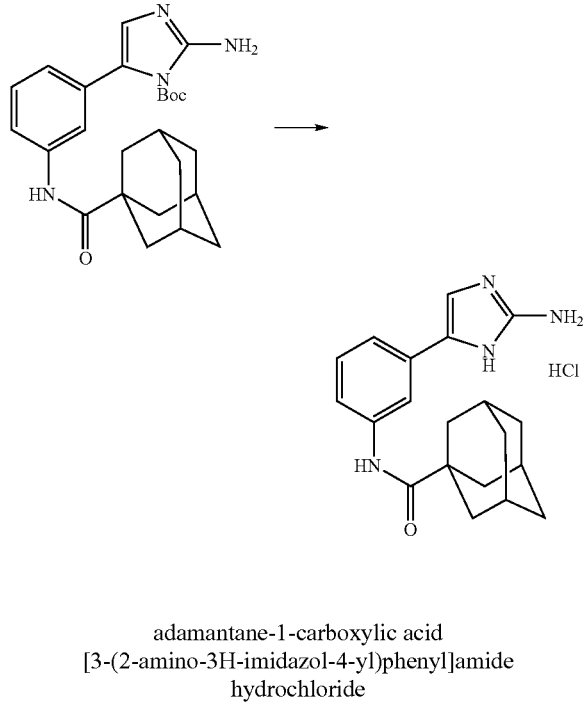

adamantane-1-carboxylic acid [3-(2-amino-3H-imidazol-4-yl)phenyl]amide hydrochloride In a similar manner, 0.060 g (0.137 mmol) of 5-{3-[(adamantane-1-carbonyl)amino]phenyl}-2-aminoimidazole-1-carboxylic acid tert-butyl ester afforded 0.050 g (98%) of adamantane-1-carboxylic acid [3-(2-amino-3H-imidazol-4-yl)phenyl]amide in its corresponding hydrochloride salt form as a white solid: $^1$H NMR (300 MHz, DMSO-d$_6$) δ 12.80 (s, 1H), 12.17 (s, 1H), 9.29 (s, 1H), 7.98 (s, 1H), 7.49 (m, 3H), 7.32 (m, 3H), 2.02 (br s, 3H), 1.92 (br s, 6H), 1.71 (br s, 6H); $^{13}$C NMR (100 MHz, CD$_3$OD) δ 179.7, 149.5, 140.7, 130.7, 129.5, 129.1, 122.8, 121.6, 119.0, 110.3, 42.8, 40.1, 37.7, 29.8; HRMS (ESI) calcd for C$_{20}$H$_{25}$N$_4$O (M$^+$) 336.1950. found 336.1945.

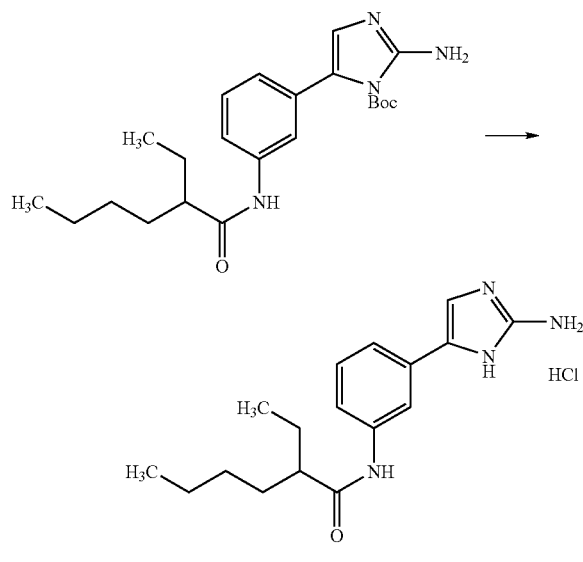

2-ethylhexanoic acid 3-(2-amino-3H-imidazol-4-yl)phenylamide hydrochloride

In a similar manner, 0.052 g (0.130 mmol) of 2-amino-5-[3-(2-ethylhexanoylamino)phenyl]imidazole-1-carboxylic acid tert-butyl ester afforded 0.042 g (99%) of 2-ethylhexanoic acid 3-(2-amino-3H-imidazol-4-yl)phenylamide in its corresponding hydrochloride salt form as a white solid: $^1$H NMR (300 MHz, DMSO-d$_6$) δ 12.79 (s, 1H), 12.18 (s, 1H), 10.06 (s, 1H), 7.99 (s, 1H), 7.43 (m, 3H), 7.28 (m, 3H), 2.30 (m, 1H), 1.27-1.58 (m, 8H), 0.85 (m, 6H); $^{13}$C NMR (100 MHz, CD$_3$OD) δ 177.9, 149.5, 140.7, 130.9, 129.7, 129.0, 121.5, 117.6, 110.3, 95.9, 50.8, 33.9, 31.1, 27.5, 23.9, 14.5, 12.5; HRMS (ESI) calcd for C$_{17}$H$_{24}$N$_4$O (M$^+$) 300.1950. found 300.1946.

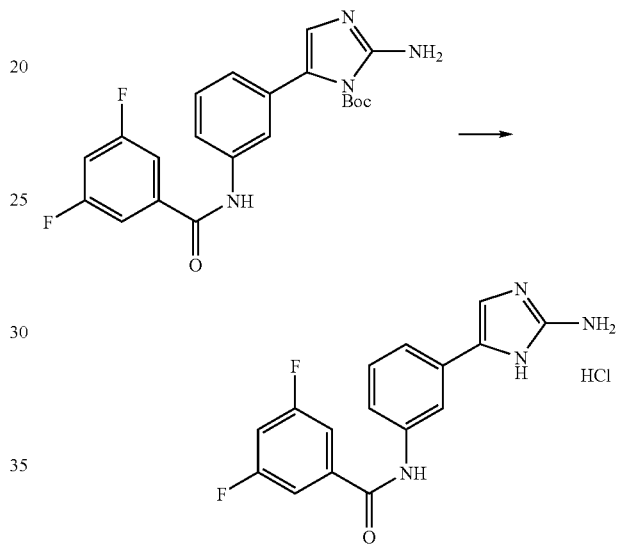

3-(2-amino-3H-imidazol-4-yl)phenyl]-3,5-difluorobenzamide hydrochloride

In a similar manner, 0.041 g (0.098 mmol) of 2-amino-5-[3-(3,5-difluorobenzoylamino)phenyl]imidazole-1-carboxylic acid tert-butyl ester afforded 0.034 g (98%) of 3-(2-amino-3H-imidazol-4-yl)phenyl]-3,5-difluorobenzamide in its corresponding hydrochloride salt form as a white solid: $^1$H NMR (300 MHz, DMSO-d$_6$) δ 12.79 (s, 1H), 12.13 (s, 1H), 10.57 (s, 1H), 8.09 (s, 1H), 7.72 (d, 2H, J=6.0 Hz), 7.53 (m, 2H), 7.44 (m, 4H), 7.32 (s, 1H); $^{13}$C NMR (100 MHz, CD$_3$OD) δ 166.5, 149.5, 148.1, 140.5, 130.9, 129.7, 128.9, 122.4, 122.1, 118.5, 112.2, 112.0, 110.5, 108.2; HRMS (ESI) calcd for C$_{16}$H$_{12}$F$_2$N$_4$O (M$^+$) 314.0979. found 314.0974.

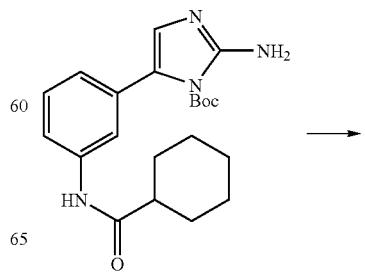

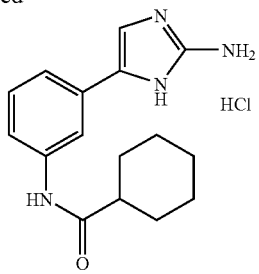

cyclohexanecarboxylic acid
[3-(2-amino-3H-imidazol-4-yl)phenyl]amide
hydrochloride In a similar manner, 0.050 g (0.130 mmol) of 2-amino-5-[3-(cyclohexanecarbonylamino)phenyl]imidazole-1-carboxylic acid tert-butyl ester afforded 0.038 g (92%) of cyclohexanecarboxylic acid [3-(2-amino-3H-imidazol-4-yl)phenyl]amide in its corresponding hydrochloride salt form as a white solid: $^1$H NMR (300 MHz, DMSO-d$_6$) δ 12.79 (s, 1H), 12.20 (s, 1H), 9.93 (s, 1H), 8.00 (s, 1H), 7.47 (s, 2H), 7.35 (m, 2H), 7.28 (m, 2H), 2.34 (m 1H), 1.80 (m, 2H), 1.74 (m, 2H), 1.40 (m, 2H), 1.94 (m, 2H), 1.23 (m, 2H); $^{13}$C NMR (100 MHz, CD$_3$OD) δ 179.1, 150.0, 142.0, 130.8, 129.5, 129.0, 121.3, 121.2, 117.4, 110.2, 48.8, 30.8, 27.0, 26.9; HRMS (ESI) calcd for C$_{16}$H$_{20}$N$_4$O (M$^+$) 284.1637. found 284.1632.

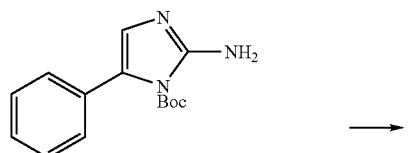

heptanoic acid
[3-(2-amino-3H-imidazol-4-yl)phenyl]amide
hydrochloride

In a similar manner, 0.056 g (0.110 mmol) of 2-amino-5-(3-heptanoylaminophenyl)imidazole-1-carboxylic acid tert-butyl ester afforded 0.046 g (98%) of heptanoic acid [3-(2-amino-3H-imidazol-4-yl)phenyl]amide in its corresponding hydrochloride salt form as an off-white solid: $^1$H NMR (300 MHz, DMSO-d$_6$) δ 12.72 (s, 1H), 12.10 (s, 1H), 10.05 (s, 1H), 7.95 (s, 1H), 7.43 (m, 2H), 7.30 (m, 3H), 7.28 (s, 1H), 2.32 (t, 2H, J=7.5 Hz), 1.59 (m, 2H), 1.28 (m, 6H), 0.87 (m, 3H); $^{13}$C NMR (100 MHz, CD$_3$OD) δ 175.1, 159.0, 149.0, 140.9, 130.8, 129.6, 129.0, 121.3, 117.3, 110.3, 38.2, 32.9, 30.1, 27.0, 23.7, 14.5; HRMS (ESI) calcd for C$_{16}$H$_{22}$N$_4$O (M$^+$) 286.1794, found 286.1790.

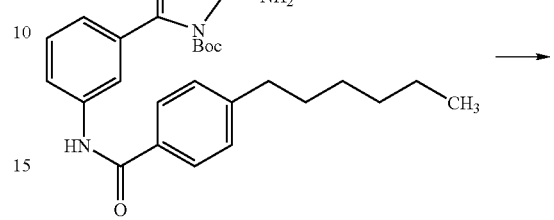

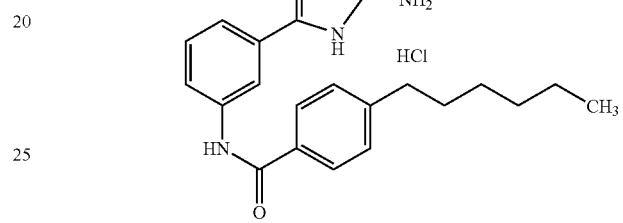

3-(2-amino-3H-imidazol-4-yl)phenyl]-4-hexylbenzamide hydrochloride

In a similar manner, 0.070 g (0.151 mmol) of 2-amino-5-[3-(4-hexylbenzoylamino)phenyl]imidazole-1-carboxylic acid tert-butyl ester afforded 0.059 g (98%) of 3-(2-amino-3H-imidazol-4-yl)phenyl]-4-hexylbenzamide in its corresponding hydrochloride salt form as a white solid: $^1$H NMR (300 MHz, DMSO-d$_6$) δ 12.77 (s, 1H), 12.12 (s, 1H), 10.32 (s, 1H), 8.02 (s, 1H), 7.90 (d, 2H, J=8.1 Hz), 7.46 (s, 2H), 7.29-7.43 (m, 6H), 2.67 (t, 2H, J=7.5 Hz), 1.60 (m, 2H), 1.29 (m, 6H), 0.86 (m, 3H); $^{13}$C NMR (100 MHz, CD$_3$OD) δ 167.7, 147.6, 139.6, 132.1, 129.7, 129.5, 128.6, 128.4, 127.9, 127.7, 121.1, 120.4, 117.1, 109.0, 35.6, 31.7, 31.2, 28.9, 22.5, 13.3; HRMS (ESI) calcd for C$_{22}$H$_{26}$N$_4$O (M$^+$) 326.2107. found 362.2101.

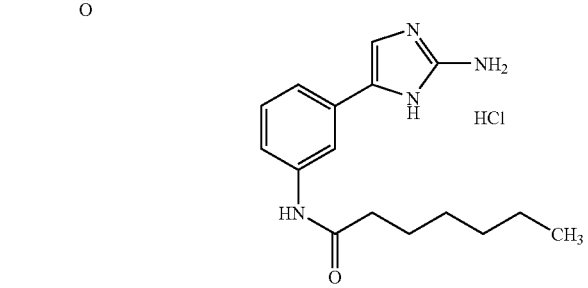

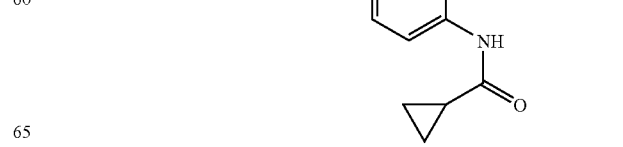

2-amino-5-[2-(cyclopropanecarbonylamino)phenyl]imidazole-1-carboxylic acid tert-butyl ester In a similar manner, 0.075 g (0.273 mmol) of 2-amino-5-(2-aminophenyl)imidazole-1-carboxylic acid tert-butyl ester afforded 0.076 g (82%) of 2-amino-5-[2-(cyclopropanecarbonylamino)phenyl]imidazole-1-carboxylic acid tert-butyl ester as an off-white solid: $^1$H NMR (300 MHz, DMSO-d$_6$) δ 12.37 (s, 1H), 8.31 (d, 1H, J=8.1 Hz), 7.70 (dd, 1H, J=1.2, 7.8 Hz), 7.38 (s, 1H), 7.18 (m, 1H), 7.01 (t, 1H, J=7.2 Hz), 6.93 (br s, 2H), 1.88 (m, 1H), 1.59 (s, 9H), 0.83 (m, 4H); $^{13}$C NMR (100 MHz, CD$_3$OD) δ 171.3, 149.6, 148.7, 136.5, 135.8, 127.6, 126.5, 122.9, 120.7, 120.0, 107.6, 85.2, 27.5, 15.6, 7.3; HRMS (ESI) calcd for C$_{18}$H$_{22}$N$_4$O$_3$ (M$^+$) 342.1692. found 342.1687.

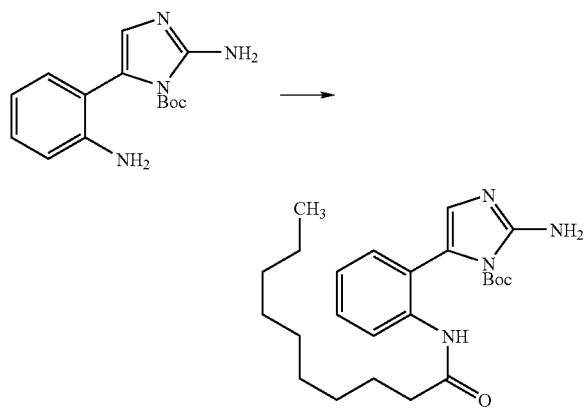

2-amino-5-(2-decanoylaminophenyl)imidazole-1-carboxylic acid tert-butyl ester In a similar manner, 0.075 g (0.273 mmol) of 2-amino-5-(2-aminophenyl)imidazole-1-carboxylic acid tert-butyl ester afforded 0.084 g (72%) of 2-amino-5-(2-decanoylaminophenyl)imidazole-1-carboxylic acid tert-butyl ester as a tan oil: $^1$H NMR (400 MHz, DMSO-d$_6$) δ 11.89 (s, 1H), 8.30 (d, 1H, J=8.0 Hz), 7.70 (dd, 1H, J=1.2, 8.0 Hz), 7.34 (s, 1H), 7.19 (m, 1H), 7.02 (t, 1H, J=6.8 Hz), 6.88 (br s, 2H), 2.37 (t, 2H, J=7.2 Hz), 1.59 (m, 11H), 1.25 (m, 12H), 0.83 (t, 3H, J=6.4 Hz); $^{13}$C NMR (100 MHz, DMSO-d$_6$) δ 171.0, 149.6, 148.7, 136.3, 135.8, 127.5, 126.6, 123.0, 120.9, 120.5, 107.5, 85.1, 37.4, 31.3, 28.9, 28.8, 28.6, 28.5, 27.5, 25.2, 22.1, 14.0; HRMS (ESI) calcd for C$_{24}$H$_{36}$N$_4$O$_3$ (M$^+$) 428.2787. found 428.2782.

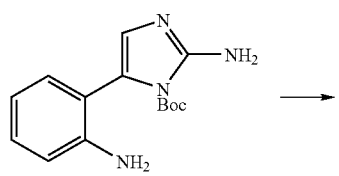

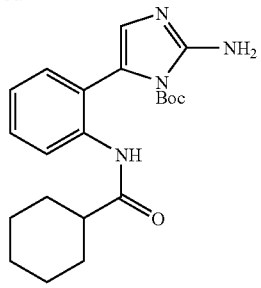

2-amino-5-[2-(cyclohexanecarbonylamino)phenyl]imidazole-1-carboxylic acid tert-butyl ester In a similar manner, 0.075 g (0.273 mmol) of 2-amino-5-(2-aminophenyl)imidazole-1-carboxylic acid tert-butyl ester afforded 0.078 g (74%) of 2-amino-5-[2-(cyclohexanecarbonylamino)phenyl]imidazole-1-carboxylic acid tert-butyl ester as a white solid: $^1$H NMR (400 MHz, DMSO-d$_6$) δ 11.65 (s, 1H), 8.26 (d, 1H, J=7.6 Hz), 7.70 (dd, 1H, J=1.2, 7.6 Hz), 7.32 (s, 1H), 7.18 (m, 1H), 7.02 (t, 1H, J=6.8 Hz), 6.86 (br s, 2H), 2.34 (m, 1H), 1.83 (m, 2H), 1.74 (m, 2H), 1.59 (m, 11H), 1.31-1.48 (m, 3H), 1.20 (m, 1H); $^{13}$C NMR (100 MHz, CD$_3$OD) δ 177.5, 150.8, 137.5, 137.2, 129.0, 128.3, 128.1, 125.4, 124.2, 123.7, 109.1, 86.9, 48.1, 30.9, 28.3, 27.1, 26.9; HRMS (ESI) calcd for C$_{21}$H$_{28}$N$_4$O$_3$ (M$^+$) 384.2161. found 384.2157.

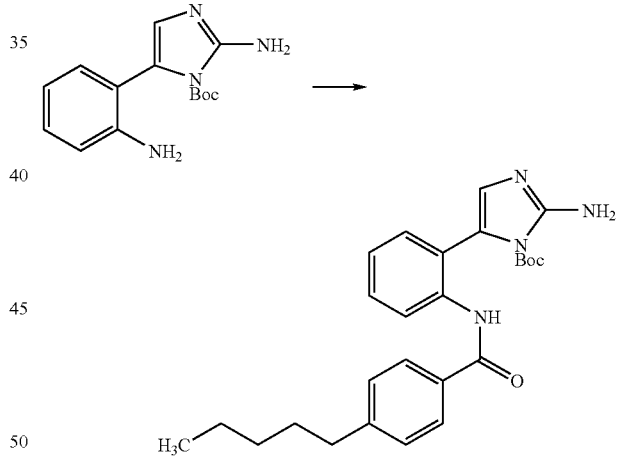

2-amino-5-[2-(4-pentylbenzoylamino)phenyl]imidazole-1-carboxylic acid tert-butyl ester In a similar manner, 0.075 g (0.273 mmol) of 2-amino-5-(2-aminophenyl)imidazole-1-carboxylic acid ter-t-butyl ester afforded 0.089 g (73%) of 2-amino-5-[2-(4-pentylbenzoylamino)phenyl]imidazole-1-carboxylic acid tert-butyl ester as a white foam: $^1$H NMR (400 MHz, DMSO-d$_6$) δ 12.41 (s, 1H), 8.52 (d, 1H, J=7.6 Hz), 7.99 (d, 2H, J=8.4 Hz), 7.71 (dd, 1H, J=1.6, 8.0 Hz), 7.41 (d, 2H, J=8.4 Hz), 7.37 (s, 1H), 7.29 (m, 1H), 7.10 (m, 1H), 6.93 (br s, 2H), 2.66 (t, 2H, J=7.2 Hz), 1.61 (m, 2H), 1.57 (s, 9H), 1.31 (m, 4H), 0.86 (t, 3H, J=6.8 Hz); $^{13}$C NMR (100 MHz, CD$_3$OD) δ 169.1, 150.8, 148.8, 137.8, 137.6, 133.7, 130.1, 130.0, 129.1, 128.8, 128.2, 125.3, 123.8, 123.1, 109.1, 86.9, 36.9, 32.8, 32.3, 28.3, 23.7, 14.5; HRMS (ESI) calcd for $C_{26}H_{32}N_4O_3$ (M+) 448.2474. found 448.2466.

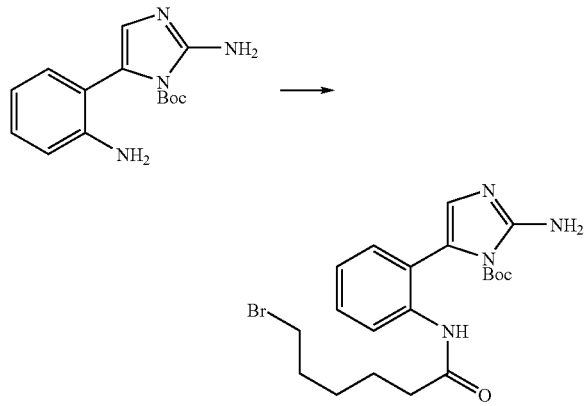

2-amino-5-[2-(6-bromohexanoylamino)phenyl]imidazole-1-carboxylic acid tert-butyl ester

In a similar manner, 0.071 g (0.258 mmol) of 2-amino-5-(2-aminophenyl)imidazole-1-carboxylic acid tert-butyl ester afforded 0.085 g (75%) of 2-amino-5-[2-(6-bromohexanoylamino)phenyl]imidazole-1-carboxylic acid tert-butyl ester as an off-white solid: $^1$H NMR (300 MHz, DMSO-$d_6$) δ 11.92 (s, 1H), 8.31 (d, 1H, J=7.5 Hz), 7.69 (dd, 1H, J=1.2, 8.1 Hz), 7.35 (s, 1H), 7.20 (m, 1H), 7.02 (m, 1H), 6.89 (br s, 2H), 3.52 (t, 2H, J=6.3 Hz), 2.39 (t, 2H, J=7.5 Hz), 1.84 (m, 2H), 1.64 (m, 2H), 1.59 (s, 9H), 1.43 (m, 2H); $^{13}$C NMR (100 MHz, CDCl$_3$) δ 171.4, 149.5, 149.3, 137.3, 137.0, 128.6, 126.6, 123.2, 121.2, 120.1, 107.8, 86.1, 38.4, 33.9, 32.7, 28.1, 28.0, 24.9; HRMS (ESI) calcd for $C_{20}H_{27}BrN_4O_3$ (M+) 450.1267. found 450.1260.

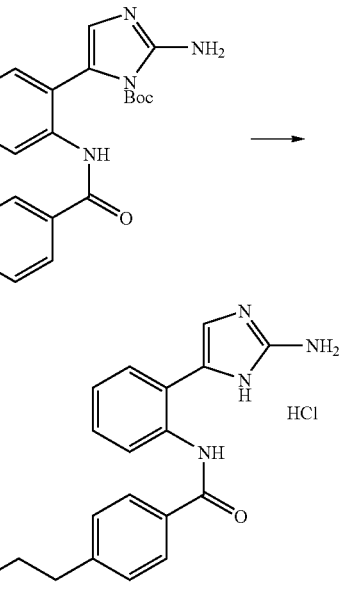

2-(2-amino-3H-imidazol-4-yl)phenyl-4-pentyl-benzamide hydrochloride

In a similar manner, 0.044 g (0.098 mmol) of 2-amino-5-[2-(4-pentylbenzoylamino)phenyl]imidazole-1-carboxylic acid tert-butyl ester afforded 0.037 g (99%) of 2-(2-amino-3H-imidazol-4-yl)phenyl-4-pentyl-benzamide in its corresponding hydrochloride salt form as a white solid: $^1$H NMR (300 MHz, DMSO-$d_6$) δ 12.69 (s, 1H), 11.93 (s, 1H), 10.02 (s, 1H), 7.88 (d, 2H, J=8.1 Hz), 7.53 (m, 2H), 7.46 (m, 2H), 7.40 (m, 1H), 7.33 (d, 2H, J=8.1 Hz), 6.96 (s, 1H), 2.64 (t, 2H, J=7.2 Hz), 1.60 (m, 2H), 1.29 (m, 4H), 0.87 (t, 3H, J=6.6 Hz); $^{13}$C NMR (100 MHz, CD$_3$OD) δ 169.5, 149.2, 149.0, 136.3, 132.7, 130.7, 130.0, 129.9, 129.4, 129.0, 128.5, 126.3, 126.1, 112.0, 36.9, 32.7, 32.3, 23.7, 14.5; HRMS (ESI) calcd for $C_{21}H_{24}N_4O$ (M+) 348.1950. found 348.1945.

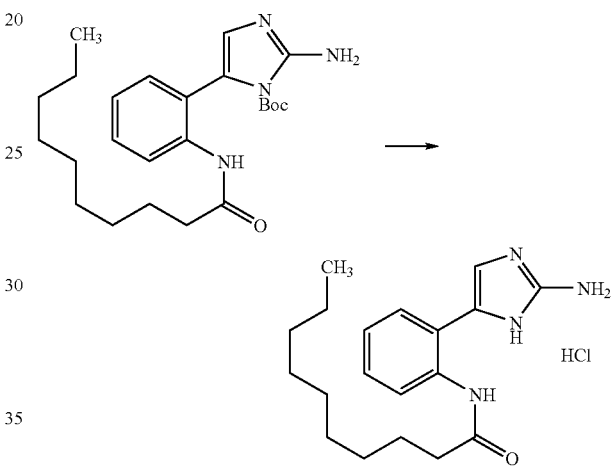

decanoic acid 2-(2-amino-3H-imidazol-4-yl)phenyl amide hydrochloride

In a similar manner, 0.046 g (0.107 mmol) of 2-amino-5-(2-decanoylaminophenyl)imidazole-1-carboxylic acid tert-butyl ester afforded 0.039 g (99%) of decanoic acid 2-(2-amino-3H-imidazol-4-yl)phenyl amide in its corresponding hydrochloride salt form as a white solid: $^1$H NMR (300 MHz, DMSO-$d_6$) δ 12.58 (s, 1H), 12.10 (s, 1H), 9.47 (s, 1H), 7.46 (m, 4H), 7.36 (m, 1H), 7.27 (t, 1H, J=7.2 Hz), 7.03 (s, 1H), 2.30 (t, 2H, J=6.9 Hz), 1.55 (m, 2H), 1.25 (br s, 12H), 0.86 (t, 3H, J=6.6 Hz); $^{13}$C NMR (100 MHz, CD$_3$OD) δ 175.7, 149.0, 136.2, 130.7, 130.1, 128.6, 128.0, 125.8, 125.3, 112.2, 37.5, 33.2, 30.7, 30.6, 30.5, 26.9, 23.9, 14.6; HRMS (ESI) calcd for $C_{19}H_{28}N_4O$ (M+) 328.2263. found 328.2260.

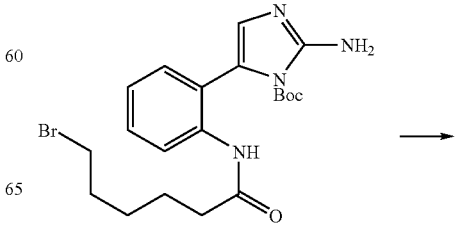

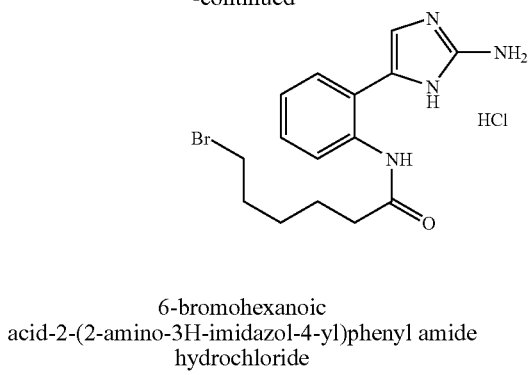

6-bromohexanoic acid-2-(2-amino-3H-imidazol-4-yl)phenyl amide hydrochloride

In a similar manner, 0.038 g (0.084 mmol) of 2-amino-5-[2-(6-bromohexanoylamino)phenyl]imidazole-1-carboxylic acid tert-butyl ester afforded 0.032 g (97%) of 6-bromohexanoic acid-2-(2-amino-3H-imidazol-4-yl)phenyl amide in its corresponding hydrochloride salt form as a tan solid: $^1$H NMR (400 MHz, DMSO-d$_6$) δ 12.64 (s, 1H), 12.19 (s, 1H), 9.46 (s, 1H), 7.53 (m, 3H), 7.44 (d, 1H, J=7.2 Hz), 7.36 (t, 1H, J=6.8 Hz), 7.27 (t, 1H, J=7.2 Hz), 7.03 (s, 1H), 3.54 (t, 2H, J=7.2 Hz), 2.32 (t, 2H, J=6.9 Hz), 1.82 (tt, 2H, J=6.9, 14.0 Hz), 1.59 (tt, 2H, J=6.8, 14.4 Hz), 1.41 (tt, 2H, J=8.0, 14.8 Hz); $^{13}$C NMR (100 MHz, CD$_3$OD) δ 175.3, 149.5, 136.2, 130.7, 130.2, 128.6, 128.0, 125.8, 125.3, 112.2, 37.2, 34.3, 33.7, 29.0, 25.9; HRMS (ESI) calcd for C$_{15}$H$_{19}$BrN$_4$O (M$^+$) 350.0742. found 350.0739.

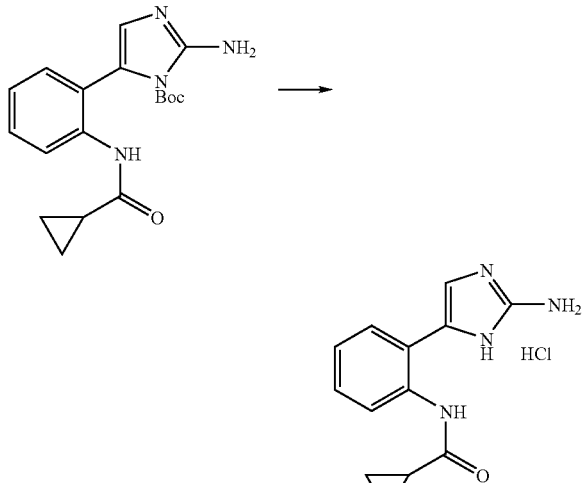

cyclopropanecarboxylic acid 2-(2-amino-3H-imidazol-4-yl)phenyl amide hydrochloride In a similar manner, 0.046 g (0.134 mmol) of 2-amino-5-[2-(cyclopropanecarbonylamino)phenyl]imidazole-1-carboxylic acid tert-butyl ester afforded 0.036 g (97%) of cyclopropanecarboxylic acid 2-(2-amino-3H-imidazol-4-yl)phenyl amide in its corresponding hydrochloride salt form as a tan solid: $^1$H NMR (300 MHz, DMSO-d$_6$) δ 12.69 (s, 1H), 12.17 (s, 1H), 9.82 (s, 1H), 7.51 (m, 4H), 7.35 (m, 1H), 7.28 (t, 1H, J=6.3 Hz), 7.03 (s, 1H), 1.88 (m, 1H), 0.76 (d, 4H, J=5.7 Hz); $^{13}$C NMR (100 MHz, CD$_3$OD) δ 176.0, 149.1, 136.3, 130.7, 129.9, 128.5, 127.9, 125.6, 125.1, 112.3, 15.4, 8.2; HRMS (ESI) calcd for C$_{13}$H$_{14}$N$_4$O (M$^+$) 242.1168. found 242.1164.

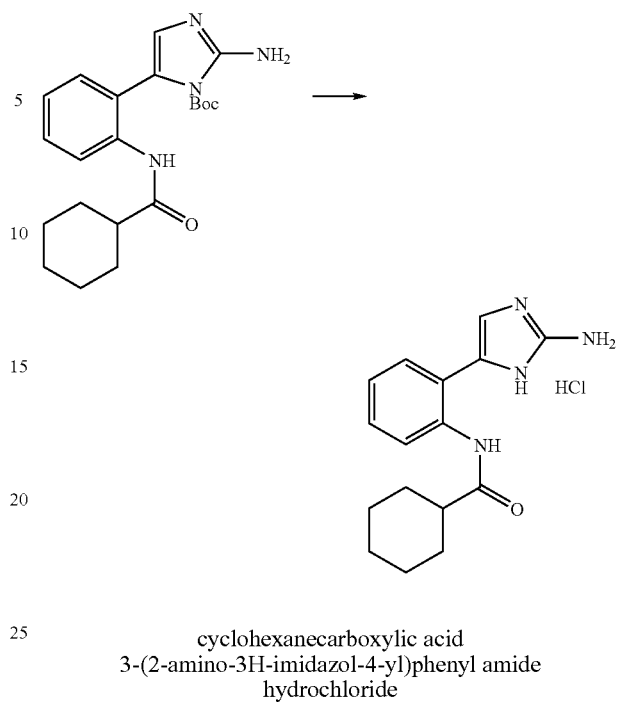

cyclohexanecarboxylic acid 3-(2-amino-3H-imidazol-4-yl)phenyl amide hydrochloride In a similar manner, 0.041 g (0.106 mmol) of 2-amino-5-[2-(cyclohexanecarbonylamino)phenyl]imidazole-1-carboxylic acid tert-butyl ester afforded 0.032 g (94%) of cyclohexanecarboxylic acid 3-(2-amino-3H-imidazol-4-yl)phenyl amide in its corresponding hydrochloride salt form as a white solid: $^1$H NMR (300 MHz, DMSO-d$_6$) δ 12.58 (s, 1H), 12.05 (s, 1H), 9.41 (s, 1H), 7.45 (m, 4H), 7.35 (m, 1H), 7.28 (t, 1H, J=7.8 Hz), 6.99 (s, 1H), 2.36 (m, 1H), 1.63-1.83 (m, 4H), 1.20-1.41 (m, 6H); $^{13}$C NMR (100 MHz, CD$_3$OD) δ 178.4, 148.9, 136.3, 132.5, 130.8, 130.2, 128.7, 128.1, 125.7, 112.2, 46.6, 30.6, 27.0, 26.9; HRMS (ESI) calcd for C$_{16}$H$_{20}$N$_4$O (M$^+$) 284.1637. found 284.1635.

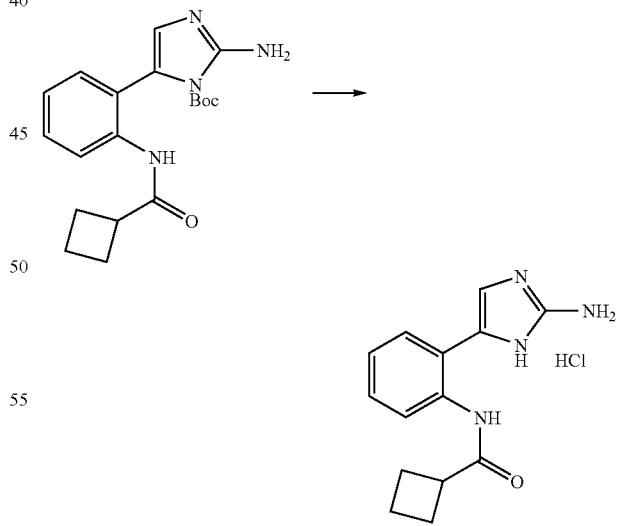

cyclobutanecarboxylic acid [2-(2-amino-3H-imidazol-4-yl)phenyl]amide hydrochloride In a similar manner, 0.044 g (0.122 mmol) of 2-amino-5-[2-(cyclobutanecarbonylamino)phenyl]imidazole-1-carboxylic acid tert-butyl ester afforded 0.034 g (98%) of cyclobutanecarboxylic acid [2-(2-amino-3H-imidazol-4-yl)phenyl]amide in its corresponding hydrochloride salt form as a yellow solid: $^1$H NMR (300 MHz, DMSO-d$_6$) δ 12.47 (s, 1H), 12.00 (s, 1H), 9.30 (s, 1H), 7.53 (d, 1H, J=6.0), 7.45 (s, 2H), 7.35 (t, 1H, J=6.4 Hz), 7.29 (t, 1H, J=7.2 Hz), 6.96 (s, 1H), 3.25 (t, 1H, J=6.3 Hz), 2.04 (m, 2H), 2.50 (m, 2H), 1.48 (m, 2H); $^{13}$C NMR (100 MHz, CD$_3$OD) δ 176.9, 148.0, 136.2, 130.7, 130.0, 128.6, 128.0, 125.9, 125.3, 112.2, 41.2, 26.2, 19.2; HRMS (ESI) calcd for C$_{14}$H$_{17}$N$_4$O (M$^+$) 256.1324. found 256.1319.

EXAMPLE 5

Synthesis of 2-Aminoimidazole Libraries for Anti-Biofilm Screening

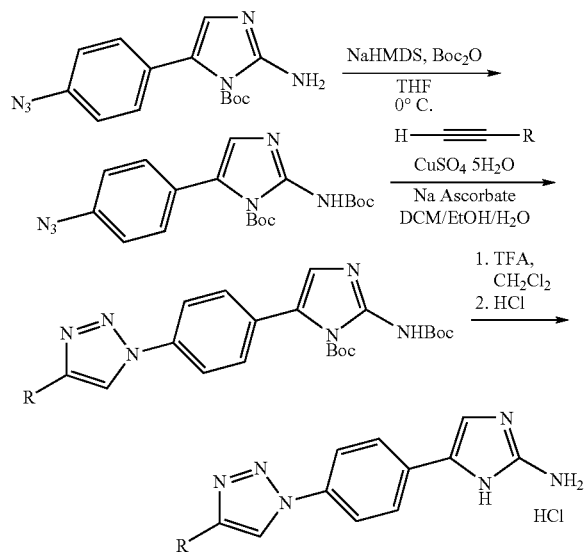

The following compounds have been synthesized.

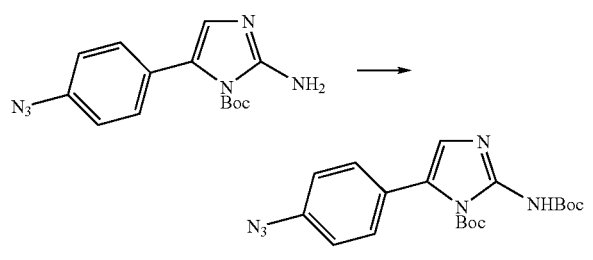

2-amino-5-(4-azidophenyl)imidazole-1-carboxylic acid tert-butyl ester (0.229 g, 0.762 mmol) was dissolved in anhydrous THF (2.5 mL) and cooled to 0° C. NaHMDS (1M in THF)(1.53 mL, 1.53 mmol) was added to the reaction dropwise. Boc-anhydride (0.174 g, 0.800 mmol) was dissolved in anhydrous THF (2 mL) and added to the reaction. The reaction was allowed to stir for 15 min at 0° C. then allowed to stir at warm to room temperature for 20 min. After the reaction was quenched with sat. NH$_4$Cl and diluted with EtOAc (50 mL). The organic layer was then extracted with brine (3×20 mL) before being dried (NaSO$_4$), filtered, and evaporated to dryness. The crude product was purified by column chromatography (10-30% EtOAc/Hexanes) to afford 0.230 g (75%) of the target compound 5-(4-azidophenyl)-2-tert-butoxycarbonylaminoimidazole-1-carboxylic acid tert-butyl ester as a white solid: $^1$H NMR (300 MHz, DMSO-d$_6$) δ 9.54 (s, 1H), 7.88 (s, 1H), 8.5 (d, 2H, J=8.7 Hz), 7.14 (d, 2H, J=8.7 Hz), 1.57 (s, 9H), 1.44 (s, 9H); $^{13}$C NMR (75 MHz, DMSO-d$_6$) δ 152.8, 146.7, 139.6, 138.1, 136.2, 129.7, 126.2, 119.3, 112.5, 85.2, 80.0, 70.8, 27.9, 27.3; HRMS (ESI) calcd for C$_{19}$H$_{24}$N$_6$O$_4$ (M$^+$) 400.1857. found 400.1859.

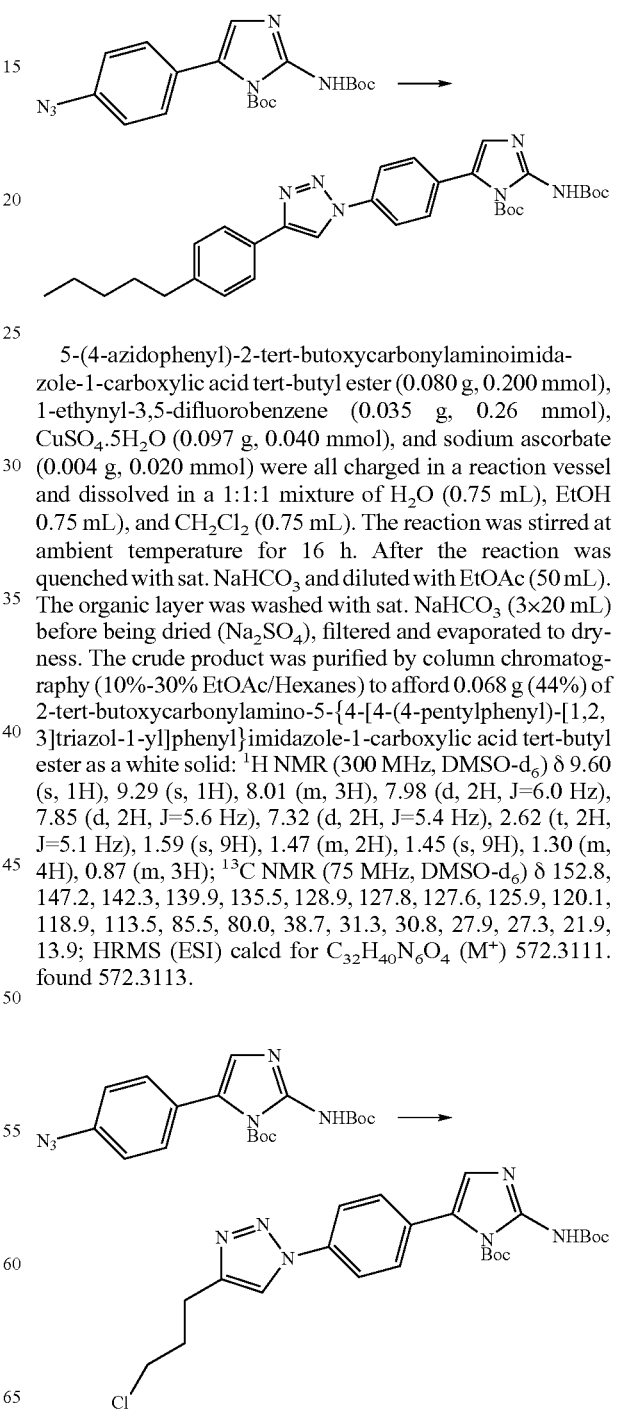

5-(4-azidophenyl)-2-tert-butoxycarbonylaminoimidazole-1-carboxylic acid tert-butyl ester (0.080 g, 0.200 mmol), 1-ethynyl-3,5-difluorobenzene (0.035 g, 0.26 mmol), CuSO$_4$.5H$_2$O (0.097 g, 0.040 mmol), and sodium ascorbate (0.004 g, 0.020 mmol) were all charged in a reaction vessel and dissolved in a 1:1:1 mixture of H$_2$O (0.75 mL), EtOH 0.75 mL), and CH$_2$Cl$_2$ (0.75 mL). The reaction was stirred at ambient temperature for 16 h. After the reaction was quenched with sat. NaHCO$_3$ and diluted with EtOAc (50 mL). The organic layer was washed with sat. NaHCO$_3$ (3×20 mL) before being dried (Na$_2$SO$_4$), filtered and evaporated to dryness. The crude product was purified by column chromatography (10%-30% EtOAc/Hexanes) to afford 0.068 g (44%) of 2-tert-butoxycarbonylamino-5-{4-[4-(4-pentylphenyl)-[1,2,3]triazol-1-yl]phenyl}imidazole-1-carboxylic acid tert-butyl ester as a white solid: $^1$H NMR (300 MHz, DMSO-d$_6$) δ 9.60 (s, 1H), 9.29 (s, 1H), 8.01 (m, 3H), 7.98 (d, 2H, J=6.0 Hz), 7.85 (d, 2H, J=5.6 Hz), 7.32 (d, 2H, J=5.4 Hz), 2.62 (t, 2H, J=5.1 Hz), 1.59 (s, 9H), 1.47 (m, 2H), 1.45 (s, 9H), 1.30 (m, 4H), 0.87 (m, 3H); $^{13}$C NMR (75 MHz, DMSO-d$_6$) δ 152.8, 147.2, 142.3, 139.9, 135.5, 128.9, 127.8, 127.6, 125.9, 120.1, 118.9, 113.5, 85.5, 80.0, 38.7, 31.3, 30.8, 27.9, 27.3, 21.9, 13.9; HRMS (ESI) calcd for C$_{32}$H$_{40}$N$_6$O$_4$ (M$^+$) 572.3111. found 572.3113.

In a similar manner, 0.051 g (0.127 mmol) 5-(4-azidophenyl)-2-tert-butoxycarbonylaminoimidazole-1-carboxylic acid tert-butyl ester afforded 0.044 g (68%) of compound 2-tert-butoxycarbonylamino-5-{4-[4-(3-chloropropyl)-[1,2,3]triazol-1-yl]phenyl}imidazole-1-carboxylic acid tert-butyl ester as a yellow solid: $^1$H NMR (300 MHz, DMSO-d$_6$) δ 9.18 (s, 1H), 7.95 (d, 2H, J=4.8 Hz), 7.78 (s, 1H), 7.68 (m, 2H), 7.24 (s, 1H), 3.60 (t, 2H, J=6.3 Hz), 2.96 (t, 2H, J=7.5 Hz), 2.23 (m, 2H); $^{13}$C NMR (75 MHz, DMSO-d$_6$) δ 150.1, 149.4, 147.3, 142.8, 137.9, 136.4, 133.3, 126.9, 120.5, 119.4, 108.5, 87.2, 82.2, 44.3, 32.0, 28.4, 28.2, 22.9; HRMS (ESI) calcd for C$_{24}$H$_{32}$N$_6$O$_4$Cl (M$^+$) 502.2095. found 502.2094.

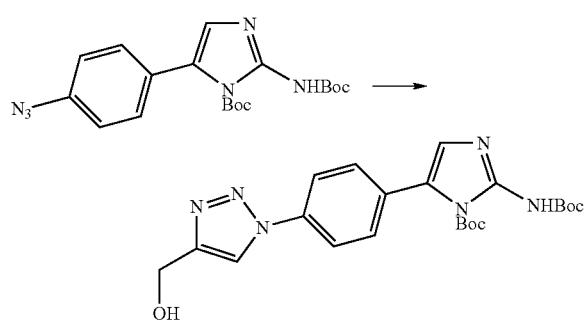

In a similar manner, 0.074 g (0.185 mmol) of 5-(4-azidophenyl)-2-tert-butoxycarbonylaminoimidazole-1-carboxylic acid tert-butyl ester afforded 0.084 g (35%) of compound 2-tert-butoxycarbonylamino-5-[4-(4-hydroxymethyl-[1,2,3]triazol-1-yl)phenyl]imidazole-1-carboxylic acid tert-butyl ester as a white solid: $^1$H NMR (300 MHz, DMSO-d$_6$) δ 9.59 (s, 1H), 8.71 (s, 1H), 7.99 (m, 3H), 7.92 (d, 2H, J=9.0 Hz), 4.61 (d, 2H, J=3.0 Hz), 1.59 (s, 9H), 1.48 (s, 9H); $^{13}$C NMR (75 MHz, DMSO-d$_6$) δ 153.0, 149.5, 139.4, 135.9, 134.4, 132.8, 125.9, 125.0, 120.8, 119.1, 113.5, 85.4, 80.2, 54.9, 27.9, 27.7; HRMS (ESI) calcd for C$_{22}$H$_{28}$N$_6$O$_5$ (M$^+$) 456.2121. found 456.2121.

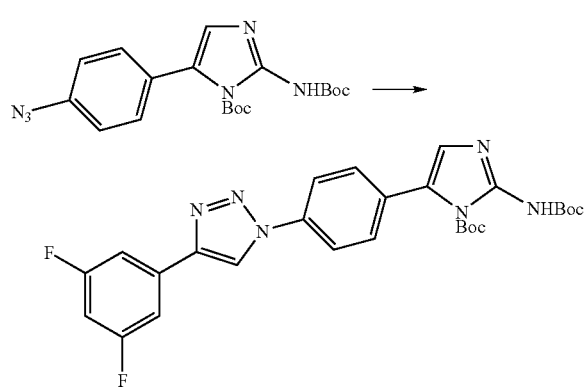

In a similar manner, 0.080 g (0.199 mmol) of 5-(4-azidophenyl)-2-tert-butoxycarbonylaminoimidazole-1-carboxylic acid tert-butyl ester afforded 0.108 g (56%) of compound 2-tert-butoxycarbonylamino-5-{4-[4-(3,5-difluorophenyl)-[1,2,3]triazol-1-yl]phenyl}imidazole-1-carboxylic acid tert-butyl ester as a white solid: $^1$H NMR (300 MHz, DMSO-d$_6$) δ 9.61 (s, 1H), 9.48 (s, 1H), 8.10 (m, 3H), 7.95 (d, 2H, J=8.7 Hz), 7.67 (m, 2H), 7.30 (m, 1H), 1.59 (s, 9H), 1.45 (s, 9H); $^{13}$C NMR (75 MHz, DMSO-d$_6$) δ 164.4, 161.2, 152.8, 146.7, 145.3, 139.9, 135.9, 135.2, 133.3, 126.0, 120.9, 120.2, 113.6, 108.4, 108.1, 85.4, 80.1, 27.9, 27.3; HRMS (ESI) calcd for C$_{27}$H$_{28}$N$_6$O$_4$F$_2$ (M$^+$) 538.2140. found 538.2143.

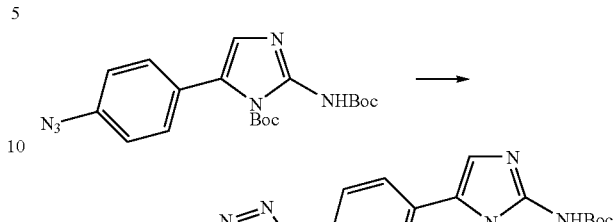

In a similar manner, 0.070 g (0.175 mmol) 5-(4-azidophenyl)-2-tert-butoxycarbonylaminoimidazole-1-carboxylic acid tert-butyl ester afforded 0.060 g (73%) of compound 2-tert-butoxycarbonylamino-5-[4-(4-cyclopropyl-[1,2,3]triazol-1-yl)-phenyl]imidazole-1-carboxylicacid tert-butyl ester as a white solid: $^1$H NMR (300 MHz, DMSO-d$_6$) δ 9.60 (s, 1H), 8.56 (s, 1H), 8.10 (m, 3H), 7.87 (d, 2H, J=8.5 Hz), 2.00 (m, 1H), 1.50 (s, 9H), 1.40 (s, 9H) 0.98 (m, 2H), 0.810 (m, 2H); $^{13}$C NMR (75 MHz, DMSO-d$_6$) δ 153.5, 152.7, 150.7, 134.8, 124.3, 119.4, 118.9, 80.75, 68.0, 48.9, 31.5, 28.3, 28.0, 8.2, 6.9; HRMS (ESI) calcd for C$_{24}$H$_{30}$N$_6$O$_4$ (M$^+$) 466.2329. found 466.2326.

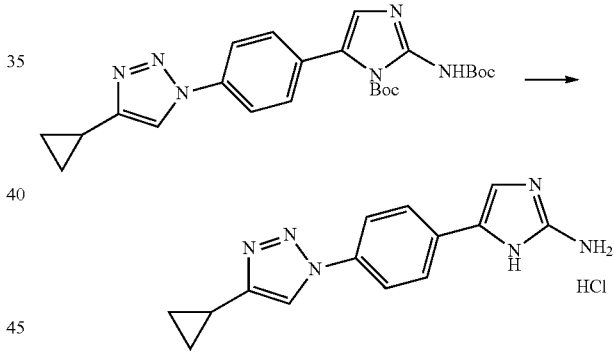

2-tert-butoxycarbonylamino-5-[4-(4-cyclopropyl-[1,2,3]triazol-1-yl)phenyl]imidazole-1-carboxylicacid tert-butyl ester (0.047 g, 0.089 mmol) was dissolved in anhydrous dichloromethane (5 mL) and cooled to 0° C. Trifluoroacetic acid (0.5 mL) was added drop-wise while the reaction continued to stir at 0° C. Upon completion, the reaction was allowed to warm to room temperature over the course of 15 h. Then the reaction was evaporated down. The crude TFA salt was the dissolved in dichloromethane (2 mL) and a 2M solution of HCl in diethyl ether (0.100 mL) was added. The solution was again concentrated down under vacuum to afford 0.033 g (98%) of desired product 5-[4-(4-cyclopropyl-[1,2,3]triazol-1-yl)phenyl]-1H-imidazol-2-ylamine in its corresponding hydrochloride salt form as an off-white solid: $^1$H NMR (300 MHz, DMSO-d$_6$) δ 13.20 (s, 1H), 12.30 (s, 1H), 8.59 (s, 1H), 7.92 (m, 4H), 7.52 (m, 3H), 2.01 (m, 1H), 0.98 (m, 2H), 0.80 (m, 2H); $^{13}$C NMR (100 MHz, DMSO-d$_6$) δ 151.4, 147.6, 135.6, 127.4, 125.3, 120.0, 118.5, 110.2, 94.0, 7.6, 6.2; HRMS (ESI) calcd for C$_{14}$H$_{14}$N$_6$ (M$^+$) 266.1280. found 266.1282.

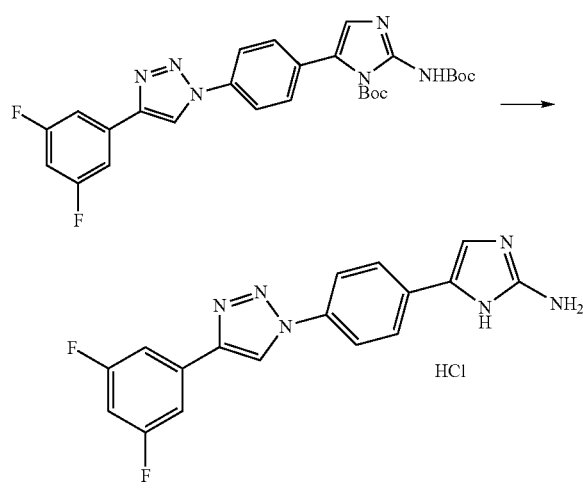

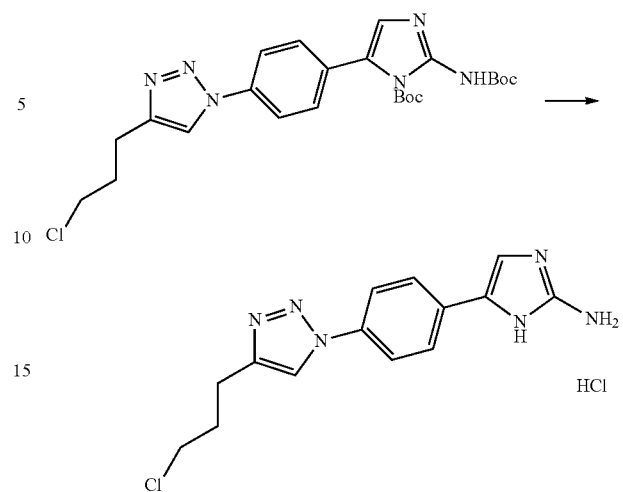

In a similar manner, 0.047 g (0.088 mmol) 2-tert-butoxycarbonylamino-5-{4-[4-(3,5-difluorophenyl)-[1,2,3]triazol-1-yl]-phenyl}imidazole-1-carboxylic acid tert-butyl ester afforded 0.033 g (98%) of compound 5-{4-[4-(3,5-difluorophenyl)-[1,2,3]triazol-1-yl-phenyl}-1H-imidazol-2-ylamine in its corresponding hydrochloride salt form as a white solid: $^1$H NMR (300 MHz, DMSO-$d_6$) δ 13.05 (s, 1H), 12.15 (s, 1H), 9.51 (s, 1H), 8.03 (m, 4H), 7.66 (m, 2H), 7.57 (s, 3H), 7.28 (m, 1H); $^{13}$C NMR (75 MHz, DMSO-$d_6$) δ 161.2, 156.4, 147.8, 145.3, 135.4, 128.2, 125.5, 125.4, 120.8, 120.6, 110.6, 108.4, 108.1; HRMS (ESI) calcd for $C_{17}H_{12}N_6F_2$ (M$^+$) 338.1092. found 338.1093.

In a similar manner, 0.028 g (0.057 mmol) 2-tert-butoxycarbonylamino-5-{4-[4-(3-chloropropyl)-[1,2,3]triazol-1-yl]phenyl}imidazole-1-carboxylic acid tert-butyl ester afforded 0.018 g (93%) of compound 5-{4-[4-(3-chloropropyl)-[1,2,3]triazol-1-yl]phenyl}-1H-imidazol-2-ylamine in its corresponding hydrochloride salt form as a brown solid: $^1$H NMR (300 MHz, DMSO-$d_6$) δ 13.06 (s, 1H), 12.24 (s, 1H), 8.61 (s, 1H), 7.97 (d, 2H, J=9.0 Hz), 7.88 (d, 2H, J=8.7 Hz), 7.54 (m, 3H), 3.74 (t, 2H, J=6.3 Hz), 2.86 (m, 2H, J=6.9 Hz), 2.13 (m, 2H); $^{13}$C NMR (100 MHz, DMSO-$d_6$) δ 149.8, 148.0, 137.6, 130.4, 127.7, 127.2, 123.5, 122.6, 111.8, 45.0, 33.0, 23.3; HRMS (ESI) calcd for $C_{14}H_{15}N_6Cl$ (M$^+$) 302.1050. found 302.1047.

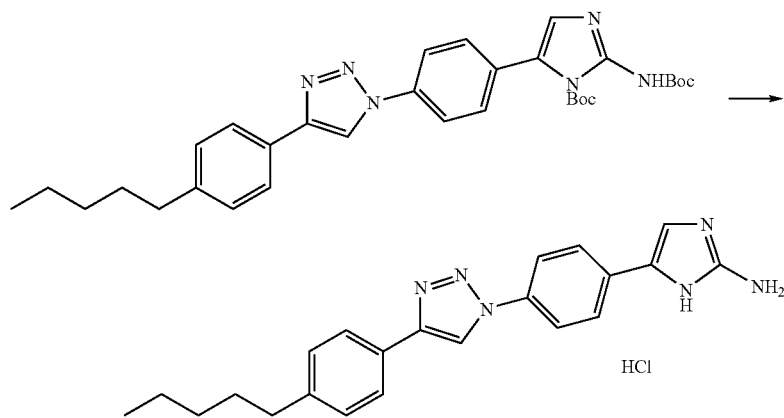

In a similar manner, 0.051 g (0.090 mmol) 2-tert-butoxycarbonylamino-5-{4-[4-(4-pentylphenyl)-[1,2,3]triazol-1-yl]-phenyl}imidazole-1-carboxylic acid tert-butyl ester afforded 0.036 g (98%) of compound 5-{4-[4-(4-pentylphenyl)-[1,2,3]triazol-1-yl-phenyl}-1H-imidazol-2-ylamine in its corresponding hydrochloride salt form as a brown solid: $^1$H NMR (300 MHz, DMSO-$d_6$) δ 13.12 (s, 1H), 12.27 (s, 1H), 9.31 (s, 1H), 8.06 (d, 2H, J=9.0 Hz), 7.93 (d, 2H, J=8.4 Hz), 7.85 (d, 2H, J=8.1 Hz), 7.57 (m, 3H), 7.32 (d, 2H, J=8.1 Hz), 2.62 (t, 2H, J=7.2 Hz), 1.60 (m, 2H), 1.29 (m, 4H), 0.87 (t, 3H, J=6.6 Hz); $^{13}$C NMR (75 MHz, DMSO-$d_6$) δ 147.9, 147.5, 142.6, 135.7, 128.8, 127.9, 127.6, 125.5, 125.4, 125.3, 120.2, 119.0, 110.5, 35.6, 31.6, 31.2, 22.6, 14.6; HRMS (ESI) calcd for $C_{22}H_{24}N_6$ (M$^+$) 372.2062. found 372.2062.

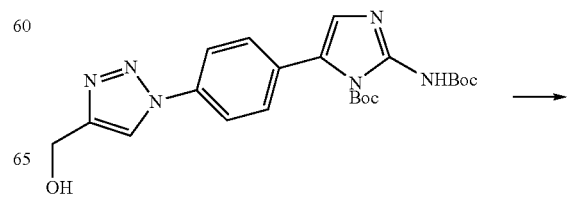

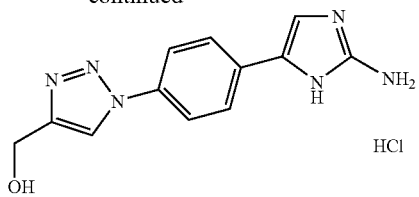

In a similar manner, 0.020 g (0.045 mmol) 2-tert-butoxycarbonylamino-5-[4-(4-hydroxymethyl-[1,2,3]triazol-1-yl)phenyl]imidazole-1-carboxylic acid tert-butyl ester afforded 0.014 g (98%) of compound {1-[4-(2-amino-3H-imidazol-4-yl)phenyl]-1H-[1,2,3]triazol-4-yl}methanol in its corresponding hydrochloride salt form as an off-white solid: $^1$H NMR (300 MHz, CD$_3$OD) δ 8.52 (s, 1H), 7.85 (d, 2H, J=8.7 Hz), 7.70 (d, 2H, J=8.7 Hz), 7.20 (s, 1H), 4.72 (m, 2H); $^{13}$C NMR (75 MHz, CD$_3$OD) δ 178.5, 136.2, 129.0, 127.0, 126.6, 122.0, 121.5, 111.1, 71.0, 55.0; HRMS (ESI) calcd for C$_{12}$H$_{12}$N$_6$O (M$^+$) 256.1073. found 256.1074.

EXAMPLE 6

Activity Testing of Compounds Against Bacterial Strains

General Static Bacterial Biofilm Inhibition Assay Procedure for *A. baumannii, P. Aeruginosa* and *S. aureus:*

Biofilm inhibition assays are performed by taking an overnight culture of bacterial strain and subculturing it at an OD$_{600}$ of 0.10 into the necessary growth liquid medium (LB for *A. baumannii*, LBNS for *P. aeruginosa*, and TSBG for *S. aureus*) for the strain. The compound being tested is then added at a predetermined concentration and then aliquoted (100 μL) into the wells of a 96-well PVC microtiter plate (Wells not used for samples are filled with 100 μL of de-ionized water). Plates are then wrapped in GLAD Press n' Seal® and incubated under stationary conditions at 37° C. After 24 hours, the media is discarded from the wells and the plates are washed thoroughly with tap water. Plates are then stained with 100 μL of 0.1% solution of crystal violet (CV) and then incubated at an ambient temperature for 30 minutes. Sample plates are then washed with tap water again, and the remaining stain is solubilized with 200 μL of 95% ethanol. Biofilm inhibition os quantitated by measuring the OD$_{540}$ for each well by transferring 125 μL of the solubilized CV stain into a polystyrene microtiter dish for analysis.

General Static Bacterial Biofilm Dispersion Assay Procedure for *A. baumannii, P. aeruginosa* and *S. aureus:*

Dispersion assays are performed by taking an overnight culture of bacterial strain and subculturing it at an OD$_{600}$ of 0.10 into the necessary growth liquid medium. The resulting bacterial suspension is aliquoted (100 μL) into the wells of a 96-well PVC microtiter plate. Plates are then wrapped in GLAD Press n' Seal® followed by an incubation under stationary conditions at an ambient temperature. After 24 hours, the media is discarded from the wells and the plates are washed thoroughly with tap water. Predetermined concentrations of the compound are then made in the same medium used to initially grow the biofilms and then aliquoted (100 μL) into the wells of the 96-well PVC microtiter plate with the established biofilms. Plates are then wrapped in GLAD Press n' Seal® and incubated under stationary conditions at 37° C. After 24 hours, the media is discarded from the wells and the plates are washed thoroughly with tap water. Plates are then stained with 100 μL of 0.1% solution of crystal violet (CV) and then incubated at room temperature for 30 minutes. Plates are then washed with tap water again and the remaining stain was solubilized with 200 μL of 95% ethanol. Biofilm dispersion is quantitated by measuring the OD$_{540}$ for each well by transferring 125 μL of the solubilized CV stain into a polystyrene microtiter dish for analysis.

General Planktonic Growth Curve Procedure:

Bacterial strains are grown in the absence or presence of the test compound at the IC$_{50}$ value starting at an OD$_{600}$ of 0.1 in culture tubes in an incubator shaker at 37° C. at 200 rpm. The OD$_{600}$ is recorded at 1, 3, 4, 5, 6 and 24 hrs.

General Colony Count Procedure for *A. baumannii P. Aeruginosa* and *S. aeureus:*

Colony counts are performed by incubating either bacterial strain in the presence and absence of the test compound at 37° C. in culture tubes until the sample with the absence of the test compound reached an OD$_{600}$ of 0.40 from a starting OD$_{600}$ of 0.10. This typically takes three to four hours. Once the OD$_{600}$ of approximately 0.40 was observed, 100 μL are taken from each culture tube from which serial dilutions are made. Then, 10 μL are removed from each serial dilution and plated out on a square gridded petri-dish followed by 16 hours of incubation at 37° C. period to grow countable colonies. Viable bacteria are quantified through employment of the track-dilution method (Jett et al., Bio Techniques. 1997, 23, 648-650).

The foregoing is illustrative of the invention, and is not to be construed as limiting thereof. The invention is defined by the following claims, with equivalents to be included.

That which is claimed is:

1. A composition comprising a compound of Formula (I)(a):

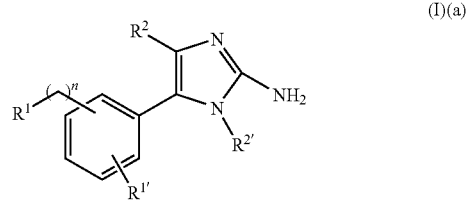

(I)(a)

wherein:
R$^1$ is C5 or C6 alkyl;
R$^{1'}$, R$^2$ and R$^{2'}$ are each H; and
n=0;
or a pharmaceutically acceptable salt thereof
and a carbapenem antibiotic.

2. The composition of claim 1, wherein R$^1$ is C6 alkyl.

3. The composition of claim 1, wherein said compound of Formula (I)(a) has the formula:

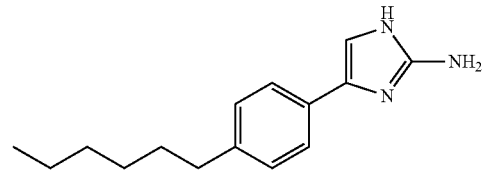 [SMILES: CCCCCCc1ccc(-c2c[nH]c(N)n2)cc1]

or a pharmaceutically acceptable salt thereof.

* * * * *

UNITED STATES PATENT AND TRADEMARK OFFICE
CERTIFICATE OF CORRECTION

PATENT NO. : 9,005,643 B2
APPLICATION NO. : 12/417981
DATED : April 14, 2015
INVENTOR(S) : Melander et al.

It is certified that error appears in the above-identified patent and that said Letters Patent is hereby corrected as shown below:

Specification

Column 25, Lines 2-10, Formula (IV)(a)(1): Please correct the formula below:

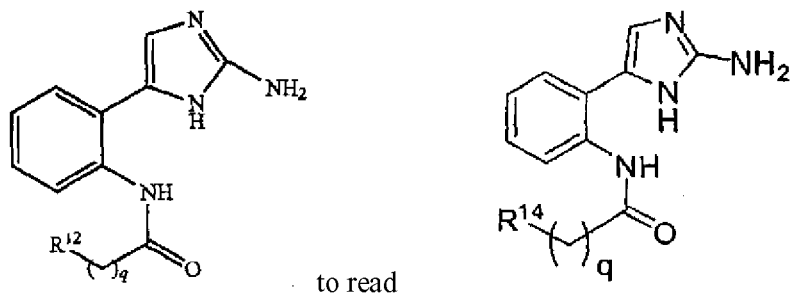

to read

Column 26, Lines 5-15, Formula (V): Please add (V) under the Formula so that it reads as follows:

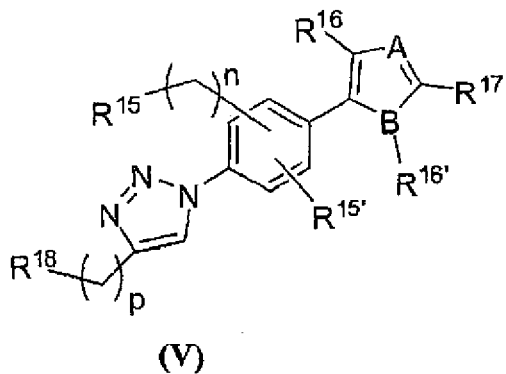

(V)

Column 65, Line 4: Please correct "$C_2H_{32}N_3O_5$" to read -- $C_{28}H_{32}N_3O_5$ --

Signed and Sealed this
Twelfth Day of April, 2016

Michelle K. Lee
*Director of the United States Patent and Trademark Office*

CERTIFICATE OF CORRECTION (continued)
U.S. Pat. No. 9,005,643 B2

Column 75, Line 35: Please correct "$CO_{18}H_{18}N_4O_2$"
to read -- $C_{18}H_{18}N_4O_2$ --

Column 88, Line 55: Please correct "$C_{21}H_{25}N_4O_3$"
to read -- $C_{21}H_{28}N_4O_3$ --

Column 89, Line 28: Please correct "$CH_{21}H_{21}N_5O_5$"
to read -- $C_{21}H_{21}N_5O_5$ --

Column 95, Line 4: Please correct "$C_{21}1H_{24}N_4O$"
to read -- $C_{21} H_{24}N_4O$ --